United States Patent [19]

Liang

[11] Patent Number: 4,774,337

[45] Date of Patent: Sep. 27, 1988

[54] HERBICIDAL PYRIDINESULFONYLUREAS

[75] Inventor: Paul H. Liang, Wilmington, Del.

[73] Assignee: E. I. Du Pont de Nemours and Company, Wilmington, Del.

[21] Appl. No.: 101,148

[22] Filed: Sep. 25, 1987

Related U.S. Application Data

[63] Continuation-in-part of Ser. No. 039,491, Apr. 16, 1987, abandoned, which is a continuation-in-part of Ser. No. 939,428, Dec. 8, 1986, abandoned.

[51] Int. Cl.$^4$ ............................................ C07D 213/71
[52] U.S. Cl. ...................................................... 546/293

[58] Field of Search ......................................... 546/293

[56] References Cited

U.S. PATENT DOCUMENTS 4,061,642 12/1977 Fleckenstein et al. ............... 546/293
4,549,898 10/1985 Bohner et al. ........................... 71/92

Primary Examiner—John M. Ford

[57] ABSTRACT

This invention relates to herbicidal pyridine-sulfonylureas which are highly active as preemergence and postemergence herbicides.

2 Claims, No Drawings

HERBICIDAL PYRIDINESULFONYLUREAS

RELATED APPLICATIONS

This application is a continuation-in-part of my co-pending application, U.S. Ser. No. 39,491, filed Apr. 16, 1987 now abandoned, which in turn is a continuation-in-part of my application U.S. Ser. No. 939,428, filed Dec. 8, 1986, now abandoned.

BACKGROUND OF THE INVENTION

Pyridinesulfonylureas of the instant application show high activity as preemergence and post-emergence herbicides. In particular, safety to corn is demonstrated by the herbicides.

EP-A No. 13,480 discloses herbicidal sulfonamides of the formula

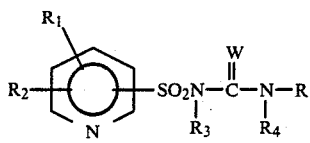

wherein
$R_1$ is H, Cl, Br, F, $C_1$–$C_4$ alkyl, $C_1$–$C_4$ alkoxy, $C_1$–$C_4$ alkylthio, $NO_2$ or $CO_2R_5$.

U.S. Pat. No. 4,435,206, issued Mar. 6, 1984 and U.S. Pat. No. 4,522,645, issued U.S. Pat. No. 4,522,645, discloses 2-pyridinesulfonylureas substituted in the 3-position by $R_1$, wherein $R_1$ is H, Cl, Br, F, $C_1$–$C_4$ alkyl, $C_1$–$C_4$ alkoxy, $C_1$–$C_4$ alkylthio, $NO_2$, $CF_3$, $CO_2R_5$ or $SO_2NR_6R_7$.

U.S. Pat. No. 4,339,267 discloses herbicidal sulfonamides of the formula

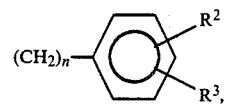

wherein
$R_4$ is H, Cl, Br, F, $C_1$–$C_4$ alkyl, $C_1$–$C_4$ alkoxy, $NO_2$, $CO_2R_6$ or $SR_{13}$.

EP-A No. 30,433 discloses herbicidal sulfonamides of the formula

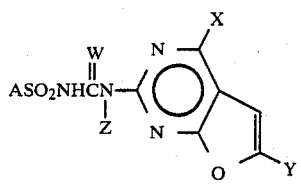

wherein
X is H;
$R_{14}$ is H or $CH_3$; and
$R_3$ is H, F, Cl, Br, $CH_3$, $OCH_3$, $NO_2$, $CO_2R_{11}$ or $S(O)_nR_{12}$.

U.S. Pat. No. 4,456,469 discloses herbicidal sulfonamides of the formula

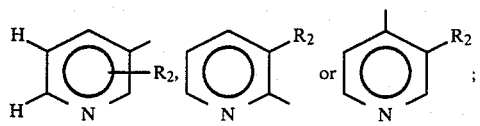

wherein
R is $C_1$–$C_6$ alkyl, $C_3$–$C_6$ alkenyl, $C_2$–$C_4$ alkoxy-alkyl, $C_5$–$C_6$ cycloalkyl, R'OCH$_2$CH$_2$OCH$_2$, R'OCH$_2$CH$_2$OCH$_2$CH$_2$,

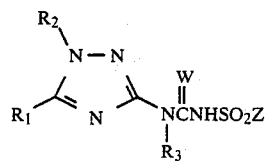

$CF_3$, $CF_3CH_2$, $HGLCCF_2$ or $HCF_2$; and
Z is H, F, Cl, Br, $CH_3$, $OCH_3$ or $SCH_3$.

U.S. Pat. No. 4,487,626 discloses herbicidal sulfonamides of the formula

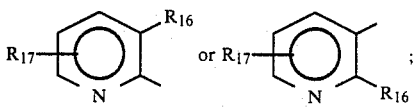

wherein
A is

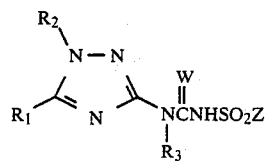

and
$R_2$ is H, F, Cl, Br, $C_1$–$C_4$ alkyl, $C_1$–$C_4$ alkoxy, $NO_2$, $CO_2R_{15}$, $S(O)_mR_{16}$, $SO_2NR_{18}R_{19}$ or $SO_2N(OCH_3)CH_3$.

U.S. Pat. No. 4,421,550 discloses herbicidal sulfonamides of the formula

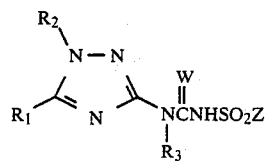

wherein
Z is

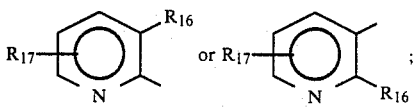

and $R_{16}$ is H, $C_1$–$C_4$ alkyl, $C_1$–$C_4$ alkoxy, F, Cl, Br, $CF_3$, $CO_2R_{20}$, $SO_2NR_{10}R_{11}$, $SO_2N(OCH_3)CH_3$ or $S(O)_nR_{13}$.

U.S. Pat. No. 4,496,392 discloses herbicidal sulfonamides of the formula

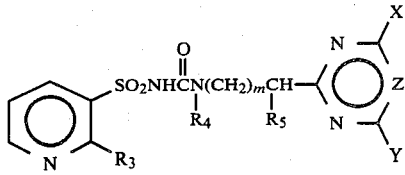

wherein
$R_3$ is Cl, $SO_2CH_3$ or $SO_2N(CH_3)_2$.

EP-A No. 84,224 discloses herbicidal sulfonamides of the formula

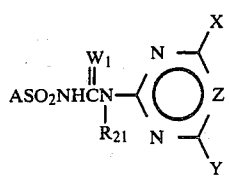

wherein
A is

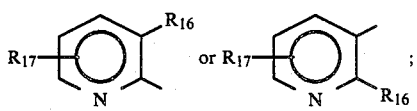

and
$R_{16}$ is H, $C_1$–$C_4$ alkyl, $C_1$–$C_4$ alkoxy, F, Cl, Br, $CF_3$, $CO_2R_9$, $SO_2NR_{10}R_{11}$, $SO_2N(OCH_3)CH_3$ or $S(O)_nR_{13}$.

EP-A No. 125,846 discloses herbicidal sulfonamides of the formula

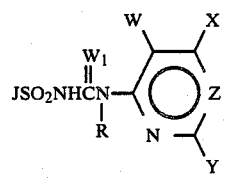

wherein
J is

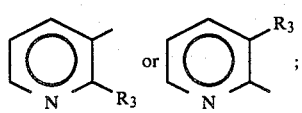

and
$R_3$ is Cl, $SO_2CH_3$, $SO_2N(CH_3)_2$, $OCH_3$, $NO_2$ or $N(CH_3)_2$.

EP-A No. 155,767 discloses herbicidal sulfonamides of the formula

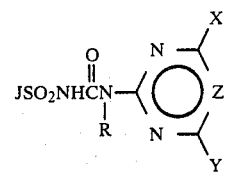

wherein
J is

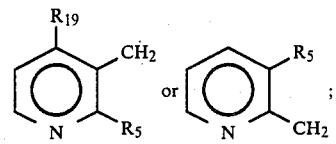

and
$R_5$ is H, $CH_3$, Cl, Br, $CO_2R_{15}$, $C(O)NR_{16}R_{17}$, $SO_2NR_{16}R_{17}$, $SO_2N(OCH_3)CH_3$, $SO_2R_{18}$ or $NO_2$.

EP-A No. 161,905 discloses herbicidal sulfonamides of the formula

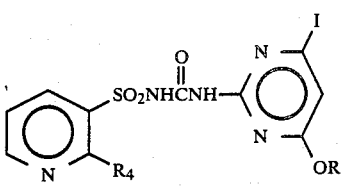

wherein
$R_4$ is $CH_3$, $CH_2CH_3$, $OCH_3$, $OCH_2CH_3$, F, Cl, Br, $SO_2NR_{16}R_{17}$, $SO_2N(OCH_3)CH_3$, $S(O)_nR_{19}$, $C_3$–$C_4$ alkenyloxy or $C_3$–$C_4$ alkynyloxy.

EP-A No. 164,269 discloses herbicidal sulfonamides of the formula

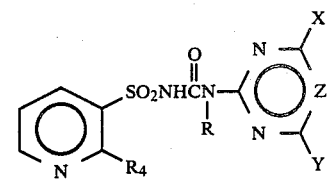

wherein
$R_4$ is $CH_3$, $CH_2CH_3$, $OCH_3$, $OCH_2CH_3$, F, Cl, Br, $SO_2NR_{11}R_{12}$, $SO_2N(OCH_3)CH_3$ or $S(O)_nR_{13}$.

EP-A No. 171,286 discloses herbicidal sulfonamides of the formula

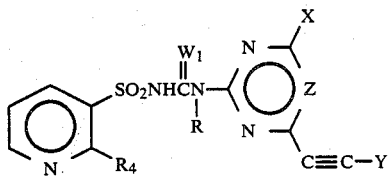

wherein
$R_4$ is $CH_3$, $CH_2CH_3$, $OCH_3$, $OCH_2CH_3$, F, Cl, Br, $SO_2NR_{18}R_{19}$, $SO_2N(OCH_3)CH_3$, $S(O)_nR_{21}$, $C_3$–$C_4$ alkenyloxy, $CH_2OCH_3$ or $CH_2OCH_2CH_3$.

South African Patent Application No. 83/4305, published Dec. 14, 1983, discloses herbicidal sulfonamides of the formula

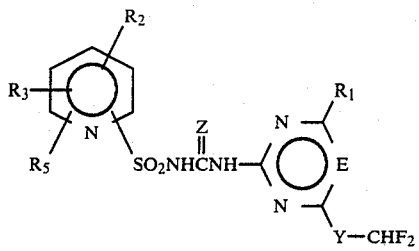

wherein
$R_2$ is H, $C_1-C_3$ alkyl, $C_1-C_3$ haloalkyl, halogen, $NO_2$, $C_1-C_3$ alkoxy, $C(W)R_8$, $SO_2NR_6R_7$, $S(O)_nC_1-C_3$ alkyl or $C(O)R_9$;
$R_3$ is H, halogen, $C_1-C_3$ alkyl, $OCH_3$, $NO_2$ or $CF_3$;
$R_5$ is H, $NO_2$, F, Cl, Br, $CH_3$, $CF_3$, $S(O)_nC_1-C_3$ alkyl, $C(O)C_1-C_4$ alkoxy or $C_1-C_3$ alkoxy;
Y is O or S.

South African Patent Application No. 83/6639, published Mar. 8, 1984, discloses herbicidal sulfonamides of the formula

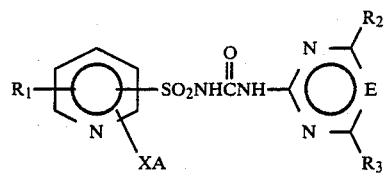

wherein
A is a $C_3-C_6$ alkynyl radical, a $C_1-C_6$ alkyl radical which is substituted by halogen, $C_1-C_4$ alkoxy, $C_1-C_4$ alkylthio, $C_1-C_4$ alkylsulfinyl, $C_1-C_4$ alkylsulfonyl, $C_1-C_4$ haloalkoxy, $C_1-C_4$ haloalkylthio, $C_1-C_4$ haloalkylsulfinyl or $C_1-C_4$ haloalkylsulfonyl, or is a $C_2-C_4$ alkenyl radical which is unsubstituted or substituted as for $C_1-C_6$ alkyl, or is a phenyl radical which is unsubstituted or substituted by halogen, cyano, nitro, $C_1-C_4$ alkyl, $C_1-C_4$ haloalkyl, an -X-$C_1-C_4$ alkyl, $C_1-C_4$ alkoxycarbonyl, amino, mono- or di($C_1-C_4$ alkyl)amino, carbamoyl, mono- di-($C_1-C_4$ alkyl)carbamoyl, sulfamyl, mono- or di-($C_1-C_4$ alkyl)sulfamoyl radical;
$R_1$ is hydrogen, halogen, $C_1-C_4$ alkyl, $C_1-C_4$ alkoxy, $C_1-C_4$ haloalkyl, $C_1-C_4$ haloalkoxy, $C_2-C_5$ alkoxyalkoxy, $C_1-C_5$ alkylthio, $C_1-C_5$ alkylsulfinyl or $C_1-C_5$ alkylsulfonyl; and
X is O, S, SO or $SO_2$.

U.S. Pat. No. 4,518,776 discloses a process for the preparation of herbicidal sulfonamides of the formula

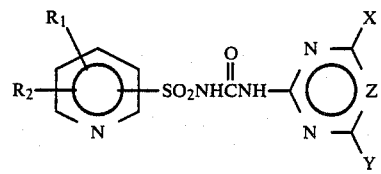

wherein
$R_1$ is $S(O)_nC_1-C_4$ alkyl or $SO_2$di-$C_1-C_4$ alkylamino; and $R_2$ is H, halogen, $CF_3$, $NO_2$, $C_1-C_4$ alkyl or $C_1-C_4$ alkoxy.

This patent generically discloses, but does not claim, compounds of the instant invention.

EP-A No. 101,670, published Feb. 29, 1984, discloses a process for the preparation of herbicidal sulfonamides of the formula

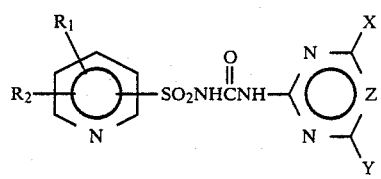

wherein
$R_1$ is Q-$C_1-C_4$ alkyl or $SO_2$-di-$C_1-C_4$ alkylamino;
Q is S or $S(O)_n$; and
$R_2$ is H, halogen, $CF_3$, $NO_2$, $C_1-C_4$ alkyl or $C_1-C_4$ alkoxy.

This application generically discloses compounds of the instant invention.

U.S. Pat. No. 4,521,597 discloses a process for the preparation of herbicidal sulfonamides of the formula

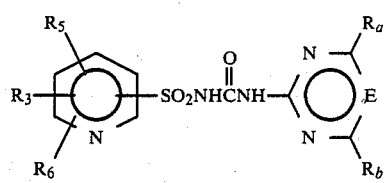

wherein
$R_3$ is H, F, Cl, Br, $NO_2$, $OCH_3$ or $CF_3$;
$R_5$ is $S(O)_mC_1-C_5$ alkyl or $SO_2NR_8R_9$; and
$R_6$ is H, F, $CH_3$ or $OCH_3$.

This patent generically discloses, but does not claim, compounds of the instant invention.

EP-A No. 184,385, published June 11, 1986, discloses the following compound for selective weed control in tomatoes and turf.

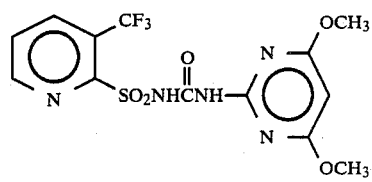

U.S. Ser. No. 874,307 discloses o-alkylcarbonylpyridinesulfonylureas.

U.S. Ser. No. 943,137 discloses o-substitutedalkyl-pyridinesulfonylureas.

SUMMARY OF THE INVENTION

This application pertains to novel compounds of Formula I, agriculturally suitable compositions containing them and their method-of-use as preemergent and/or postemergent herbicides or plant growth regulants.

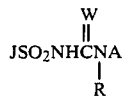

wherein
J is

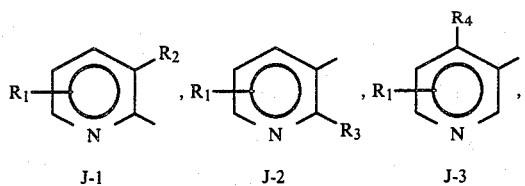

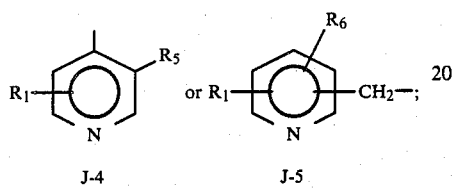

R is H or CH₃;
W is O or S;
$R_1$ is H, $C_1$-$C_3$ alkyl, $C_1$-$C_3$ haloalkyl, halogen, $NO_2$, $C_1$-$C_3$ alkoxy, $C_1$-$C_3$ alkylthio or CN;
$R_2$ is $C_1$-$C_4$ alkylsulfinyl, $C_1$-$C_4$ alkylsulfonyl, $C_3$-$C_5$ cycloalkylthio, $C_3$-$C_5$ cycloalkylsulfinyl, $C_3$-$C_5$ cycloalkylsulfonyl, $OSO_2R_8$, $SO_2OR_8$, $N_3$, $P(W_1)(OC_1$-$C_2$ alkyl$)_2$, CN, $CH_2F$, $CF_2H$, $CH_2Cl$, $CCl_2H$ or $C_2$-$C_4$ haloalkyl;
$R_3$ is $C_1$-$C_4$ alkylsulfinyl, $C_3$-$C_5$ cycloalkylthio, $C_3$-$C_5$ cycloalkylsulfinyl, $C_3$-$C_4$ cycloalkylsulfonyl, $OSO_2R_8$, $SO_2OR_8$, $N_3$, $P(W_1)(OC_1$-$C_2$ alkyl$)_2$, CN or $C_1$-$C_4$ haloalkyl;
$R_4$ is $C_1$-$C_4$ alkylsulfinyl, $C_3$-$C_5$ cycloalkylthio, $C_3$-$C_5$ cycloalkylsulfinyl, $C_3$-$C_4$ cycloalkylsulfonyl, $OSO_2R_8$, $SO_2OR_8$, $N_3$, $P(W_1)(OC_1$-$C_2$ alkyl$)_2$, CN or $C_1$-$C_4$ haloalkyl;
$R_5$ is $C_1$-$C_4$ alkylsulfinyl, $C_1$-$C_4$ alkylsulfonyl, $C_3$-$C_5$ cycloalkylthio, $C_3$-$C_5$ cycloalkylsulfinyl, $C_3$-$C_5$ cycloalkylsulfonyl, $OSO_2R_8$, $SO_2OR_8$, $N_3$, $P(W_1)(OC_1$-$C_2$ alkyl$)_2$, CN or $C_1$-$C_4$ haloalkyl;
$R_6$ is $C_1$-$C_4$ alkylthio, $C_1$-$C_4$ alkylsulfinyl, $C_1$-$C_4$ haloalkylthio, $C_1$-$C_4$ haloalkylsulfinyl, $C_1$-$C_4$ haloalkylsulfonyl, $C_3$-$C_4$ alkenylthio, $C_3$-$C_4$ alkenylsulfinyl, $C_3$-$C_4$ alkenylsulfonyl, $C_3$-$C_4$ alkynylthio, $C_3$-$C_4$ alkynylsulfinyl, $C_3$-$C_4$ alkynylsulfonyl, $C_3$-$C_5$ cycloalkylthio, $C_3$-$C_5$ cycloalkylsulfinyl, $C_3$-$C_5$ cycloalkylsulfonyl, $OSO_2R_8$, $SO_2OR_8$, $N_3$, $P(W_1)(OC_1$-$C_2$ alkyl$)_2$, CN or $C_1$-$C_4$ haloalkyl;
$R_8$ is $C_1$-$C_4$ alkyl, $C_1$-$C_4$ haloalkyl, $C_3$-$C_4$ alkenyl, $C_3$-$C_4$ alkynyl, $C_2$-$C_4$ alkoxyalkyl or cyclopropyl;
$W_1$ is O or S;
A is

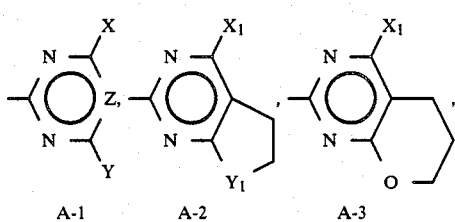

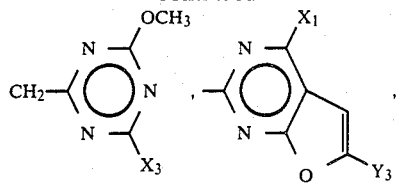

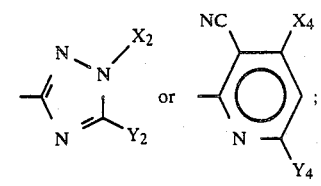

X is H, $C_1$-$C_4$ alkyl, $C_1$-$C_4$ alkoxy, $C_2$-$C_4$ haloalkoxy, $C_1$-$C_4$ haloalkyl, $C_2$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;
Y is H, $C_1$-$C_4$ alkyl, $C_1$-$C_4$ alkoxy, $C_2$-$C_4$ haloalkoxy, $C_2$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido,

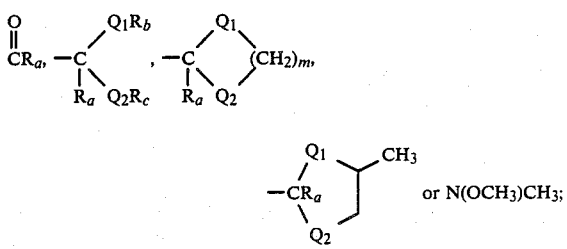

m is 2 or 3;
$Q_1$ and $Q_2$ are independently O or S;
$R_a$ is H or $C_1$-$C_3$ alkyl;
$R_b$ and $R_c$ are independently $C_1$-$C_3$ alkyl;
Z is CH, N, $CCH_3$, $CC_2H_5$, CCl or CBr;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl;
$Y_4$ is $CH_3$, $OCH_3$, $OC_2H_5$ or Cl;
and their agriculturally suitable salts; provided that
(1) when X is halogen, then Z is CH and Y is $OCH_3$, $OC_2H_5$, $NH_2$, $NHCH_3$, $N(CH_3)_2$ or $N(OCH_3)CH_3$;
(2) When W is S, then R is H, A, is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2C$-$H_2OCH_3$, $CH(OCH_3)_2$ or

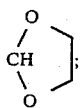

(3) when the total number of carbon atoms of X and Y is greater than four, then the combined number of carbons of $R_1$, $R_2$, $R_3$, $R_4$, $R_5$ or $R_6$ is less than or equal to six;

(4) when J is J-1 and $R_2$ is $C_1$-$C_4$ alkylsulfonyl or when J is $J_2$ and $R_3$ is $CF_3$, then Y is other than $C_2$-$C_5$ alkylthioalkyl, $C_2$-$C_5$ alkylsulfinylalkyl, $C_2$-$C_5$ alkylsulfonylalkyl,

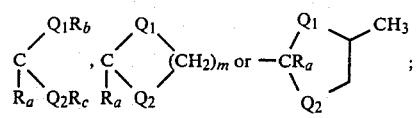

(5) when J is $J_2$ or $J_3$ and $R_3$ or $R_4$ is $C_1$-$C_4$ alkylsulfinyl, then X and Y are other than $NH_2$ or $NHCH_3$;

(6) when J is J-2 and $R_3$ is $C_1$-$C_4$ alkylsulfinyl, then X and Y are other than $C_2$-$C_4$ haloalkoxy;

(7) $X_4$ and $Y_4$ are not simultaneously Cl;

(8) when J is J-1, J-2, J-3 or J-4 and A is A-5, then $R_1$ is other than H;

(9) when J is J-1 or J-2, then A is other than A-6;

(10) when J is J-1 and A is A-7, then $R_2$ is other than $C_1$-$C_4$ alkylsulfonyl.

In the above definitions, the term "alkyl", used either alone or in compound words such as "alkylthio" or "haloalkyl", denotes straight chain or branched alkyl, e.g. methyl, ethyl n-propyl, isopropyl or the different butyl isomers.

Alkoxy denotes methoxy, ethoxy, n-propyloxy or isopropyloxy.

Alkenyl denotes straight chain or branched alkenes, e.g. 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes methylsulfonyl, ethylsulfonyl and the different propylsulfonyl and butylsulfonyl isomers.

Cycloalkyl denotes cyclopropyl, cyclobutyl and cyclopentyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms which may be the same or different. Examples of haloalkyl include $CH_2CH_2F$, $CF_2CF_3$ and $CH_2CHFCl$. Similarly, this definition applies to haloalkoxy and haloalkylthio.

The total number of carbon atoms in a substituent group is indicated by the $C_i$-$C_j$ prefix where i and j are numbers from 1 to 5. For example, $C_1$-$C_3$ alkylsulfonyl would designate methylsulfonyl through propylsulfonyl, $C_2$ alkoxyalkyl would designate $OCH_2OCH_3$.

PREFERRED COMPOUNDS

Preferred for reasons of increased ease of synthesis and/or greater herbicidal efficacy are:

1. Compounds of Formula I where
   X is $C_1$-$C_2$ alkyl, $C_1$-$C_2$ alkoxy, Cl, F, Br, I, $CH_2F$, $CF_3$, $OCH_2CH_2F$, $OCH_2CHF_2$, $OCH_2CF_3$, $CH_2Cl$ or $CH_2Br$;
   Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$,

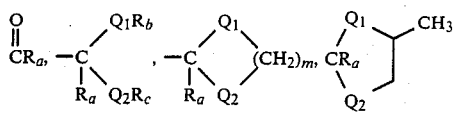

$CH_2SCH_3$, cyclopropyl, $C\equiv CH$ or $C\equiv CCH_3$; and
   Z is CH or N.

2. Compounds of Preferred 1 where
   W is O;
   $R_1$ is H, $CH_3$, $C_1$ haloalkyl, halogen or $OCH_3$;
   $R_2$ is $C_1$-$C_4$ alkylsulfinyl, $C_1$-$C_4$ alkylsulfonyl, $OSO_2R_8$, $SO_2OR_8$, $N_3$, $P(W_1)(OC_1$-$C_2$ alkyl$)_2$, CN, $CHF_2$, $CF_2H$, $CH_2Cl$, $CCl_2H$ or $C_2$-$C_4$ haloalkyl;
   $R_3$ is $C_1$-$C_4$ alkylsulfinyl, $OSO_2R_8$, $SO_2OR_8$, $N_3$, $P(W_1)(OC_1$-$C_2$ alkyl$)_2$, CN or $C_1$-$C_4$ haloalkyl;
   $R_4$ is $C_1$-$C_4$ alkylsulfinyl, $OSO_2R_8$, $SO_2OR_8$, $N_3$, $P(W_1)(OC_1$-$C_2$ alkyl$)_2$, CN or $C_1$-$C_4$ haloalkyl;
   $R_5$ is $C_1$-$C_4$ alkylsulfinyl, $C_1$-$C_4$ alkylsulfonyl, $OSO_2R_8$, $SO_2OR_8$, $N_3$, $P(W_1)(OC_1$-$C_2$ alkyl$)_2$, CN or $C_1$-$C_4$ haloalkyl;
   $R_6$ is $C_1$-$C_4$ alkylthio, $C_1$-$C_4$ alkylsulfinyl, $C_1$-$C_4$ haloalkylthio, $C_1$-$C_4$ haloalkylsulfinyl, $C_1$-$C_4$ haloalkylsulfonyl, $C_3$-$C_4$ alkenylthio, $C_3$-$C_4$ alkenylsulfinyl, $C_3$-$C_4$ alkenylsulfonyl, $C_3$-$C_4$ alkynylthio, $C_3$-$C_4$ alkynylsulfinyl, $C_3$-$C_4$ alkynylsulfonyl, $OSO_2R_8$, $SO_2OR_8$, $N_3$, $P(W_1)(OC_1$-$C_2$ alkyl$)_2$, CN or $C_1$-$C_4$ haloalkyl; and
   $R_8$ is $C_1$-$C_4$ alkyl, $C_1$-$C_4$ haloalkyl, $C_3$-$C_4$ alkenyl, $C_3$-$C_4$ alkynyl, $C_2$-$C_4$ alkoxyalkyl or cyclopropyl.

3. Compounds of Preferred 2 where J is J-1.
4. Compounds of Preferred 2 where J is J-2.
5. Compounds of Preferred 2 where J is J-3.
6. Compounds of Preferred 2 where J is J-4.
7. Compounds of Preferred 2 where J is J-5.
8. Compounds of Preferred 3 where
   $R_8$ is $C_1$-$C_3$ alkyl, allyl, propargyl or cyclopropyl.
9. Compounds of Preferred 8 where
   A is A-1;
   X is $CH_3$, $OCH_3$, $OCH_2CH_3$, Cl or $OCH_2CF_3$; and
   Y is $CH_3$, $OCH_3$, $CH_2CH_3$, $CH_2OCH_3$, $NHCH_3$ or $CH(OCH_3)_2$.
10. Compounds of Preferred 9 where Z is CH.
11. Compounds of Preferred 9 where Z is N.
12. Compounds of Preferred 4 where
    $R_8$ is $C_1$-$C_3$ alkyl, allyl, propargyl or cyclopropyl.
13. Compounds of Preferred 12 where
    A is A-1;
    X is $CH_3$, $OCH_3$, $OCH_2CH_3$, Cl or $OCH_2CF_3$; and
    Y is $CH_3$, $OCH_3$, $CH_2CH_3$, $CH_2OCH_3$, $NHCH_3$ or $CH(OCH_3)_2$.
14. Compounds of Preferred 13 where Z is CH.
15. Compounds of Preferred 13 where Z is N.
16. Compounds of Preferred 5 where
    $R_8$ is $C_1$-$C_3$ alkyl, allyl, propargyl or cyclopropyl.
17. Compounds of Preferred 16 where
    A is A-1;
    X is $CH_3$, $OCH_3$, $OCH_2CH_3$, Cl or $OCH_2CF_3$; and Y is $CH_3$, $OCH_3$, $CH_2CH_3$, $CH_2OCH_3$, $NHCH_3$ or $CH(OCH_3)_2$.
18. Compounds of Preferred 17 where Z is CH.
19. Compounds of Preferred 17 where Z is N.
20. Compounds of Preferred 6 where
    $R_8$ is $C_1$-$C_3$ alkyl, allyl, propargyl or cyclopropyl.
21. Compounds of Preferred 20 where
    A is A-1;
    X is $CH_3$, $OCH_3$, $OCH_2CH_3$, Cl or $OCH_2CF_3$; and
    Y is $CH_3$, $OCH_3$, $CH_2CH_3$, $CH_2OCH_3$, $NHCH_3$ or $CH(OCH_3)_2$.
22. Compounds of Preferred 21 where Z is CH.
22. Compounds of Preferred 21 where Z is N.
24. Compounds of Preferred 7 where
    $R_6$ is $C_1$-$C_2$ alkylthio, $C_1$-$C_2$ alkylsulfinyl, $C_1$-$C_2$ haloalkylthio, $C_1$-$C_2$ haloalkylsulfinyl, or $C_1$-$C_2$ haloalkylsulfonyl; and
    $R_8$ is $C_1$-$C_3$ alkyl, allyl, propargyl or cyclopropyl.
25. Compounds of Preferred 24 where
    A is A-1;
    X is $CH_3$, $OCH_3$, $OCH_2CH_3$, Cl or $OCH_2CF_3$; and
    Y is $CH_3$, $OCH_3$, $CH_2CH_3$, $CH_2OCH_3$, $NHCH_3$ or $CH(OCH_3)_2$.
26. Compounds of Preferred 25 where Z is CH.
27. Compounds of Preferred 25 where Z is N.
28. Compounds of Preferred 1 where
    J is J-1;
    A is A-1;
    Z is CH;
    W is O;
    $R_2$ is $C_1$-$C_4$ alkylsulfinyl or $C_1$-$C_4$ alkylsulfonyl; and
    $R_1$ is H, $C_1$-$C_2$ alkyl, $C_1$ haloalkyl, $C_1$-$C_2$ alkoxy or $C_1$-$C_2$ thioalkyl.
29. Compounds of Preferred 28 where
    $R_1$ is H;
    $R_2$ is $C_1$-$C_4$ alkylsulfonyl;
    X is $OCH_3$; and
    Y is $OCH_3$.

Specifically Preferred for reasons of greatest ease of synthesis and/or greatest herbicidal efficacy are:
N-[(4,6-dimethoxypyrimidin-2-yl)aminocarbonyl]-3-(1-propylsulfonyl)-2-pyridinesulfonamide, m.p. 168°–170° C.;
N-[(4,6-dimethoxypyrimidin-2-yl)aminocarbonyl]-3-(1-propylsulfinyl)-2-pyridinesulfonamide, m.p. 111°–115° C.;
N-[(4,6-dimethoxypyrimidin-2-yl)aminocarbonyl]-3-(ethylsulfonyl)-2-pyridinesulfonamide; and
N-[(4,6-dimethoxypyrimidin-2-yl)aminocarbonyl]-3-(methylsulfonyloxy)-2-pyridinesulfonamide.

DETAILED DESCRIPTION OF THE INVENTION

Synthesis

Compounds of Formula I can be synthesized either by one or more of the methods described in U.S. Pat. No. 4,456,469, or by the reaction of sulfonamides II with the phenyl ester of the appropriate carbamic acid III in the presence of an equimolar quantity of a tertiary amine base such as 1,8-diazabicyclo[5.4.0]undec-7-ene (DBU) as shown in Equation 1.

Equation 1

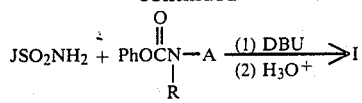

wherein
J, R, and A are as previously defined.

The reaction shown in Equation 1 is best carried out at 25° C. in a solvent such as dioxane or acetonitrile for 1–2 hours under an inert atmosphere as described in European Patent Application No. 70,804 (published Jan. 26, 1983). The desired products of Formula I can be conveniently isolated by acidifying the reaction solution with aqueous hydrochloric acid. Alternatively, the aqueous layer can be extracted with a solvent such as methylene chloride or ethyl acetate. Drying and evaporation of the solvent affords the desired products. The phenyl carbamates can be synthesized by treatment of the corresponding heterocyclic amines of Formula A-NHR with diphenyl carbonate or phenyl chloroformate in the presence of a base such as sodium hydride, pyridine, or potassium carbonate with a catalytic amount of 4-dimethylaminopyridine. The mixture is stirred at temperatures between 25° and 65° C. in a suitable solvent such as tetrahydrofuran for 12–36 hours.

The required sulfonamides of Formula II can be synthesized by either one of the methods shown below in Equations 2 and 3.

Equations 2 depicts the reaction of sulfonyl chlorides of Formula IV with ammonia to give sulfonamides of Formula II.

Equation 2

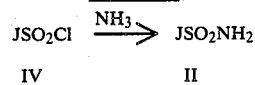

wherein
J is as previously defined.

The amination of Equation 2 is conveniently effected by adding at least two molar equivalents of either anhydrous ammonia or concentrated ammonium hydroxide to a solution of the sulfonyl chloride IV in a suitable solvent such as diethyl ether, tetrahydrofuran or methylene chloride at temperatures between −30° and 25° C. The desired sulfonamides of Formula II are isolated either by filtration, in which case the by-product ammonium chloride is removed by washing with water, or extraction into a suitable organic solvent such as methylene chloride or ethyl acetate. Drying and evaporation of the solvent then affords the products II which are usually sufficiently pure to be carried directly on to the next step.

Sulfonamides of Formula II can also be prepared as shown in Equation 3 by treatment of the corresponding N-t-butylsulfonamides VI with an appropriate acid such as trifluoroacetic (TFA), polyphosphoric (PPA), or p-toluenesulfonic acid (p-TSA).

Equation 3

-continued

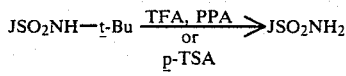

VI  II wherein
J is as previously defined.

The reaction of Equation 3 is conveniently carried out by stirring a solution of the compound of Formula VI in excess trifluoroacetic acid (approximately 0.3M) at about 25° C. for 1–72 hours. The desired sulfonamides of Formula II are then isolated by removal of the volatiles in vacuo and crystallization from a suitable solvent such as diethyl ether, 1-chlorobutane, or ethyl acetate. Alternatively, the N-t-butylsulfonamides of Formula VI can be treated with a catalytic amount of p-toluenesulfonic acid monohydrate in a solvent such as toluene or xylenes at reflux temperature for 1–6 hours. The desired products are then isolated in a manner analogous to the one described above. For use of polyphosphoric acid in the deprotection of N-t-butylsulfonamides, see J. G. Lombardino, *J. Org. Chem.*, 36, 1843 (1971); for use of trifluoroacetic acid, see J. D. Catt and W. L. Matier, *J. Org. Chem.*, 38, 1974 (1973).

Sulfonamides of Formula VI can be prepared by the reaction of sulfonyl chlorides of Formula IV with excess t-butyl amine as shown in Equation 4.

Equation 4

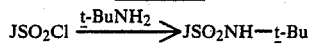

IV  VI wherein
J is as previously defined.

Sulfonyl chlorides of Formula IV can be prepared according to the procedures described in U.S. Pat. No. 4,456,469. Alternatively, the procedures of South African Patent Application No. 84/8844 may be utilized which describe the conversion of mercapto or arylmethylthio compounds to sulfonyl chlorides via treatment with hypochlorite solution.

Sulfonyl chlorides of Formula IVa may also be prepared via metallation of 2-fluoropyridine derivatives with lithium diisopropyl amide (LDA) according to the procedure of T. Gungor, F. Marsais and G. Queguiner, *J. Organomet. Chem.*, 1981, 215, 139–150, followed by treatment with sulfur dioxide and N-chlorosuccinimide (NCS) as shown in Equation 5.

Equation 5

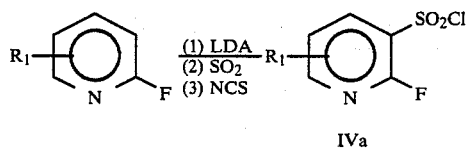

IVa wherein
R$_1$ is as previously defined.

Sulfonyl chlorides of Formula IVb can be prepared from compounds of Formula VII as shown in Equation 6 and described in U.S. Pat. No. 4,420,325.

Equation 6

-continued

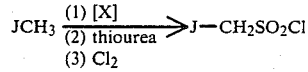

VII  IVb wherein
J is as previously defined; and
[X] is a suitable halogenating reagent which would be obvious to one skilled in the art.

The sulfides of Formula VIII can be prepared by the reaction of a halo pyridine compound of Formula IX with an appropriate mercaptan in the presence of a base as described in U.S. Pat. No. 4,456,469 and shown in Equation 7.

Equation 7

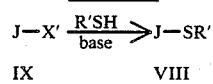

IX  VIII wherein
X' is F, Cl, or Br; and
R' is C$_1$–C$_4$ alkyl or benzyl.

The sulfides of Formula VIIIa can be prepared by metallation of the pyridine compound of Formula X with two equivalents of a strong base such as n-butyllithium or lithium diisopropylamide (LDA) as described by P. Breant, F. Marsais, and G. Queguiner, *Synthesis*, 1983, 822–824, followed by treatment with the appropriate disulfide as shown in Equation 8.

Equation 8

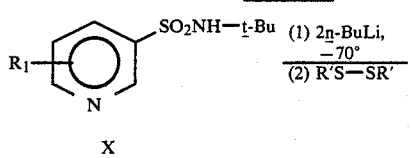

X

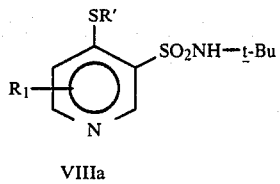

VIIIa wherein
R' is C$_1$–C$_4$ alkyl, C$_3$–C$_5$ cycloalkyl or benzyl; and
R$_1$ is as previously defined.

In an analogous manner, sulfides of Formula VIIIb can be prepared as shown in Equation 9.

Equation 9

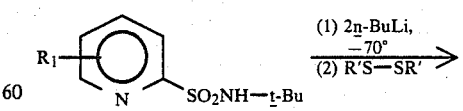

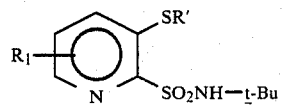

VIIIb wherein
R' is $C_1$–$C_4$ alkyl, $C_3$–$C_5$ cycloalkyl, or benzyl; and
$R_1$ is as previously defined.

Sulfides of Formula VIIIc can be prepared by the metallation of a 2-fluoropyridine derivative as described previously and again followed by treatment with an appropriate disulfide as shown in Equation 10.

Equation 10

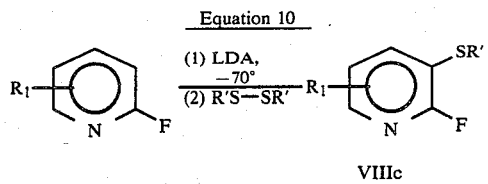

VIIIc wherein
R' is $C_1$–$C_4$ alkyl, $C_3$–$C_5$ cycloalkyl, or benzyl; and
$R_1$ is as previously defined.

The sulfones and sulfoxides of General Formula XI can be prepared from the corresponding sulfides of Formula VIIId by any one of the numerous oxidation reagents [O] known in the art such as hydrogen peroxide or peracids, as shown in Equation 11.

Equation 11

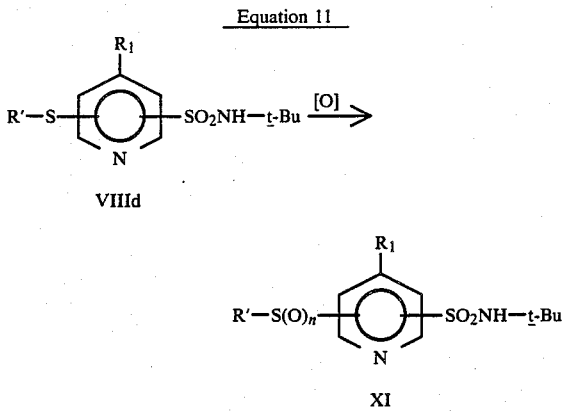

XI wherein
$R_1$ is as previously defined;
R' is $C_1$–$C_4$ alkyl or $C_3$–$C_5$ cycloalkyl; and
n is 1 or 2.

The chloropyridine of Formula IXa can be prepared by diazotization of 3-amino-chloropyridine followed by displacement with cuprous cyanide as shown in Equation 12. The diazonium group can also be replaced by other groups such as $SO_2Cl$ and $N_3$ by those skilled in the art via methods known in the literature.

Equation 12

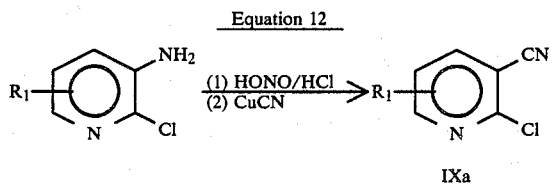

IXa wherein
$R_1$ is as previously defined.

The sulfides of General Formula VIIIf can be prepared as shown in Equation 13. Alkylation of a 3-hydroxy-2-mercaptopyridine derivative with alkyl halides utilizing a variety of bases such as potassium carbonate or potassium t-butoxide afforded the sulfides of Formula VIIIe which were then treated with the appropriate sulfonyl chlorides in the presence of an acid acceptor such as triethylamine to afford sulfides of Formula VIIIf.

Equation 13

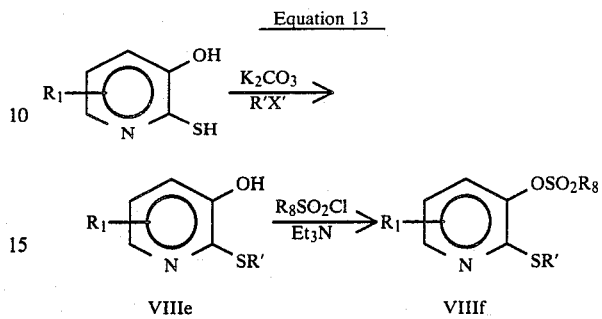

VIIIe           VIIIf

Wherein
R' is $C_1$–$C_4$ alkyl or benzyl;
X' is Cl, Br, or I; and
$R_1$ and $R_8$ are as previously defined.

A choice by one skilled in the art of he appropriate methods for preparing compounds of Formula I must take into account the nature of the substituents $R_1$ through $R_8$ and their chemical compatibility with the reaction conditions of Equations 1 through 13.

The heterocyclic amines of Formula A-NHR in Equation 1 above can be prepared by methods known in the literature, or simple modifications thereof, by those skilled in the art. For instance, EP-A No. 84,224 (published July 27, 1983) and W. Braker et al., *J. Chem. Soc.* 69, 3072 (1947) describes methods for preparing aminopyridines and triazines substituted by acetal groups such as dialkoxymethyl or 1,3-dioxolan-2-yl, among other groups. Also, for example, South African patent application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, or $OCF_2H$, among otther groups. Soutth African patent application No. 83/7434 (published Oct. 5, 1983) describes methos for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2,3-d]pyrimidine-2-amines, the cyclopenta[d]pyrimidine-2-amines (A is A-2) and the 6,7-dihydro-5H-pyrano[2,3-d]pyrimidin-2-amines (A is A-3) can be prepared as described in EP-A No. (15,683. The furo[2,3-d]pyrimidin-2-amines (A is A-4) are described in EP-A No. 46,677.

Compounds of Formula A-NHR where A is A-5 are described in EP-A No. 73,562. Compounds where A is A-6 are described in EP-A No. 94,260.

In addition, general methods for preparing aminopyrimidines and triazines have been reviewed in the following publications:

The Chemistry of Heterocyclic Compounds", a series published by Interscience Publishers, Inc., New York and London;

"Pyrimidines", Vol. 16 of the same series by D. J. Brown;

"s-Triazines and Derivatives", Vol. 13 of the same series by E. M. Smolin and L. Rappoport; and F. C. Schaefer, U.S. Pat. No. 3,154,547 and K. R. Huffman and F. C. Schaefer, *J. Org. Chem.*, 28, 1812 (1963), which describes the synthesis of triazines.

Preparation in view of the above would be obvious to one skilled in the art. Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Temperatures are reported in degrees Celsius; abbreviations for nuclear magnetic resonance (NMR) are: s=singlet, d=doublet, t=triplet, m=multiplet, and peak positions are reported as parts per million downfield from internal tetramethylsilane. Infrared (IR) peak positions are given in reciprocal centimeters (cm$^{-1}$).

EXAMPLE 1

Preparation of 2-Fluoro-3-(propylthio)pyridine

To a stirred solution of 59 ml (0.113 mol) of 1.9 molar lithium diisopropyl amide (in hexanes) in 150 mls dry tetrahydrofuran cooled to −70° under nitrogen was added dropwise a solution of 10.0 g of 2-fluoropyridine (0.103 mol) in 30 mls dry tetrahydrofuran such that the temperature was maintained below −65°. The solution was stirred at −70° for 4 hours and a solution 17 g of n-propyldisulfide (0.113 mol ) in 45 mls dry tetrahydrofuran was added dropwise while maintaining the temperature below −65°. After stirring another hour at −70°, the solution was poured into water and extracted with ether. The combined organic phases were washed with brine, dried over magnesium sulfate, and evaporated to afford 14.5 g (82%) of a red oil: NMR (CDCl$_3$, 200 MHz), 1.0 (3H, m), 1.7 (2H, m), 2.9 (2H, m), 7.1 (1H, m), 7.7 (1H, m), 8.0 (1H, m); IR (neat) 1585, 1560, 1410, 1245 cm$^{-1}$.

EXAMPLE 2

Preparation of 2-(Phenylmethylthio)-3-(propylthio)pyridine

To a stirred suspension of 0.62 g (0.013 mol) of 50% sodium hydride (in mineral oil), which had been washed withh hexanes, in 20 mls dry dimethylformamide cooled to −5° under nitrogen was added dropwise 1.6 g (0.013 mol) benzyl mercaptan such that the temperature was maintained below 5°. The suspension was stirred at room temperature for 1 hour, cooled to 0°, and a solution of 2.0 g (0.012 mol) of the product from Example 1 was added dropwise while maintaining the temperature between 0° and 5°. After warming to room temperature, the solution was poured into water and extracted with ether. The combined organic layers were washed with water and with brine, dried over magnesium sulfate, and evaporatd to an oil which was purified by flash chromatography to afford 0.9 g (27%) oil: NMR (CDCl$_3$, 200 MHz), 1.02 (3H, t J=7 Hz), 1.6 (2H, m), 2.9 (2H, t, J=7 Hz), 4.45 (2H, s), 6.9–7.6 (7H, m), 8.3 (1H, m); IR (neat) 1560, 1370 cm$^{-1}$.

EXAMPLE 3

Preparation of N-(1,1-Dimethylethyl)-3-(propylsulfinyl)-2-pyridinesulfonamide

To a vigorously stirred mixture of 0.5 g (0.0018 mol) of the product from Example 2 in 9 mls methylene chloride and 4 mls water cooled to 0° was added 0.7 mls (0.008 mol) concentrated hydrochloric acid followed by the dropwise addition of 8.9 mls (0.006 mol) of a 5% sodium hypochlorite solution such that the temperature was maintained between 0° and 5°. After the mixture was stirred for an additional 30 minutes at 0° the reaction was poured into water and extracted with methylene chloride. The combined organic layers were washed with brine, dried over magnesium sulfate, and filtered. The filtrate was stirred and cooled to −70° under nitrogen and 0.53 g (0.0072 mol) of t-butyl amine was added dropwise and the mixture was allowed to warm to room temperature. The reaction was poured into water and extracted with methylene chloride. The organic layers were combined and washed with brine, dried over magnesium sulfate, and evaporated to a mixture which was purified by flash chromatography to afford 0.4 g (69%) white solid: m.p. 138°–140°; NMR (CDCl$_3$, 200 MHz) 1.09 (3H, m), 1.7 (1H, m), 2.0 (1H, m), 2.8 (1H, m), 3.3 (1H, m), 5.2 (NH), 7.7 (1H, m), 8.6 (1H, m), 8.8 (1H, m); IR (nujol) 3400, 1375, 1325, 1160, 1065, 1015 cm$^{-1}$.

EXAMPLE 4

Preparation of 3-(Propylsulfonyl)-2-pyridinesulfonamide

To a stirred solution of 8.8 g (0.029 mol) of the product from Example 3 in 400 mls methylene chloride cooled to −5°, under nitrogen, was added 6.6 g (0.038 mol) of 3-chloroperbenzoic acid and stirred at room temperature for 20 hours. The reaction mixture was poured into water and extracted with methylene chloride. The orgnic layers were combined and washed with saturated sodium bisulfite and brine, dried over magnesium sulfate, and evaporated to a solid mixture which was washed with hexanes to afford a white solid. The solid was dissolved and stirred in 150 mls trifluoroacetic acid for 72 hours. The solution was evaporated and triturated with ether to afford 5.3 g (46%) white solid: m.p. 153°–157°; NMR (CDCl$_3$, 200 MHz) 1.06 (3H, t, J=7 Hz), 1.8 (2H, m), 3.7 (2H, m) 5.8 (NH$_2$), 7.8 (1H, m), 8.6 (1H, m), 8.95 (1H, m); IR (nujol) 3390, 3180, 1360, 1310, 1175, 1150 cm$^{-1}$.

EXAMPLE 5

Preparation of
N-[(4,6-Dimethoxypyrimidin-2-yl)aminocarbonyl]-3-(propylsulfonyl)-2-pyridinesulfonamide To a stirred suspension of 0.4 g (0.0015 mol) of the product from Example 4 and 0.63 g (0.0023 mol) of phenyl (4,6-dimethoxypyrimidin-2-yl)carbamate in 4 mls acetonitrile was added 0.35 g (0.0023 mol) of 1,8-diazabicyclo[5.4.0]undec-7-ene and stirred for 30 minutes. The solution was diluted with water and acidified with 1 normal hydrochloric acid. The resulting precipitate was collected and washed with water and ether to afford 0.45 g (67%) white solid: m.p. 168°–170°; NMR ($CDCl_3$, 200 MHz), 1.07 (3H, t, J=7 Hz), 1.85 (2H, m), 3.7 (2H, m), 3.97 (6H, s), 5.8 (1H, s), 7.26 (NH), 7.8 (1H, m), 8.6 (1H, m), 8.9 (1H, m), 12.9 (NH); IR (nujol) 3320, 1740, 1610, 1580, 1375, 1195, 1170 $cm^{-1}$.

EXAMPLE 6

Preparation of
N-(1,1-Dimethylethyl)-2-fluoro-3-pyridinesulfonamide

To a stirred solution of 344 mls (0.74 mol) of 2.15 molar lithium diisopropyl amide (in hexanes) in 1.8 liters dry tetrahydrofuran cooled to −70° under nitrogen was added dropwise a solution of 65 g (0.67 mol) of 2-fluoropyridine in 300 mls dry tetrahydrofuran such that the temperature was maintained below −65°. After the solution was stirred 4 hours at −70°, 73.5 g (1.15 mol) of sulfur dioxide was added dropwise while the temperature was maintained below −65°. The suspension was stirred 1 hour at −70° and allowed to warm to room temperature. The reaction was diluted with ether and the precipitate was collected and washed with ether under a nitrogen atmosphere. The solid was stirred and dissolved in 550 mls acetic acid. 89 g (0.67 mol) of N-chlorosuccinimide was added portionwise while the temperature was maintained below 20°. After stirring an additional 30 minutes at room temperature, the reaction was evaporated, diluted with water, and extracted with ether. The combined organic layers were washed with saturated sodium bicarbonate solution until gas evolution ceased, dried over magnesium sulfate, and evaporated to a dark liquid which was dissolved in 900 mls methylene chloride and cooled to 0° under nitrogen. 244 g (3.3 mol) of t-butyl amine was added dropwise while the temperature was maintained below 10°. The reaction was stirred at room temperature for 20 hours and poured into water, acidified with 1 normal hydrochloric acid, and extracted with methylene chloride. The combined organic layers were washed with brine, dried over magnesium sulfate and evaporated to a dark liquid which was purified by flash chromatography to afford 56.3 g (36%) white solid: m.p. 95°–97°; NMR ($CDCl_3$, 200 MHz), 1.25 (9H, s), 4.9 (NH), 7.3–7.4 (1H, m), 8.3–8.5 (2H, m); IR (nujol) 3290, 1590, 1570, 1320, 1160 $cm^{-1}$.

EXAMPLE 7

Preparation of 3-ethylthio-2-fluoropyridine

Utilizing the procedure of Example 1, 40.0 g of 2-fluoropyridine (0.412 mol) was converted to 46.5 g (72%) of the title compound as an oil: NMR($CDCl_3$, 200 MHz) 1.3 (3H, t, J=7 Hz), 2.95 (2H, q, J=7 Hz), 7.1 (1H, m), 7.7 (1H, m), 8.0 (1H, m); IR (neat) 1585, 1565, 1410, 1230 $cm^{-1}$.

EXAMPLE 8

Preparation of
3-ethylthio-2-(phenylmethylthio)pyridine

Utilizing the procedure of Example 2, 25.0 g (0.160 mol) of the product from Example 7 was converted to 44.8 g (100%) of the title compound as a yellow liquid: NMR ($CDCl_3$, 200 MHz) 1.28 (3H, t, J=7 Hz), 2.9 (2H, q, J=7 Hz), 4.45 (2H, s), 7.0–7.6 (7H, m), 8.35 (1H, m); IR (neat) 1610, 1405 $cm^{-1}$.

EXAMPLE 9

Preparation of
N-(1,1-Dimethylethyl)-3-ethylsulfinyl-2-pyridinesulfonamide

Utilizing the procedure of Example 3, 35.0 g (0.134 mol) of the product from Example 8 was converted to 21.2 g (56%) of the title compound: m.p. 129°–131°; NMR ($CDCl_3$, 200 MHz) 1.23 (9H, s), 1.28 (3H, t, J=7 Hz), 2.9 (1H, m), 3.3 (1H, m), 5.2 (NH), 7.7 (1H, m), 8.55 (1H, m), 8.75 (1H, m); IR (nujol) 3100, 1320, 1155 $cm^{-1}$.

EXAMPLE 10

Preparation of
N-(1,1-Dimethylethyl)-3-ethylsulfonyl-2-pyridinesulfonamide

Utilizing the first half of the procedure of Example 4 (i.e., the 3-chloroperbenzoic acid reaction), 9.0 g (0.033 mol) of the product from Example 9 was converted to 10.1 g (100%) of the title compound: m.p. 58°–63°; NMR ($CDCl_3$, 200 MHz) 1.2 (3H, t, J=7 Hz), 1.2 (9H, s), 3.7 (2H, q, J=7 Hz), 6.1 (NH), 7.7 (1H, m), 8.55 (1H, m), 8.95 (1H, m); IR (nujol) 3300, 1560, 1350, 1300, 1170, 1140 $cm^{-1}$.

EXAMPLE 11

Preparation of 3-ethylsulfonyl-2-pyridinesulfonamide

Utilizing the second half of the procedure of Example 4 (i.e., the trifluoroacetic acid reaction), 9.0 g (0.029 mol) of the product from Example 10 was converted to 4.2 g (58%) of the title compound: m.p. 211°–212.5°; NMR (DMSO-$d_6$, 200 MHz) 1.15 (3H, t, J=7 Hz), 3.4 ($NH_2$), 3.7 (2H, q, J=7 Hz), 7.9 (1H, m), 8.5 (1H, m), 8.95 (1H, m); IR (nujol) 3370, 3190, 1350, 1310, 1180 $cm^{-1}$.

EXAMPLE 12

Preparation of
N-[(4,6-dimethoxypyrimidin-2-yl)aminocarbonyl]-3-ethylsulfonyl-2-pyridinesulfonamide Utilizing the procedure of Example 5, 0.60 g (0.0024 mol) of the product from Example 11 was converted to 0.70 g (70%) of the title compound: m.p. 160°–162°; NMR ($CDCl_3$, 200 MHz) 1.35 (3H, t, J=7 Hz), 3.7 (2H, q, J=7 Hz), 3.97 (6H, s), 5.8 (1H, s), 7.3 (NH), 7.75 (1H, m), 8.6 (1H, m), 8.9 (1H, m), 12.95 (NH); IR (nujol) 3260, 1740, 1610, 1360, 1195, 1175 $cm^{-1}$.

By applying the procedures of Examples 1 through 12 and Equations 1 through 13, the compounds in Tables I through X can be prepared by one skilled in the art.

General Formulas For Tables

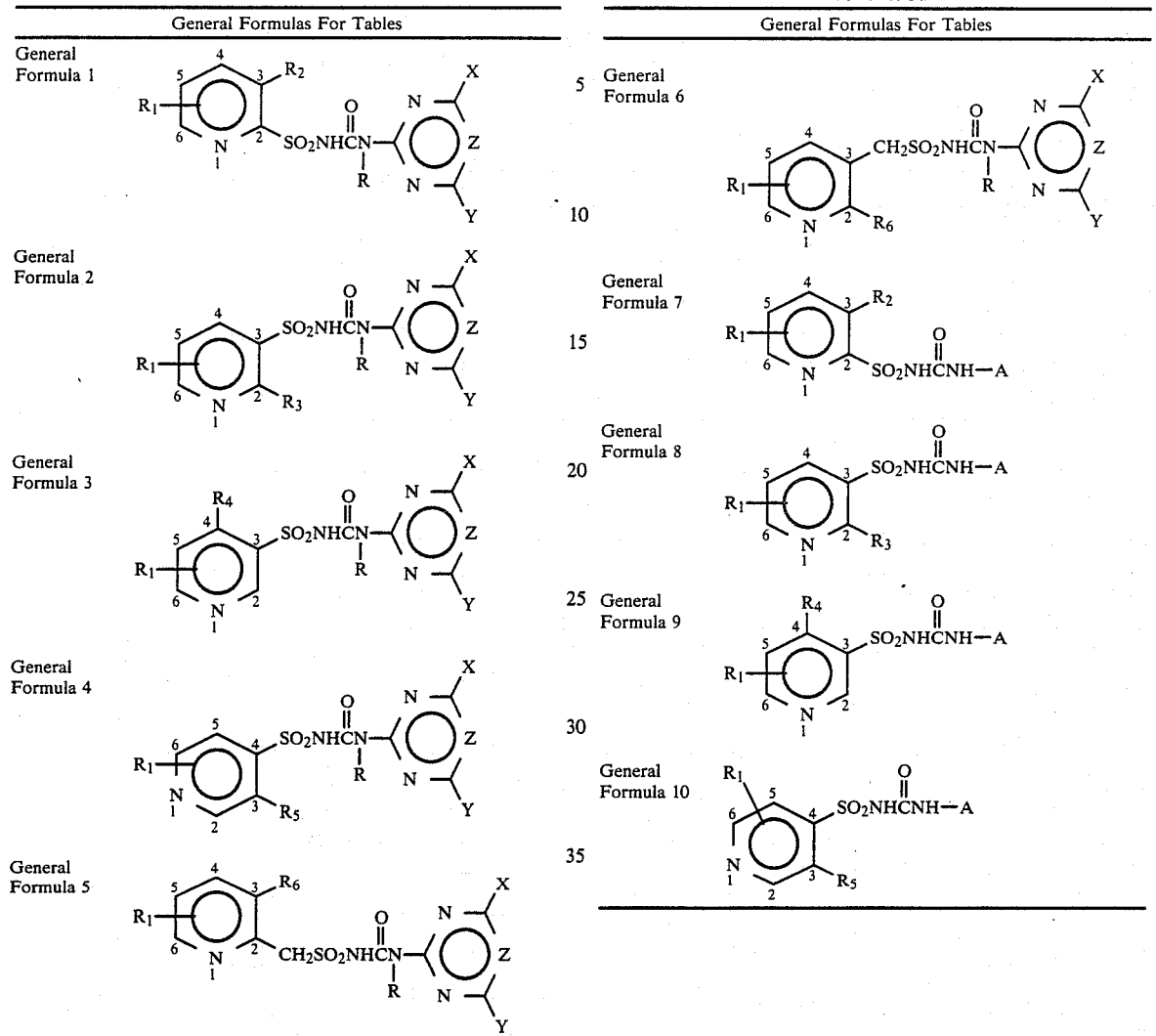

TABLE I

| | | General Formula 1 | | | | |
|---|---|---|---|---|---|---|
| $R_1$ | $R_2$ | R | X | Y | Z | m.p.(°C) |
| H | SOCH$_3$ | H | OCH$_3$ | OCH$_3$ | CH | 170–174 |
| H | SOCH$_3$ | H | OCH$_3$ | CH$_3$ | CH | 138–140 |
| H | SOCH$_3$ | H | Cl | OCH$_3$ | CH | 124–126 |
| H | SOCH$_3$ | H | CH$_3$ | CH$_3$ | CH | 126–127.5 |
| H | SOCH$_3$ | H | OCH$_3$ | OCH$_3$ | N | |
| H | SOCH$_3$ | H | OCH$_3$ | CH$_3$ | N | 165–167 |
| H | SOCH$_3$ | H | OCH$_2$CH$_3$ | NHCH$_3$ | N | |
| H | SOCH$_3$ | CH$_3$ | OCH$_3$ | CH$_3$ | N | 133–137 |
| 4-CH$_3$ | SOCH$_3$ | H | OCH$_3$ | OCH$_3$ | CH | |
| 4-OCH$_3$ | SOCH$_3$ | H | OCH$_3$ | OCH$_3$ | CH | |
| 6-CH$_3$ | SOCH$_3$ | H | OCH$_3$ | OCH$_3$ | CH | |
| 6-OCH$_3$ | SOCH$_3$ | H | OCH$_3$ | OCH$_3$ | CH | |
| 6-F | SOCH$_3$ | H | OCH$_3$ | OCH$_3$ | CH | |
| 6-Cl | SOCH$_3$ | H | OCH$_3$ | OCH$_3$ | CH | |
| H | SO$_2$CH$_3$ | H | OCH$_3$ | OCH$_3$ | CH | 170–172 |
| H | SO$_2$CH$_3$ | H | OCH$_3$ | CH$_3$ | CH | 158–160 |
| H | SO$_2$CH$_3$ | H | Cl | OCH$_3$ | CH | 158–160 |
| H | SO$_2$CH$_3$ | H | CH$_3$ | CH$_3$ | CH | 162–164 |
| H | SO$_2$CH$_3$ | H | OCH$_3$ | OCH$_3$ | N | 180–184 |
| H | SO$_2$CH$_3$ | H | OCH$_3$ | CH$_3$ | N | 154–156.5 |
| H | SO$_2$CH$_3$ | H | OCH$_2$CH$_3$ | NHCH$_3$ | N | |
| H | SO$_2$CH$_3$ | CH$_3$ | OCH$_3$ | CH$_3$ | N | |
| 4-CH$_3$ | SO$_2$CH$_3$ | H | OCH$_3$ | OCH$_3$ | CH | |
| 4-OCH$_3$ | SO$_2$CH$_3$ | H | OCH$_3$ | OCH$_3$ | CH | |
| 6-CH$_3$ | SO$_2$CH$_3$ | H | OCH$_3$ | OCH$_3$ | CH | |
| 6-OCH$_3$ | SO$_2$CH$_3$ | H | OCH$_3$ | OCH$_3$ | CH | |
| 6-F | SO$_2$CH$_3$ | H | OCH$_3$ | OCH$_3$ | CH | |

TABLE I-continued

| | | General Formula 1 | | | | |
|---|---|---|---|---|---|---|
| $R_1$ | $R_2$ | R | X | Y | Z | m.p.(°C.) |
| 6-Cl | SO$_2$CH$_3$ | H | OCH$_3$ | OCH$_3$ | CH | |
| H | SOCH$_2$CH$_3$ | H | OCH$_3$ | OCH$_3$ | CH | 132–136 |
| H | SOCH$_2$CH$_3$ | H | OCH$_3$ | CH$_3$ | CH | 141–144 |
| H | SOCH$_2$CH$_3$ | H | Cl | OCH$_3$ | CH | 105–107.5 |
| H | SOCH$_2$CH$_3$ | H | CH$_3$ | CH$_3$ | CH | 153–156.5 |
| H | SOCH$_2$CH$_3$ | H | OCH$_3$ | OCH$_3$ | N | 154–158 |
| H | SOCH$_2$CH$_3$ | H | OCH$_3$ | CH$_3$ | N | 172–174 |
| H | SOCH$_2$CH$_3$ | H | OCH$_2$CH$_3$ | NHCH$_3$ | N | |
| H | SOCH$_2$CH$_3$ | CH$_3$ | OCH$_3$ | CH$_3$ | N | |
| 4-CH$_3$ | SOCH$_2$CH$_3$ | H | OCH$_3$ | OCH$_3$ | CH | |
| 4-OCH$_3$ | SOCH$_2$CH$_3$ | H | OCH$_3$ | OCH$_3$ | CH | |
| 6-CH$_3$ | SOCH$_2$CH$_3$ | H | OCH$_3$ | OCH$_3$ | CH | |
| 6-OCH$_3$ | SOCH$_2$CH$_3$ | H | OCH$_3$ | OCH$_3$ | CH | |
| 6-F | SOCH$_2$CH$_3$ | H | OCH$_3$ | OCH$_3$ | CH | |
| 6-Cl | SOCH$_2$CH$_3$ | H | OCH$_3$ | OCH$_3$ | CH | |
| H | SO$_2$CH$_2$CH$_3$ | H | OCH$_3$ | OCH$_3$ | CH | 160–162 |
| H | SO$_2$CH$_2$CH$_3$ | H | OCH$_3$ | CH$_3$ | CH | 160–162 |
| H | SO$_2$CH$_2$CH$_3$ | H | Cl | OCH$_3$ | CH | 163–164.5 |
| H | SO$_2$CH$_2$CH$_3$ | H | CH$_3$ | CH$_3$ | CH | 167–169 |
| H | SO$_2$CH$_2$CH$_3$ | H | OCH$_3$ | OCH$_3$ | N | 155–158 |
| H | SO$_2$CH$_2$CH$_3$ | H | OCH$_3$ | CH$_3$ | N | 165.5–168 |
| H | SO$_2$CH$_2$CH$_3$ | H | OCH$_2$CH$_3$ | NHCH$_3$ | N | |
| H | SO$_2$CH$_2$CH$_3$ | CH$_3$ | OCH$_3$ | CH$_3$ | N | 137–138 |
| 4-CH$_3$ | SO$_2$CH$_2$CH$_3$ | H | OCH$_3$ | OCH$_3$ | CH | |
| 4-OCH$_3$ | SO$_2$CH$_2$CH$_3$ | H | OCH$_3$ | OCH$_3$ | CH | |
| 6-CH$_3$ | SO$_2$CH$_2$CH$_3$ | H | OCH$_3$ | OCH$_3$ | CH | 178–180 |
| 6-CH$_3$ | SO$_2$CH$_2$CH$_3$ | H | OCH$_3$ | CH$_3$ | CH | 169.5–172 |
| 6-CH$_3$ | SO$_2$CH$_2$CH$_3$ | H | CH$_3$ | CH$_3$ | CH | 172–173.5 |
| 6-CH$_3$ | SO$_2$CH$_2$CH$_3$ | CH$_3$ | OCH$_3$ | CH$_3$ | N | 133–135 |
| 6-OCH$_3$ | SO$_2$CH$_2$CH$_3$ | H | OCH$_3$ | OCH$_3$ | CH | 210–213 |
| 6-F | SO$_2$CH$_2$CH$_3$ | H | OCH$_3$ | OCH$_3$ | CH | 157–160 |
| 6-F | SO$_2$CH$_2$CH$_3$ | H | CH$_3$ | CH$_3$ | CH | 176–177 |
| 6-Cl | SO$_2$CH$_2$CH$_3$ | H | OCH$_3$ | OCH$_3$ | CH | 187–189 |
| 6-Cl | SO$_2$CH$_2$CH$_3$ | H | Cl | OCH$_3$ | CH | 171–174 |
| 6-Cl | SO$_2$CH$_2$CH$_3$ | H | CH$_3$ | CH$_3$ | CH | 181–182 |
| 6-SCH$_3$ | SO$_2$CH$_2$CH$_3$ | H | OCH$_3$ | OCH$_3$ | CH | |
| 6-SCH$_3$ | SO$_2$CH$_2$CH$_3$ | H | Cl | OCH$_3$ | CH | |
| 5-CH$_3$ | SO$_2$CH$_2$CH$_3$ | H | OCH$_3$ | OCH$_3$ | CH | 159–160 |
| 5-CH$_3$ | SO$_2$CH$_2$CH$_3$ | H | Cl | OCH$_3$ | CH | 176–177 |
| 5-CH$_3$ | SO$_2$CH$_2$CH$_3$ | H | OCH$_3$ | OCH$_3$ | N | 155–156 |
| 5-CH$_3$ | SO$_2$CH$_2$CH$_3$ | H | OCH$_3$ | CH$_3$ | N | 159–161 |
| H | SOCH$_2$CH$_2$CH$_3$ | H | OCH$_3$ | OCH$_3$ | CH | 111–115 |
| H | SOCH$_2$CH$_2$CH$_3$ | H | OCH$_3$ | CH$_3$ | CH | 141–145 |
| H | SOCH$_2$CH$_2$CH$_3$ | H | Cl | OCH$_3$ | CH | 111–113 |
| H | SOCH$_2$CH$_2$CH$_3$ | H | CH$_3$ | CH$_3$ | CH | 173–175 |
| H | SOCH$_2$CH$_2$CH$_3$ | H | OCH$_3$ | OCH$_3$ | N | 186–189 |
| H | SOCH$_2$CH$_2$CH$_3$ | H | OCH$_3$ | CH$_3$ | N | 164–166 |
| H | SOCH$_2$CH$_2$CH$_3$ | H | OCH$_2$CH$_3$ | NHCH$_3$ | N | 121–123 |
| H | SOCH$_2$CH$_2$CH$_3$ | CH$_3$ | OCH$_3$ | CH$_3$ | N | |
| 4-CH$_3$ | SOCH$_2$CH$_2$CH$_3$ | H | OCH$_3$ | OCH$_3$ | CH | |
| 4-OCH$_3$ | SOCH$_2$CH$_2$CH$_3$ | H | OCH$_3$ | OCH$_3$ | CH | |
| 6-CH$_3$ | SOCH$_2$CH$_2$CH$_3$ | H | OCH$_3$ | OCH$_3$ | CH | |
| 6-OCH$_3$ | SOCH$_2$CH$_2$CH$_3$ | H | OCH$_3$ | OCH$_3$ | CH | |
| 6-F | SOCH$_2$CH$_2$CH$_3$ | H | OCH$_3$ | OCH$_3$ | CH | |
| 6-Cl | SOCH$_2$CH$_2$CH$_3$ | H | OCH$_3$ | OCH$_3$ | CH | |
| H | SO$_2$CH$_2$CH$_2$CH$_3$ | H | OCH$_3$ | OCH$_3$ | CH | 168–170 |
| H | SO$_2$CH$_2$CH$_2$CH$_3$ | H | OCH | CH$_3$ | CH | 157–159 |
| H | SO$_2$CH$_2$CH$_2$CH$_3$ | H | Cl | OCH$_3$ | CH | 165–167 |
| H | SO$_2$CH$_2$CH$_2$CH$_3$ | H | CH$_3$ | CH$_3$ | CH | 158–160 |
| H | SO$_2$CH$_2$CH$_2$CH$_3$ | H | OCH$_3$ | OCH$_3$ | N | 164–166 |
| H | SO$_2$CH$_2$CH$_2$CH$_3$ | H | OCH$_3$ | CH$_3$ | N | 165–168 |
| H | SO$_2$CH$_2$CH$_2$CH$_3$ | H | OCH$_2$CH$_3$ | NHCH$_3$ | N | 148–152 |
| H | SO$_2$CH$_2$CH$_2$CH$_3$ | CH$_3$ | OCH$_3$ | CH$_3$ | N | |
| 4-CH$_3$ | SO$_2$CH$_2$CH$_2$CH$_3$ | H | OCH$_3$ | OCH$_3$ | CH | |
| 4-OCH$_3$ | SO$_2$CH$_2$CH$_2$CH$_3$ | H | OCH$_3$ | OCH$_3$ | CH | |
| 6-CH$_3$ | SO$_2$CH$_2$CH$_2$CH$_3$ | H | OCH$_3$ | OCH$_3$ | CH | |
| 6-OCH$_3$ | SO$_2$CH$_2$CH$_2$CH$_3$ | H | OCH$_3$ | OCH$_3$ | CH | |
| 6-F | SO$_2$CH$_2$CH$_2$CH$_3$ | H | OCH$_3$ | OCH$_3$ | CH | |
| 6-Cl | SO$_2$CH$_2$CH$_2$CH$_3$ | H | OCH$_3$ | OCH$_3$ | CH | |
| H | SOCH(CH$_3$)$_2$ | H | OCH$_3$ | OCH$_3$ | CH | 144–147 |
| H | SOCH(CH$_3$)$_2$ | H | OCH$_3$ | CH$_3$ | CH | 143–145.5 |
| H | SOCH(CH$_3$)$_2$ | H | Cl | OCH$_3$ | CH | 133–135 |
| H | SOCH(CH$_3$)$_2$ | H | CH$_3$ | CH$_3$ | CH | 150–153 |
| H | SOCH(CH$_3$)$_2$ | H | OCH$_3$ | OCH$_3$ | N | 155–159 |
| H | SOCH(CH$_3$)$_2$ | H | OCH$_3$ | CH | N | 150–153 |
| H | SOCH(CH$_3$)$_2$ | H | OCH$_2$CH$_3$ | NHCH$_3$ | N | |
| H | SOCH(CH$_3$)$_2$ | CH$_3$ | OCH$_3$ | CH$_3$ | N | |
| 4-CH$_3$ | SOCH(CH$_3$)$_2$ | H | OCH$_3$ | OCH$_3$ | CH | |
| 4-OCH$_3$ | SOCH(CH$_3$)$_2$ | H | OCH$_3$ | OCH$_3$ | CH | |
| 6-CH$_3$ | SOCH(CH$_3$)$_2$ | H | OCH$_3$ | OCH$_3$ | CH | |

TABLE I-continued

General Formula 1

| R₁ | R₂ | R | X | Y | Z | m.p.(°C.) |
|---|---|---|---|---|---|---|
| 6-OCH₃ | SOCH(CH₃)₂ | H | OCH₃ | OCH₃ | CH | |
| 6-F | SOCH(CH₃)₂ | H | OCH₃ | OCH₃ | CH | |
| 6-Cl | SOCH(CH₃)₂ | H | OCH₃ | OCH₃ | CH | |
| H | SO₂CH(CH₃)₂ | H | OCH₃ | OCH₃ | CH | 140–146 |
| H | SO₂CH(CH₃)₂ | H | OCH₃ | CH₃ | CH | 159–160.5 |
| H | SO₂CH(CH₃)₂ | H | Cl | OCH₃ | CH | 164–165.5 |
| H | SO₂CH(CH₃)₂ | H | CH₃ | CH₃ | CH | 161–163 |
| H | SO₂CH(CH₃)₂ | H | OCH₃ | OCH₃ | N | 164–166 |
| H | SO₂CH(CH₃)₂ | H | OCH₃ | CH₃ | N | 165–167 |
| H | SO₂CH(CH₃)₂ | H | OCH₂CH₃ | NHCH₃ | N | |
| H | SO₂CH(CH₃)₂ | CH₃ | OCH₃ | CH₃ | N | 145–149 |
| 4-CH₃ | SO₂CH(CH₃)₂ | H | OCH₃ | OCH₃ | CH | |
| 4-OCH₃ | SO₂CH(CH₃)₂ | H | OCH₃ | OCH₃ | CH | |
| 6-CH₃ | SO₂CH(CH₃)₂ | H | OCH₃ | OCH₃ | CH | |
| 6-OCH₃ | SO₂CH(CH₃)₂ | H | OCH₃ | OCH₃ | CH | |
| 6-F | SO₂CH(CH₃)₂ | H | OCH₃ | OCH₃ | CH | |
| 6-Cl | SO₂CH(CH₃)₂ | H | OCH₃ | OCH₃ | CH | |
| H | SOCH₂CH₂CH₂CH₃ | H | OCH₃ | OCH₃ | CH | |
| H | SOCH₂CH₂CH₂CH₃ | H | OCH₃ | CH₃ | CH | |
| H | SOCH₂CH₂CH₂CH₃ | H | Cl | OCH₃ | CH | |
| H | SOCH₂CH₂CH₂CH₃ | H | CH₃ | CH₃ | CH | |
| H | SOCH₂CH₂CH₂CH₃ | H | OCH₃ | OCH₃ | N | |
| H | SOCH₂CH₂CH₂CH₃ | H | OCH₃ | CH₃ | N | |
| H | SOCH₂CH₂CH₂CH₃ | H | OCH₂CH₃ | NHCH₃ | N | |
| H | SOCH₂CH₂CH₂CH₃ | H | OCH₃ | CH₃ | N | |
| 4-CH₃ | SOCH₂CH₂CH₂CH₃ | H | OCH₃ | OCH₃ | CH | |
| 4-OCH₃ | SOCH₂CH₂CH₂CH₃ | H | OCH₃ | OCH₃ | CH | |
| 6-CH₃ | SOCH₂CH₂CH₂CH₃ | H | OCH₃ | OCH₃ | CH | |
| 6-OCH₃ | SOCH₂CH₂CH₂CH₃ | H | OCH₃ | OCH₃ | CH | |
| 6-F | SOCH₂CH₂CH₂CH₃ | H | OCH₃ | OCH₃ | CH | |
| 6-Cl | SOCH₂CH₂CH₂CH₃ | H | OCH₃ | OCH₃ | CH | |
| H | SO₂CH₂CH₂CH₂CH₃ | H | OCH₃ | OCH₃ | CH | 155–157 |
| H | SO₂CH₂CH₂CH₂CH₃ | H | OCH₃ | CH₃ | CH | 142–144 |
| H | SO₂CH₂CH₂CH₂CH₃ | H | Cl | OCH₃ | CH | 151–153 |
| H | SO₂CH₂CH₂CH₂CH₃ | H | CH₃ | CH₃ | CH' | 142–143 |
| H | SO₂CH₂CH₂CH₂CH₃ | H | OCH₃ | OCH₃ | N | 153.5–155 |
| H | SO₂CH₂CH₂CH₂CH₃ | H | OCH₃ | CH₃ | N | 142.5–145.5 |
| H | SO₂CH₂CH₂CH₂CH₃ | H | OHCH₂CH₃ | NHCH₃ | N | |
| H | SO₂CH₂CH₂CH₂CH₃ | CH₃ | OCH₃ | CH₃ | N | |
| H | SO₂CH₂CH₂CH₂CH₃ | CH₃ | OCH₃ | OCH₃ | N | 133–136 |
| 4-CH₃ | SO₂CH₂CH₂CH₂CH₃ | H | OCH₃ | OCH₃ | CH | |
| 4-OCH₃ | SO₂CH₂CH₂CH₂CH₃ | H | OCH₃ | OCH₃ | CH | |
| 6-CH₃ | SO₂CH₂CH₂CH₂CH₃ | H | OCH₃ | OCH₃ | CH | |
| 6-OCH₃ | SO₂CH₂CH₂CH₂CH₃ | H | OCH₃ | OCH₃ | CH | |
| 6-F | SO₂CH₂CH₂CH₂CH₃ | H | OCH₃ | OCH₃ | CH | |
| 6-Cl | SO₂CH₂CH₂CH₂CH₃ | H | OCH₃ | OCH₃ | CH | |
| H | S—cyclopropyl | H | OCH₃ | OCH₃ | CH | |
| H | S—cyclopropyl | H | OCH₃ | CH₃ | CH | |
| H | S—cyclopropyl | H | Cl | OCH₃ | CH | |
| H | S—cyclopropyl | H | CH₃ | CH₃ | CH | |
| H | S—cyclopropyl | H | OCH₃ | OCH₃ | N | |
| H | S—cyclopropyl | H | OCH₃ | CH₃ | N | |
| H | S—cyclopropyl | H | OCH₂CH₃ | NHCH₃ | N | |
| H | S—cyclopropyl | CH₃ | OCH₃ | CH₃ | N | |
| 4-CH₃ | S—cyclopropyl | H | OCH₃ | OCH₃ | CH | |
| 4-OCH₃ | S—cyclopropyl | H | OCH₃ | OCH₃ | CH | |
| 6-CH₃ | S—cyclopropyl | H | OCH₃ | OCH₃ | CH | |
| 6-OCH₃ | S—cyclopropyl | H | OCH₃ | OCH₃ | CH | |
| 6-F | S—cyclopropyl | H | OCH₃ | OCH₃ | CH | |
| 6-Cl | S—cyclopropyl | H | OCH₃ | OCH₃ | CH | |
| H | SO—cyclopropyl | H | OCH₃ | OCH₃ | CH | |
| H | SO—cyclopropyl | H | OCH₃ | CH₃ | CH | |
| H | SO—cyclopropyl | H | Cl | OCH₃ | CH | |
| H | SO—cyclopropyl | H | CH₃ | CH₃ | CH | |
| H | SO—cyclopropyl | H | OCH₃ | OCH₃ | N | |
| H | SO—cyclopropyl | H | OCH₃ | CH₃ | N | |
| H | SO—cyclopropyl | H | OCH₂CH₃ | NHCH₃ | N | |
| H | SO—cyclopropyl | CH₃ | OCH₃ | CH₃ | N | |
| 4-CH₃ | SO—cyclopropyl | H | OCH₃ | OCH₃ | CH | |
| 4-OCH₃ | SO—cyclopropyl | H | OCH₃ | OCH₃ | CH | |
| 6-CH₃ | SO—cyclopropyl | H | OCH₃ | OCH₃ | CH | |
| 6-OCH₃ | SO—cyclopropyl | H | OCH₃ | OCH₃ | CH | |
| 6-F | SO—cyclopropyl | H | OCH₃ | OCH₃ | CH | |
| 6-Cl | SO—cyclopropyl | H | OCH₃ | OCH₃ | CH | |
| H | SO₂—cyclopropyl | H | OCH₃ | OCH₃ | CH | |
| H | SO₂—cyclopropyl | H | OCH₃ | CH₃ | CH | |
| H | SO₂—cyclopropyl | H | Cl | OCH₃ | CH | |
| H | SO₂—cyclopropyl | H | CH₃ | CH₃ | CH | |
| H | SO₂—cyclopropyl | H | OCH₃ | OCH₃ | N | |
| H | SO₂—cyclopropyl | H | OCH₃ | CH₃ | N | |

TABLE I-continued

General Formula 1

| R₁ | R₂ | R | X | Y | Z | m.p.(°C.) |
|---|---|---|---|---|---|---|
| H | SO₂—cyclopropyl | H | OCH₂CH₃ | NHCH₃ | N | |
| H | SO₂—cyclopropyl | CH₃ | OCH₃ | CH₃ | N | |
| 4-CH₃ | SO₂—cyclopropyl | H | OCH₃ | OCH₃ | CH | |
| 4-OCH₃ | SO₂—cyclopropyl | H | OCH₃ | OCH₃ | CH | |
| 6-CH₃ | SO₂—cyclopropyl | H | OCH₃ | OCH₃ | CH | |
| 6-OCH₃ | SO₂—cyclopropyl | H | OCH₃ | OCH₃ | CH | |
| 6-F | SO₂—cyclopropyl | H | OCH₃ | OCH₃ | CH | |
| 6-Cl | SO₂—cyclopropyl | H | OCH₃ | OCH₃ | CH | |
| H | OSO₂CH₃ | H | OCH₃ | OCH₃ | CH | 169–171 |
| H | OSO₂CH₃ | H | OCH₃ | CH₃ | CH | 172–173.5 |
| H | OSO₂CH₃ | H | Cl | OCH₃ | CH | 171–173 |
| H | OSO₂CH₃ | H | CH₃ | CH₃ | CH | 161.5–165 |
| H | OSO₂CH₃ | H | OCH₃ | OCH₃ | N | |
| H | OSO₂CH₃ | H | OCH₃ | CH₃ | N | 155–158 |
| H | OSO₂CH₃ | H | OCH₂CH₃ | NHCH₃ | N | |
| H | OSO₂CH₃ | CH₃ | OCH₃ | CH₃ | N | |
| 4-CH₃ | OSO₂CH₃ | H | OCH₃ | OCH₃ | CH | |
| 4-OCH₃ | OSO₂CH₃ | H | OCH₃ | OCH₃ | CH | |
| 6-CH₃ | OSO₂CH₃ | H | OCH₃ | OCH₃ | CH | |
| 6-OCH₃ | OSO₂CH₃ | H | OCH₃ | OCH₃ | CH | |
| 6-F | OSO₂CH₃ | H | OCH₃ | OCH₃ | CH | |
| 6-Cl | OSO₂CH₃ | H | OCH₃ | OCH₃ | CH | |
| H | OSO₂CH₂CH₃ | H | OCH₃ | OCH₃ | CH | 162–163.5 |
| H | OSO₂CH₂CH₃ | H | OCH₃ | CH₃ | CH | 160–162 |
| H | OSO₂CH₂CH₃ | H | Cl | OCH₃ | CH | 139–143 |
| H | OSO₂CH₂CH₃ | H | CH₃ | CH₃ | CH | 132–138 |
| H | OSO₂CH₂CH₃ | H | OCH₃ | OCH₃ | N | 171.5–173 |
| H | OSO₂CH₂CH₃ | H | OCH₃ | CH₃ | N | 147–149 |
| H | OSO₂CH₂CH₃ | H | OCH₂CH₃ | NHCH₃ | N | |
| H | OSO₂CH₂CH₃ | CH₃ | OCH₃ | CH₃ | N | |
| 4-CH₃ | OSO₂CH₂CH₃ | H | OCH₃ | OCH₃ | CH | |
| 4-OCH₃ | OSO₂CH₂CH₃ | H | OCH₃ | OCH₃ | CH | |
| 6-CH₃ | OSO₂CH₂CH₃ | H | OCH₃ | OCH₃ | CH | |
| 6-OCH₃ | OSO₂CH₂CH₃ | H | OCH₃ | OCH₃ | CH | |
| 6-F | OSO₂CH₂CH₃ | H | OCH₃ | OCH₃ | CH | |
| 6-Cl | OSO₂CH₂CH₃ | H | OCH₃ | OCH₃ | CH | |
| H | OSO₂CH₂CH₂CH₃ | H | OCH₃ | OCH₃ | CH | |
| H | OSO₂CH₂CH₂CH₃ | H | OCH₃ | CH₃ | CH | |
| H | OSO₂CH₂CH₂CH₃ | H | Cl | OCH₃ | CH | |
| H | OSO₂CH₂CH₂CH₃ | H | CH₃ | CH₃ | CH | |
| H | OSO₂CH₂CH₂CH₃ | H | OCH₃ | OCH₃ | N | |
| H | OSO₂CH₂CH₂CH₃ | H | OCH₃ | CH₃ | N | |
| H | OSO₂CH₂CH₂CH₃ | H | OCH₂CH₃ | NHCH₃ | N | |
| H | OSO₂CH₂CH₂CH₃ | CH₃ | OCH₃ | CH₃ | N | |
| 4-CH₃ | OSO₂CH₂CH₂CH₃ | H | OCH₃ | OCH₃ | CH | |
| 4-OCH₃ | OSO₂CH₂CH₂CH₃ | H | OCH₃ | OCH₃ | CH | |
| 6-CH₃ | OSO₂CH₂CH₂CH₃ | H | OCH₃ | OCH₃ | CH | |
| 6-OCH₃ | OSO₂CH₂CH₂CH₃ | H | OCH₃ | OCH₃ | CH | |
| 6-F | OSO₂CH₂CH₂CH₃ | H | OCH₃ | OCH₃ | CH | |
| 6-Cl | OSO₂CH₂CH₂CH₃ | H | OCH₃ | OCH₃ | CH | |
| H | OSO₂CH(CH₃)₂ | H | OCH₃ | OCH₃ | CH | |
| H | OSO₂CH(CH₃)₂ | H | OCH₃ | CH₃ | CH | |
| H | OSO₂CH(CH₃)₂ | H | Cl | OCH₃ | CH | |
| H | OSO₂CH(CH₃)₂ | H | CH₃ | CH₃ | CH | |
| H | OSO₂CH(CH₃)₂ | H | OCH₃ | OCH₃ | N | |
| H | OSO₂CH(CH₃)₂ | H | OCH₃ | CH₃ | N | |
| H | OSO₂CH(CH₃)₂ | H | OCH₂CH₃ | NHCH₃ | N | |
| H | OSO₂CH(CH₃)₂ | CH₃ | OCH₃ | CH₃ | N | |
| 4-CH₃ | OSO₂CH(CH₃)₂ | H | OCH₃ | OCH₃ | CH | |
| 4-OCH₃ | OSO₂CH(CH₃)₂ | H | OCH₃ | OCH₃ | CH | |
| 6-CH₃ | OSO₂CH(CH₃)₂ | H | OCH₃ | OCH₃ | CH | |
| 6-OCH₃ | OSO₂CH(CH₃)₂ | H | OCH₃ | OCH₃ | CH | |
| 6-F | OSO₂CH(CH₃)₂ | H | OCH₃ | OCH₃ | CH | |
| 6-Cl | OSO₂CH(CH₃)₂ | H | OCH₃ | OCH₃ | CH | |
| H | OSO₂CH₂CH₂CH₂CH₃ | H | OCH₃ | OCH₃ | CH | |
| H | OSO₂CH₂CH₂CH₂CH₃ | H | OCH₃ | CH₃ | CH | |
| H | OSO₂CH₂CH₂CH₂CH₃ | H | Cl | OCH₃ | CH | |
| H | OSO₂CH₂CH₂CH₂CH₃ | H | CH₃ | CH₃ | CH | |
| H | OSO₂CH₂CH₂CH₂CH₃ | H | OCH₃ | OCH₃ | N | |
| H | OSO₂CH₂CH₂CH₂CH₃ | H | OCH₃ | CH₃ | N | |
| H | OSO₂CH₂CH₂CH₂CH₃ | H | OCH₂CH₃ | NHCH₃ | N | |
| H | OSO₂CH₂CH₂CH₂CH₃ | CH₃ | OCH₃ | CH₃ | N | |
| 4-CH₃ | OSO₂CH₂CH₂CH₂CH₃ | H | OCH₃ | OCH₃ | CH | |
| 4-OCH₃ | OSO₂CH₂CH₂CH₂CH₃ | H | OCH₃ | OCH₃ | CH | |
| 6-CH₃ | OSO₂CH₂CH₂CH₂CH₃ | H | OCH₃ | OCH₃ | CH | |
| 6-OCH₃ | OSO₂CH₂CH₂CH₂CH₃ | H | OCH₃ | OCH | CH | |
| 6-F | OSO₂CH₂CH₂CH₂CH₃ | H | OCH₃ | OCH₃ | CH | |
| 6-Cl | OSO₂CH₂CH₂CH₂CH₃ | H | OCH₃ | OCH₃ | CH | |
| H | OSO₂CF₃ | H | OCH₃ | OCH₃ | CH | 140–142 |
| H | OSO₂CF₃ | H | OCH₃ | CH₃ | CH | |

TABLE I-continued

General Formula 1

| R₁ | R₂ | R | X | Y | Z | m.p.(°C.) |
|---|---|---|---|---|---|---|
| H | OSO₂CF₃ | H | Cl | OCH₃ | CH | 154–156 |
| H | OSO₂CF₃ | H | CH₃ | CH₃ | CH | 157–160 |
| H | OSO₂CF₃ | H | OCH₃ | OCH₃ | N | 164–166 |
| H | OSO₂CF₃ | H | OCH₃ | CH₃ | N | 157–159 |
| H | OSO₂CF₃ | H | OCH₂CH₃ | NHCH₃ | N | |
| H | OSO₂CF₃ | CH₃ | OCH₃ | CH₃ | N | |
| 4-CH₃ | OSO₂CF₃ | H | OCH₃ | OCH₃ | CH | |
| 4-OCH₃ | OSO₂CF₃ | H | OCH₃ | OCH₃ | CH | |
| 6-CH₃ | OSO₂CF₃ | H | OCH₃ | OCH₃ | CH | |
| 6-OCH₃ | OSO₂CF₃ | H | OCH₃ | OCH₃ | CH | |
| 6-F | OSO₂CF₃ | H | OCH₃ | OCH₃ | CH | |
| 6-Cl | OSO₂CF₃ | H | OCH₃ | OCH₃ | CH | |
| H | OSO₂CCl₃ | H | OCH₃ | OCH₃ | CH | |
| H | OSO₂CCl₃ | H | OCH₃ | CH₃ | CH | |
| H | OSO₂CCl₃ | H | Cl | OCH₃ | CH | |
| H | OSO₂CCl₃ | H | CH₃ | CH₃ | CH | |
| H | OSO₂CCl₃ | H | OCH₃ | OCH₃ | N | |
| H | OSO₂CCl₃ | H | OCH₃ | CH₃ | N | |
| H | OSO₂CCl₃ | H | OCH₂CH₃ | NHCH₃ | N | |
| H | OSO₂CCl₃ | CH₃ | OCH₃ | CH₃ | N | |
| 4-CH₃ | OSO₂CCl₃ | H | OCH₃ | OCH₃ | CH | |
| 4-OCH₃ | OSO₂CCl₃ | H | OCH₃ | OCH₃ | CH | |
| 6-CH₃ | OSO₂CCl₃ | H | OCH₃ | OCH₃ | CH | |
| 6-OCH₃ | OSO₂CCl₃ | H | OCH₃ | OCH₃ | CH | |
| 6-F | OSO₂CCl₃ | H | OCH₃ | OCH₃ | CH | |
| 6-Cl | OSO₂CCl₃ | H | OCH₃ | OCH₃ | CH | |
| H | OSO₂CH₂CH₂CH₂Cl | H | OCH₃ | OCH₃ | CH | |
| H | OSO₂CH₂CH₂CH₂Cl | H | OCH₃ | CH₃ | CH | |
| H | OSO₂CH₂CH₂CH₂Cl | H | Cl | OCH₃ | CH | |
| H | OSO₂CH₂CH₂CH₂Cl | H | CH₃ | CH₃ | CH | |
| H | OSO₂CH₂CH₂CH₂Cl | H | OCH₃ | OCH₃ | N | |
| H | OSO₂CH₂CH₂CH₂Cl | H | OCH₃ | CH₃ | N | |
| H | OSO₂CH₂CH₂CH₂Cl | H | OCH₂CH₃ | NHCH₃ | N | |
| H | OSO₂CH₂CH₂CH₂Cl | CH₃ | OCH₃ | CH₃ | N | |
| 4-CH₃ | OSO₂CH₂CH₂CH₂Cl | H | OCH₃ | OCH₃ | CH | |
| 4-OCH₃ | OSO₂CH₂CH₂CH₂Cl | H | OCH₃ | OCH₃ | CH | |
| 6-CH₃ | OSO₂CH₂CH₂CH₂Cl | H | OCH₃ | OCH₃ | CH | |
| 6-OCH₃ | OSO₂CH₂CH₂CH₂Cl | H | OCH₃ | OCH₃ | CH | |
| 6-F | OSO₂CH₂CH₂CH₂Cl | H | OCH₃ | OCH₃ | CH | |
| 6-Cl | OSO₂CH₂CH₂CH₂Cl | H | OCH₃ | OCH₃ | CH | |
| H | SO₂OCH₂CF₃ | H | OCH₃ | OCH₃ | CH | |
| H | SO₂OCH₂CF₃ | H | OCH₃ | CH₃ | CH | |
| H | SO₂OCH₂CF₃ | H | Cl | OCH₃ | CH | |
| H | SO₂OCH₂CF₃ | H | CH₃ | CH₃ | CH | |
| H | SO₂OCH₂CF₃ | H | OCH₃ | OCH₃ | N | |
| H | SO₂OCH₂CF₃ | H | OCH₃ | CH₃ | N | |
| H | SO₂OCH₂CF₃ | H | OCH₂CH₃ | NHCH₃ | N | |
| H | SO₂OCH₂CF₃ | CH₃ | OCH₃ | CH₃ | N | |
| 4-CH₃ | SO₂OCH₂CF₃ | H | OCH₃ | OCH₃ | CH | |
| 4-OCH₃ | SO₂OCH₂CF₃ | H | OCH₃ | OCH₃ | CH | |
| 6-CH₃ | SO₂OCH₂CF₃ | H | OCH₃ | OCH₃ | CH | |
| 6-OCH₃ | SO₂OCH₂CF₃ | H | OCH₃ | OCH₃ | CH | |
| 6-F | SO₂OCH₂CF₃ | H | OCH₃ | OCH₃ | CH | |
| 6-Cl | SO₂OCH₂CF₃ | H | OCH₃ | OCH₃ | CH | |
| H | SO₂OCH₃ | H | OCH₃ | OCH₃ | CH | |
| H | SO₂OCH₃ | H | OCH₃ | CH₃ | CH | |
| H | SO₂OCH₃ | H | Cl | OCH₃ | CH | |
| H | SO₂OCH₃ | H | CH₃ | CH₃ | CH | |
| H | SO₂OCH₃ | H | OCH₃ | OCH₃ | N | |
| H | SO₂OCH₃ | H | OCH₃ | CH₃ | N | |
| H | SO₂OCH₃ | H | OCH₂CH₃ | NHCH₃ | N | |
| H | SO₂OCH₃ | CH₃ | OCH₃ | CH₃ | N | |
| 4-CH₃ | SO₂OCH₃ | H | OCH₃ | OCH₃ | CH | |
| 4-OCH₃ | SO₂OCH₃ | H | OCH₃ | OCH₃ | CH | |
| 6-CH₃ | SO₂OCH₃ | H | OCH₃ | OCH₃ | CH | |
| 6-OCH₃ | SO₂OCH₃ | H | OCH₃ | OCH₃ | CH | |
| 6-F | SO₂OCH₃ | H | OCH₃ | OCH₃ | CH | |
| 6-Cl | SO₂OCH₃ | H | OCH₃ | OCH₃ | CH | |
| H | SO₂OCH₂CH₃ | H | OCH₃ | OCH₃ | CH | |
| H | SO₂OCH₂CH₃ | H | OCH₃ | CH₃ | CH | |
| H | SO₂OCH₂CH₃ | H | Cl | OCH₃ | CH | |
| H | SO₂OCH₂CH₃ | H | CH₃ | CH₃ | CH | |
| H | SO₂OCH₂CH₃ | H | OCH₃ | OCH₃ | N | |
| H | SO₂OCH₂CH₃ | H | OCH₃ | CH₃ | N | |
| H | SO₂OCH₂CH₃ | H | OCH₂CH₃ | NHCH₃ | N | |
| H | SO₂OCH₂CH₃ | CH₃ | OCH₃ | CH₃ | N | |
| 4-CH₃ | SO₂OCH₂CH₃ | H | OCH₃ | OCH₃ | CH | |
| 4-OCH₃ | SO₂OCH₂CH₃ | H | OCH₃ | OCH₃ | CH | |
| 6-CH₃ | SO₂OCH₂CH₃ | H | OCH₃ | OCH₃ | CH | |
| 6-OCH₃ | SO₂OCH₂CH₃ | H | OCH₃ | OCH₃ | CH | |

TABLE I-continued

General Formula 1

| R₁ | R₂ | R | X | Y | Z | m.p.(°C.) |
|---|---|---|---|---|---|---|
| 6-F | SO₂OCH₂CH₃ | H | OCH₃ | OCH₃ | CH | |
| 6-Cl | SO₂OCH₂CH₃ | H | OCH₃ | OCH₃ | CH | |
| H | N₃ | H | OCH₃ | OCH₃ | CH | |
| H | N₃ | H | OCH₃ | CH₃ | CH | |
| H | N₃ | H | Cl | OCH₃ | CH | |
| H | N₃ | H | CH₃ | CH₃ | CH | |
| H | N₃ | H | OCH₃ | OCH₃ | N | |
| H | N₃ | H | OCH₃ | CH₃ | N | |
| H | N₃ | H | OCH₂CH₃ | NHCH₃ | N | |
| H | N₃ | CH₃ | OCH₃ | CH₃ | N | |
| 4-CH₃ | N₃ | H | OCH₃ | OCH₃ | CH | |
| 4-OCH₃ | N₃ | H | OCH₃ | OCH₃ | CH | |
| 6-CH₃ | N₃ | H | OCH₃ | OCH₃ | CH | |
| 6-OCH₃ | N₃ | H | OCH₃ | OCH₃ | CH | |
| 6-F | N₃ | H | OCH₃ | OCH₃ | CH | |
| 6-Cl | N₃ | H | OCH₃ | OCH₃ | CH | |
| H | CN | H | OCH₃ | OCH₃ | CH | |
| H | CN | H | OCH₃ | CH₃ | CH | |
| H | CN | H | Cl | OCH₃ | CH | |
| H | CN | H | CH₃ | CH₃ | CH | |
| H | CN | H | OCH₃ | OCH₃ | N | |
| H | CN | H | OCH₃ | CH₃ | N | |
| H | CN | H | OCH₂CH₃ | NHCH₃ | N | |
| H | CN | CH₃ | OCH₃ | CH₃ | N | |
| 4-CH₃ | CN | H | OCH₃ | OCH₃ | CH | |
| 4-OCH₃ | CN | H | OCH₃ | OCH₃ | CH | |
| 6-CH₃ | CN | H | OCH₃ | OCH₃ | CH | |
| 6-OCH₃ | CN | H | OCH₃ | OCH₃ | CH | |
| 6-F | CN | H | OCH₃ | OCH₃ | CH | |
| 6-Cl | CN | H | OCH₃ | OCH₃ | CH | |
| H | P(O)(OCH₃)₂ | H | OCH₃ | OCH₃ | CH | |
| H | P(O)(OCH₃)₂ | H | OCH₃ | CH₃ | CH | |
| H | P(O)(OCH₃)₂ | H | Cl | OCH₃ | CH | |
| H | P(O)(OCH₃)₂ | H | CH₃ | CH₃ | CH | |
| H | P(O)(OCH₃)₂ | H | OCH₃ | OCH₃ | N | |
| H | P(O)(OCH₃)₂ | H | OCH₃ | CH₃ | N | |
| H | P(O)(OCH₃)₂ | H | OCH₂CH₃ | NHCH₃ | N | |
| H | P(O)(OCH₃)₂ | CH₃ | OCH₃ | CH₃ | N | |
| 4-CH₃ | P(O)(OCH₃)₂ | H | OCH₃ | OCH₃ | CH | |
| 4-OCH₃ | P(O)(OCH₃)₂ | H | OCH₃ | OCH₃ | CH | |
| 6-CH₃ | P(O)(OCH₃)₂ | H | OCH₃ | OCH₃ | CH | |
| 6-OCH₃ | P(O)(OCH₃)₂ | H | OCH₃ | OCH₃ | CH | |
| 6-F | P(O)(OCH₃)₂ | H | OCH₃ | OCH₃ | CH | |
| 6-Cl | P(O)(OCH₃)₂ | H | OCH₃ | OCH₃ | CH | |
| H | P(O)(OCH₂CH₃)₂ | H | OCH₃ | OCH₃ | CH | 108–111 |
| H | P(O)(OCH₂CH₃)₂ | H | OCH₃ | CH₃ | CH | |
| H | P(O)(OCH₂CH₃)₂ | H | Cl | OCH₃ | CH | |
| H | P(O)(OCH₂CH₃)₂ | H | CH₃ | CH₃ | CH | 110–114 |
| H | P(O)(OCH₂CH₃)₂ | H | OCH₃ | OCH₃ | N | |
| H | P(O)(OCH₂CH₃)₂ | H | OCH₃ | CH₃ | N | |
| H | P(O)(OCH₂CH₃)₂ | H | OCH₂CH₃ | NHCH₃ | N | |
| H | P(O)(OCH₂CH₃)₂ | CH₃ | OCH₃ | CH₃ | N | |
| 4-CH₃ | P(O)(OCH₂CH₃)₂ | H | OCH₃ | OCH₃ | CH | |
| 4-OCH₃ | P(O)(OCH₂CH₃)₂ | H | OCH₃ | OCH₃ | CH | |
| 6-CH₃ | P(O)(OCH₂CH₃)₂ | H | OCH₃ | OCH₃ | CH | |
| 6-OCH₃ | P(O)(OCH₂CH₃)₂ | H | OCH₃ | OCH₃ | CH | |
| 6-F | P(O)(OCH₂CH₃)₂ | H | OCH₃ | OCH₃ | CH | |
| 6-Cl | P(O)(OCH₂CH₃)₂ | H | OCH₃ | OCH₃ | CH | |
| H | P(S)(OCH₃)₂ | H | OCH₃ | OCH₃ | CH | |
| H | P(S)(OCH₃)₂ | H | OCH₃ | CH₃ | CH | |
| H | P(S)(OCH₃)₂ | H | Cl | OCH₃ | CH | |
| H | P(S)(OCH₃)₂ | H | CH₃ | CH₃ | CH | |
| H | P(S)(OCH₃)₂ | H | OCH₃ | OCH₃ | N | |
| H | P(S)(OCH₃)₂ | H | OCH₃ | CH₃ | N | |
| H | P(S)(OCH₃)₂ | H | OCH₂CH₃ | NHCH₃ | N | |
| H | P(S)(OCH₃)₂ | CH₃ | OCH₃ | CH₃ | N | |
| 4-CH₃ | P(S)(OCH₃)₂ | H | OCH₃ | OCH₃ | CH | |
| 4-OCH₃ | P(S)(OCH₃)₂ | H | OCH₃ | OCH₃ | CH | |
| 6-CH₃ | P(S)(OCH₃)₂ | H | OCH₃ | OCH₃ | CH | |
| 6-OCH₃ | P(S)(OCH₃)₂ | H | OCH₃ | OCH₃ | CH | |
| 6-F | P(S)(OCH₃)₂ | H | OCH₃ | OCH₃ | CH | |
| 6-Cl | P(S)(OCH₃)₂ | H | OCH₃ | OCH₃ | CH | |
| H | P(S)(OCH₂CH₃)₂ | H | OCH₃ | OCH₃ | CH | |
| H | P(S)(OCH₂CH₃)₂ | H | OCH₃ | CH₃ | CH | |
| H | P(S)(OCH₂CH₃)₂ | H | Cl | OCH₃ | CH | |
| H | P(S)(OCH₂CH₃)₂ | H | CH₃ | CH₃ | CH | |
| H | P(S)(OCH₂CH₃)₂ | H | OCH₃ | OCH₃ | N | |
| H | P(S)(OCH₂CH₃)₂ | H | OCH₃ | CH₃ | N | |
| H | P(S)(OCH₂CH₃)₂ | H | OCH₂CH₃ | NHCH₃ | N | |
| H | P(S)(OCH₂CH₃)₂ | CH₃ | OCH₃ | CH₃ | N | |

TABLE I-continued

General Formula 1

| R₁ | R₂ | R | X | Y | Z | m.p.(°C.) |
|---|---|---|---|---|---|---|
| 4-CH₃ | P(S)(OCH₂CH₃)₂ | H | OCH₃ | OCH₃ | CH | |
| 4-OCH₃ | P(S)(OCH₂CH₃)₂ | H | OCH₃ | OCH₃ | CH | |
| 6-CH₃ | P(S)(OCH₂CH₃)₂ | H | OCH₃ | OCH₃ | CH | |
| 6-OCH₃ | P(S)(OCH₂CH₃)₂ | H | OCH₃ | OCH₃ | CH | |
| 6-F | P(S)(OCH₂CH₃)₂ | H | OCH₃ | OCH₃ | CH | |
| 6-Cl | P(S)(OCH₂CH₃)₂ | H | OCH₃ | OCH₃ | CH | |
| H | CH₂F | H | OCH₃ | OCH₃ | CH | |
| H | CH₂F | H | OCH₃ | CH₃ | CH | |
| H | CH₂F | H | Cl | OCH₃ | CH | |
| H | CH₂F | H | CH₃ | CH₃ | CH | |
| H | CH₂F | H | OCH₃ | OCH₃ | N | |
| H | CH₂F | H | OCH₃ | CH₃ | N | |
| H | CH₂F | H | OCH₂CH₃ | NHCH₃ | N | |
| H | CH₂F | CH₃ | OCH₃ | CH₃ | N | |
| 4-CH₃ | CH₂F | H | OCH₃ | OCH₃ | CH | |
| 4-OCH₃ | CH₂F | H | OCH₃ | OCH₃ | CH | |
| 6-CH₃ | CH₂F | H | OCH₃ | OCH₃ | CH | |
| 6-OCH₃ | CH₂F | H | OCH₃ | OCH₃ | CH | |
| 6-F | CH₂F | H | OCH₃ | OCH₃ | CH | |
| 6-Cl | CH₂F | H | OCH₃ | OCH₃ | CH | |
| H | CF₂H | H | OCH₃ | OCH₃ | CH | |
| H | CF₂H | H | OCH₃ | CH₃ | CH | |
| H | CF₂H | H | Cl | OCH₃ | CH | |
| H | CF₂H | H | CH₃ | CH₃ | CH | |
| H | CF₂H | H | OCH₃ | OCH₃ | N | |
| H | CF₂H | H | OCH₃ | CH₃ | N | |
| H | CF₂H | H | OCH₂CH₃ | NHCH₃ | N | |
| H | CF₂H | CH₃ | OCH₃ | CH₃ | N | |
| 4-CH₃ | CF₂H | H | OCH₃ | OCH₃ | CH | |
| 4-OCH₃ | CF₂H | H | OCH₃ | OCH₃ | CH | |
| 6-CH₃ | CF₂H | H | OCH₃ | OCH₃ | CH | |
| 6-OCH₃ | CF₂H | H | OCH₃ | OCH₃ | CH | |
| 6-F | CF₂H | H | OCH₃ | OCH₃ | CH | |
| 6-Cl | CF₂H | H | OCH₃ | OCH₃ | CH | |
| H | CH₂Cl | H | OCH₃ | OCH₃ | CH | |
| H | CH₂Cl | H | OCH₃ | CH₃ | CH | |
| H | CH₂Cl | H | Cl | OCH₃ | CH | |
| H | CH₂Cl | H | CH₃ | CH₃ | CH | |
| H | CH₂Cl | H | OCH₃ | OCH₃ | N | |
| H | CH₂Cl | H | OCH₃ | CH₃ | N | |
| H | CH₂Cl | H | OCH₂CH₃ | NHCH₃ | N | |
| H | CH₂Cl | CH₃ | OCH₃ | CH₃ | N | |
| 4-CH₃ | CH₂Cl | H | OCH₃ | OCH₃ | CH | |
| 4-OCH₃ | CH₂Cl | H | OCH₃ | OCH₃ | CH | |
| 6-CH₃ | CH₂Cl | H | OCH₃ | OCH₃ | CH | |
| 6-OCH₃ | CH₂Cl | H | OCH₃ | OCH₃ | CH | |
| 6-F | CH₂Cl | H | OCH₃ | OCH₃ | CH | |
| 6-Cl | CH₂Cl | H | OCH₃ | OCH₃ | CH | |
| H | CCl₂H | H | OCH₃ | OCH₃ | CH | |
| H | CCl₂H | H | OCH₃ | CH₃ | CH | |
| H | CCl₂H | H | Cl | OCH₃ | CH | |
| H | CCl₂H | H | CH₃ | CH₃ | CH | |
| H | CCl₂H | H | OCH₃ | OCH₃ | N | |
| H | CCl₂H | H | OCH₃ | CH₃ | N | |
| H | CCl₂H | H | OCH₂CH₃ | NHCH₃ | N | |
| H | CCl₂H | CH₃ | OCH₃ | CH₃ | N | |
| 4-CH₃ | CCl₂H | H | OCH₃ | OCH₃ | CH | |
| 4-OCH₃ | CCl₂H | H | OCH₃ | OCH₃ | CH | |
| 6-CH₃ | CCl₂H | H | OCH₃ | OCH₃ | CH | |
| 6-OCH₃ | CCl₂H | H | OCH₃ | OCH₃ | CH | |
| 6-F | CCl₂H | H | OCH₃ | OCH₃ | CH | |
| 6-Cl | CCl₂H | H | OCH₃ | OCH₃ | CH | |
| H | CH₂CH₂Cl | H | OCH₃ | OCH₃ | CH | |
| H | CH₂CH₂Cl | H | OCH₃ | CH₃ | CH | |
| H | CH₂CH₂Cl | H | Cl | OCH₃ | CH | |
| H | CH₂CH₂Cl | H | CH₃ | CH₃ | CH | |
| H | CH₂CH₂Cl | H | OCH₃ | OCH₃ | N | |
| H | CH₂CH₂Cl | H | OCH₃ | CH₃ | N | |
| H | CH₂CH₂Cl | H | OCH₂CH₃ | NHCH₃ | N | |
| H | CH₂CH₂Cl | CH₃ | OCH₃ | CH₃ | N | |
| 4-CH₃ | CH₂CH₂Cl | H | OCH₃ | OCH₃ | CH | |
| 4-OCH₃ | CH₂CH₂Cl | H | OCH₃ | OCH₃ | CH | |
| 6-CH₃ | CH₂CH₂Cl | H | OCH₃ | OCH₃ | CH | |
| 6-OCH₃ | CH₂CH₂Cl | H | OCH₃ | OCH₃ | CH | |
| 6-F | CH₂CH₂Cl | H | OCH₃ | OCH₃ | CH | |
| 6-Cl | CH₂CH₂Cl | H | OCH₃ | OCH₃ | CH | |
| H | CH₂CH₂Br | H | OCH₃ | OCH₃ | CH | |
| H | CH₂CH₂Br | H | OCH₃ | CH₃ | CH | |
| H | CH₂CH₂Br | H | Cl | OCH₃ | CH | |
| H | CH₂CH₂Br | H | CH₃ | CH₃ | CH | |

TABLE I-continued

| | | General Formula 1 | | | | |
|---|---|---|---|---|---|---|
| $R_1$ | $R_2$ | R | X | Y | Z | m.p.(°C.) |
| H | $CH_2CH_2Br$ | H | $OCH_3$ | $OCH_3$ | N | |
| H | $CH_2CH_2Br$ | H | $OCH_3$ | $CH_3$ | N | |
| H | $CH_2CH_2Br$ | H | $OCH_2CH_3$ | $NHCH_3$ | N | |
| H | $CH_2CH_2Br$ | $CH_3$ | $OCH_3$ | $CH_3$ | N | |
| 4-$CH_3$ | $CH_2CH_2Br$ | H | $OCH_3$ | $OCH_3$ | CH | |
| 4-$OCH_3$ | $CH_2CH_2Br$ | H | $OCH_3$ | $OCH_3$ | CH | |
| 6-$CH_3$ | $CH_2CH_2Br$ | H | $OCH_3$ | $OCH_3$ | CH | |
| 6-$OCH_3$ | $CH_2CH_2Br$ | H | $OCH_3$ | $OCH_3$ | CH | |
| 6-F | $CH_2CH_2Br$ | H | $OCH_3$ | $OCH_3$ | CH | |
| 6-Cl | $CH_2CH_2Br$ | H | $OCH_3$ | $OCH_3$ | CH | |
| H | $CHFCH_3$ | H | $OCH_3$ | $OCH_3$ | CH | |
| H | $CHFCH_3$ | H | $OCH_3$ | $CH_3$ | CH | |
| H | $CHFCH_3$ | H | Cl | $OCH_3$ | CH | |
| H | $CHFCH_3$ | H | $CH_3$ | $CH_3$ | CH | |
| H | $CHFCH_3$ | H | $OCH_3$ | $OCH_3$ | N | |
| H | $CHFCH_3$ | H | $OCH_3$ | $CH_3$ | N | |
| H | $CHFCH_3$ | H | $OCH_2CH_3$ | $NHCH_3$ | N | |
| H | $CHFCH_3$ | $CH_3$ | $OCH_3$ | $CH_3$ | N | |
| 4-$CH_3$ | $CHFCH_3$ | H | $OCH_3$ | $OCH_3$ | CH | |
| 4-$OCH_3$ | $CHFCH_3$ | H | $OCH_3$ | $OCH_3$ | CH | |
| 6-$CH_3$ | $CHFCH_3$ | H | $OCH_3$ | $OCH_3$ | CH | |
| 6-$OCH_3$ | $CHFCH_3$ | H | $OCH_3$ | $OCH_3$ | CH | |
| 6-F | $CHFCH_3$ | H | $OCH_3$ | $OCH_3$ | CH | |
| 6-Cl | $CHFCH_3$ | H | $OCH_3$ | $OCH_3$ | CH | |
| H | $CHClCH_3$ | H | $OCH_3$ | $OCH_3$ | CH | |
| H | $CHClCH_3$ | H | $OCH_3$ | $CH_3$ | CH | |
| H | $CHClCH_3$ | H | Cl | $OCH_3$ | CH | |
| H | $CHClCH_3$ | H | $CH_3$ | $CH_3$ | CH | |
| H | $CHClCH_3$ | H | $OCH_3$ | $OCH_3$ | N | |
| H | $CHClCH_3$ | H | $OCH_3$ | $CH_3$ | N | |
| H | $CHClCH_3$ | H | $OCH_2CH_3$ | $NHCH_3$ | N | |
| H | $CHClCH_3$ | $CH_3$ | $OCH_3$ | $CH_3$ | N | |
| 4-$CH_3$ | $CHClCH_3$ | H | $OCH_3$ | $OCH_3$ | CH | |
| 4-$OCH_3$ | $CHClCH_3$ | H | $OCH_3$ | $OCH_3$ | CH | |
| 6-$CH_3$ | $CHClCH_3$ | H | $OCH_3$ | $OCH_3$ | CH | |
| 6-$OCH_3$ | $CHClCH_3$ | H | $OCH_3$ | $OCH_3$ | CH | |
| 6-F | $CHClCH_3$ | H | $OCH_3$ | $OCH_3$ | CH | |
| 6-Cl | $CHClCH_3$ | H | $OCH_3$ | $OCH_3$ | CH | |
| H | $CF_2CF_2H$ | H | $OCH_3$ | $OCH_3$ | CH | |
| H | $CF_2CF_2H$ | H | $OCH_3$ | $CH_3$ | CH | |
| H | $CF_2CF_2H$ | H | Cl | $OCH_3$ | CH | |
| H | $CF_2CF_2H$ | H | $CH_3$ | $CH_3$ | CH | |
| H | $CF_2CF_2H$ | H | $OCH_3$ | $OCH_3$ | N | |
| H | $CF_2CF_2H$ | H | $OCH_3$ | $CH_3$ | N | |
| H | $CF_2CF_2H$ | H | $OCH_2CH_3$ | $NHCH_3$ | N | |
| H | $CF_2CF_2H$ | $CH_3$ | $OCH_3$ | $CH_3$ | N | |
| 4-$CH_3$ | $CF_2CF_2H$ | H | $OCH_3$ | $OCH_3$ | CH | |
| 4-$OCH_3$ | $CF_2CF_2H$ | H | $OCH_3$ | $OCH_3$ | CH | |
| 6-$CH_3$ | $CF_2CF_2H$ | H | $OCH_3$ | $OCH_3$ | CH | |
| 6-$OCH_3$ | $CF_2CF_2H$ | H | $OCH_3$ | $OCH_3$ | CH | |
| 6-F | $CF_2CF_2H$ | H | $OCH_3$ | $OCH_3$ | CH | |
| 6-Cl | $CF_2CF_2H$ | H | $OCH_3$ | $OCH_3$ | CH | |

TABLE II

| | | General Formula 2 | | | | |
|---|---|---|---|---|---|---|
| $R_1$ | $R_3$ | R | X | Y | Z | m.p. (°C.) |
| H | $SOCH_3$ | H | $OCH_3$ | $OCH_3$ | CH | |
| H | $SOCH_3$ | H | $OCH_3$ | $CH_3$ | CH | |
| H | $SOCH_3$ | H | Cl | $OCH_3$ | CH | |
| H | $SOCH_3$ | H | $CH_3$ | $CH_3$ | CH | |
| H | $SOCH_3$ | H | $OCH_3$ | $OCH_3$ | N | |
| H | $SOCH_3$ | H | $OCH_3$ | $CH_3$ | N | |
| H | $SOCH_3$ | $CH_3$ | $OCH_3$ | $CH_3$ | N | |
| 4-$CH_3$ | $SOCH_3$ | H | $OCH_3$ | $OCH_3$ | CH | |
| 4-Cl | $SOCH_3$ | H | $OCH_3$ | $OCH_3$ | CH | |
| 6-$CH_3$ | $SOCH_3$ | H | $OCH_3$ | $OCH_3$ | CH | |
| 6-$OCH_3$ | $SOCH_3$ | H | $OCH_3$ | $OCH_3$ | CH | |
| 6-F | $SOCH_3$ | H | $OCH_3$ | $OCH_3$ | CH | |
| 6-Cl | $SOCH_3$ | H | $OCH_3$ | $OCH_3$ | CH | |
| H | $SOCH_2CH_3$ | H | $OCH_3$ | $OCH_3$ | CH | |
| H | $SOCH_2CH_3$ | H | $OCH_3$ | $CH_3$ | CH | |
| H | $SOCH_2CH_3$ | H | Cl | $OCH_3$ | CH | |
| H | $SOCH_2CH_3$ | H | $CH_3$ | $CH_3$ | CH | |
| H | $SOCH_2CH_3$ | H | $OCH_3$ | $OCH_3$ | N | |
| H | $SOCH_2CH_3$ | H | $OCH_3$ | $CH_3$ | N | |
| H | $SOCH_2CH_3$ | $CH_3$ | $OCH_3$ | $CH_3$ | N | |
| 4-$CH_3$ | $SOCH_2CH_3$ | H | $OCH_3$ | $OCH_3$ | CH | |

TABLE II-continued

General Formula 2

| R₁ | R₃ | R | X | Y | Z | m.p. (°C.) |
|---|---|---|---|---|---|---|
| 4-Cl | SOCH₂CH₃ | H | OCH₃ | OCH₃ | CH | |
| 6-CH₃ | SOCH₂CH₃ | H | OCH₃ | OCH₃ | CH | |
| 6-OCH₃ | SOCH₂CH₃ | H | OCH₃ | OCH₃ | CH | |
| 6-F | SOCH₂CH₃ | H | OCH₃ | OCH₃ | CH | |
| 6-Cl | SOCH₂CH₃ | H | OCH₃ | OCH₃ | CH | |
| H | SOCH₂CH₂CH₃ | H | OCH₃ | OCH₃ | CH | |
| H | SOCH₂CH₂CH₃ | H | OCH₃ | CH₃ | CH | |
| H | SOCH₂CH₂CH₃ | H | Cl | OCH₃ | CH | |
| H | SOCH₂CH₂CH₃ | H | CH₃ | CH₃ | CH | |
| H | SOCH₂CH₂CH₃ | H | OCH₃ | OCH₃ | N | |
| H | SOCH₂CH₂CH₃ | H | OCH₃ | CH₃ | N | |
| H | SOCH₂CH₂CH₃ | CH₃ | OCH₃ | CH₃ | N | |
| 4-CH₃ | SOCH₂CH₂CH₃ | H | OCH₃ | OCH₃ | CH | |
| 4-Cl | SOCH₂CH₂CH₃ | H | OCH₃ | OCH₃ | CH | |
| 6-CH₃ | SOCH₂CH₂CH₃ | H | OCH₃ | OCH₃ | CH | |
| 6-OCH₃ | SOCH₂CH₂CH₃ | H | OCH₃ | OCH₃ | CH | |
| 6-F | SOCH₂CH₂CH₃ | H | OCH₃ | OCH₃ | CH | |
| 6-Cl | SOCH₂CH₂CH₃ | H | OCH₃ | OCH₃ | CH | |
| H | SOCH₂CH₂CH₂CH₃ | H | OCH₃ | OCH₃ | CH | |
| H | SOCH₂CH₂CH₂CH₃ | H | OCH₃ | CH₃ | CH | |
| H | SOCH₂CH₂CH₂CH₃ | H | Cl | OCH₃ | CH | |
| H | SOCH₂CH₂CH₂CH₃ | H | CH₃ | CH₃ | CH | |
| H | SOCH₂CH₂CH₂CH₃ | H | OCH₃ | OCH₃ | N | |
| H | SOCH₂CH₂CH₂CH₃ | H | OCH₃ | CH₃ | N | |
| H | SOCH₂CH₂CH₂CH₃ | CH₃ | OCH₃ | CH₃ | N | |
| 4-CH₃ | SOCH₂CH₂CH₂CH₃ | H | OCH₃ | OCH₃ | CH | |
| 4-Cl | SOCH₂CH₂CH₂CH₃ | H | OCH₃ | OCH₃ | CH | |
| 6-CH₃ | SOCH₂CH₂CH₂CH₃ | H | OCH₃ | OCH₃ | CH | |
| 6-OCH₃ | SOCH₂CH₂CH₂CH₃ | H | OCH₃ | OCH₃ | CH | |
| 6-F | SOCH₂CH₂CH₂CH₃ | H | OCH₃ | OCH₃ | CH | |
| 6-Cl | SOCH₂CH₂CH₂CH₃ | H | OCH₃ | OCH₃ | CH | |
| H | SOCH(CH₃)₂ | H | OCH₃ | OCH₃ | CH | |
| H | SOCH(CH₃)₂ | H | OCH₃ | CH₃ | CH | |
| H | SOCH(CH₃)₂ | H | Cl | OCH₃ | CH | |
| H | SOCH(CH₃)₂ | H | CH₃ | CH₃ | CH | |
| H | SOCH(CH₃)₂ | H | OCH₃ | OCH₃ | N | |
| H | SOCH(CH₃)₂ | H | OCH₃ | CH₃ | N | |
| H | SOCH(CH₃)₂ | CH₃ | OCH₃ | CH₃ | N | |
| 4-CH₃ | SOCH(CH₃)₂ | H | OCH₃ | OCH₃ | CH | |
| 4-Cl | SOCH(CH₃)₂ | H | OCH₃ | OCH₃ | CH | |
| 6-CH₃ | SOCH(CH₃)₂ | H | OCH₃ | OCH₃ | CH | |
| 6-OCH₃ | SOCH(CH₃)₂ | H | OCH₃ | OCH₃ | CH | |
| 6-F | SOCH(CH₃)₂ | H | OCH₃ | OCH₃ | CH | |
| 6-Cl | SOCH(CH₃)₂ | H | OCH₃ | OCH₃ | CH | |
| H | S—cyclopropyl | H | OCH₃ | OCH₃ | CH | |
| H | S—cyclopropyl | H | OCH₃ | CH₃ | CH | |
| H | S—cyclopropyl | H | Cl | OCH₃ | CH | |
| H | S—cyclopropyl | H | CH₃ | CH₃ | CH | |
| H | S—cyclopropyl | H | OCH₃ | OCH₃ | N | |
| H | S—cyclopropyl | H | OCH₃ | CH₃ | N | |
| H | S—cyclopropyl | H | OCH₂CH₃ | NHCH₃ | N | |
| H | S—cyclopropyl | CH₃ | OCH₃ | CH₃ | N | |
| 4-CH₃ | S—cyclopropyl | H | OCH₃ | OCH₃ | CH | |
| 4-Cl | S—cyclopropyl | H | OCH₃ | OCH₃ | CH | |
| 6-CH₃ | S—cyclopropyl | H | OCH₃ | OCH₃ | CH | |
| 6-OCH₃ | S—cyclopropyl | H | OCH₃ | OCH₃ | CH | |
| 6-F | S—cyclopropyl | H | OCH₃ | OCH₃ | CH | |
| 6-Cl | S—cyclopropyl | H | OCH₃ | OCH₃ | CH | |
| H | SO—cyclopropyl | H | OCH₃ | OCH₃ | CH | |
| H | SO—cyclopropyl | H | OCH₃ | CH₃ | CH | |
| H | SO—cyclopropyl | H | Cl | OCH₃ | CH | |
| H | SO—cyclopropyl | H | CH₃ | CH₃ | CH | |
| H | SO—cyclopropyl | H | OCH₃ | OCH₃ | N | |
| H | SO—cyclopropyl | H | OCH₃ | CH₃ | N | |
| H | SO—cyclopropyl | H | OCH₂CH₃ | NHCH₃ | N | |
| H | SO—cyclopropyl | CH₃ | OCH₃ | CH₃ | N | |
| 4-CH₃ | SO—cyclopropyl | H | OCH₃ | OCH₃ | CH | |
| 4-Cl | SO—cyclopropyl | H | OCH₃ | OCH₃ | CH | |
| 6-CH₃ | SO—cyclopropyl | H | OCH₃ | OCH₃ | CH | |
| 6-OCH₃ | SO—cyclopropyl | H | OCH₃ | OCH₃ | CH | |
| 6-F | SO—cyclopropyl | H | OCH₃ | OCH₃ | CH | |
| 6-Cl | SO—cyclopropyl | H | OCH₃ | OCH₃ | CH | |
| H | SO₂—cyclopropyl | H | OCH₃ | OCH₃ | CH | |
| H | SO₂—cyclopropyl | H | OCH₃ | CH₃ | CH | |
| H | SO₂—cyclopropyl | H | Cl | OCH₃ | CH | |
| H | SO₂—cyclopropyl | H | CH₃ | CH₃ | CH | |
| H | SO₂—cyclopropyl | H | OCH₃ | OCH₃ | N | |
| H | SO₂—cyclopropyl | H | OCH₃ | CH₃ | N | |
| H | SO₂—cyclopropyl | H | OCH₂CH₃ | NHCH₃ | N | |
| H | SO₂—cyclopropyl | CH₃ | OCH₃ | CH₃ | N | |

TABLE II-continued

General Formula 2

| R₁ | R₃ | R | X | Y | Z | m.p. (°C.) |
|---|---|---|---|---|---|---|
| 4-CH₃ | SO₂—cyclopropyl | H | OCH₃ | OCH₃ | CH | |
| 4-Cl | SO₂—cyclopropyl | H | OCH₃ | OCH₃ | CH | |
| 6-CH₃ | SO₂—cyclopropyl | H | OCH₃ | OCH₃ | CH | |
| 6-OCH₃ | SO₂—cyclopropyl | H | OCH₃ | OCH₃ | CH | |
| 6-F | SO₂—cyclopropyl | H | OCH₃ | OCH₃ | CH | |
| 6-Cl | SO₂—cyclopropyl | H | OCH₃ | OCH₃ | CH | |
| H | OSO₂CH₃ | H | OCH₃ | OCH₃ | CH | |
| H | OSO₂CH₃ | H | OCH₃ | CH₃ | CH | |
| H | OSO₂CH₃ | H | Cl | OCH₃ | CH | |
| H | OSO₂CH₃ | H | CH₃ | CH₃ | CH | |
| H | OSO₂CH₃ | H | OCH₃ | OCH₃ | N | |
| H | OSO₂CH₃ | H | OCH₃ | CH₃ | N | |
| H | OSO₂CH₃ | H | OCH₂CH₃ | NHCH₃ | N | |
| H | OSO₂CH₃ | CH₃ | OCH₃ | CH₃ | N | |
| 4-CH₃ | OSO₂CH₃ | H | OCH₃ | OCH₃ | CH | |
| 4-Cl | OSO₂CH₃ | H | OCH₃ | OCH₃ | CH | |
| 6-CH₃ | OSO₂CH₃ | H | OCH₃ | OCH₃ | CH | |
| 6-OCH₃ | OSO₂CH₃ | H | OCH₃ | OCH₃ | CH | |
| 6-F | OSO₂CH₃ | H | OCH₃ | OCH₃ | CH | |
| 6-Cl | OSO₂CH₃ | H | OCH₃ | OCH₃ | CH | |
| H | OSO₂CH₂CH₃ | H | OCH₃ | OCH₃ | CH | |
| H | OSO₂CH₂CH₃ | H | OCH₃ | CH₃ | CH | |
| H | OSO₂CH₂CH₃ | H | Cl | OCH₃ | CH | |
| H | OSO₂CH₂CH₃ | H | CH₃ | CH₃ | CH | |
| H | OSO₂CH₂CH₃ | H | OCH₃ | OCH₃ | N | |
| H | OSO₂CH₂CH₃ | H | OCH₃ | CH₃ | N | |
| H | OSO₂CH₂CH₃ | H | OCH₂CH₃ | NHCH₃ | N | |
| H | OSO₂CH₂CH₃ | CH₃ | OCH₃ | CH₃ | N | |
| 4-CH₃ | OSO₂CH₂CH₃ | H | OCH₃ | OCH₃ | CH | |
| 4-Cl | OSO₂CH₂CH₃ | H | OCH₃ | OCH₃ | CH | |
| 6-CH₃ | OSO₂CH₂CH₃ | H | OCH₃ | OCH₃ | CH | |
| 6-OCH₃ | OSO₂CH₂CH₃ | H | OCH₃ | OCH₃ | CH | |
| 6-F | OSO₂CH₂CH₃ | H | OCH₃ | OCH₃ | CH | |
| 6-Cl | OSO₂CH₂CH₃ | H | OCH₃ | OCH₃ | CH | |
| H | OSO₂CF₃ | H | OCH₃ | OCH₃ | CH | |
| H | OSO₂CF₃ | H | OCH₃ | CH₃ | CH | |
| H | OSO₂CF₃ | H | Cl | OCH₃ | CH | |
| H | OSO₂CF₃ | H | CH₃ | CH₃ | CH | |
| H | OSO₂CF₃ | H | OCH₃ | OCH₃ | N | |
| H | OSO₂CF₃ | H | OCH₃ | CH₃ | N | |
| H | OSO₂CF₃ | H | OCH₂CH₃ | NHCH₃ | N | |
| H | OSO₂CF₃ | CH₃ | OCH₃ | CH₃ | N | |
| 4-CH₃ | OSO₂CF₃ | H | OCH₃ | OCH₃ | CH | |
| 4-Cl | OSO₂CF₃ | H | OCH₃ | OCH₃ | CH | |
| 6-CH₃ | OSO₂CF₃ | H | OCH₃ | OCH₃ | CH | |
| 6-OCH₃ | OSO₂CF₃ | H | OCH₃ | OCH₃ | CH | |
| 6-F | OSO₂CF₃ | H | OCH₃ | OCH₃ | CH | |
| 6-Cl | OSO₂CF₃ | H | OCO₃ | OCH₃ | CH | |
| H | OSO₂CCl₃ | H | OCH₃ | OCH₃ | CH | |
| H | OSO₂CCl₃ | H | OCH₃ | CH₃ | CH | |
| H | OSO₂CCl₃ | H | Cl | OCH₃ | CH | |
| H | OSO₂CCl₃ | H | CH₃ | CH₃ | CH | |
| H | OSO₂CCl₃ | H | OCH₃ | OCH₃ | N | |
| H | OSO₂CCl₃ | H | OCH₃ | CH₃ | N | |
| H | OSO₂CCl₃ | H | OCH₂CH₃ | NHCH₃ | N | |
| H | OSO₂CCl₃ | CH₃ | OCH₃ | CH₃ | N | |
| 4-CH₃ | OSO₂CCl₃ | H | OCH₃ | OCH₃ | CH | |
| 4-Cl | OSO₂CCl₃ | H | OCH₃ | OCH₃ | CH | |
| 6-CH₃ | OSO₂CCl₃ | H | OCH₃ | OCH₃ | CH | |
| 6-OCH₃ | OSO₂CCl₃ | H | OCH₃ | OCH₃ | CH | |
| 6-F | OSO₂CCl₃ | H | OCH₃ | OCH₃ | CH | |
| 6-Cl | OSO₂CCl₃ | H | OCH₃ | OCH₃ | CH | |
| H | OSO₂CH₂CH₂CH₃ | H | OCH₃ | OCH₃ | CH | |
| H | OSO₂CH₂CH₂CH₃ | H | OCH₃ | CH₃ | CH | |
| H | OSO₂CH₂CH₂CH₃ | H | Cl | OCH₃ | CH | |
| H | OSO₂CH₂CH₂CH₃ | H | CH₃ | CH₃ | CH | |
| H | OSO₂CH₂CH₂CH₃ | H | OCH₃ | OCH₃ | N | |
| H | OSO₂CH₂CH₂CH₃ | H | OCH₃ | CH₃ | N | |
| H | OSO₂CH₂CH₂CH₃ | H | OCH₂CH₃ | NHCH₃ | N | |
| H | OSO₂CH₂CH₂CH₃ | CH₃ | OCH₃ | CH₃ | N | |
| 4-CH₃ | OSO₂CH₂CH₂CH₃ | H | OCH₃ | OCH₃ | CH | |
| 4-Cl | OSO₂CH₂CH₂CH₃ | H | OCH₃ | OCH₃ | CH | |
| 6-CH₃ | OSO₂CH₂CH₂CH₃ | H | OCH₃ | OCH₃ | CH | |
| 6-OCH₃ | OSO₂CH₂CH₂CH₃ | H | OCH₃ | OCH₃ | CH | |
| 6-F | OSO₂CH₂CH₂CH₃ | H | OCH₃ | OCH₃ | CH | |
| 6-Cl | OSO₂CH₂CH₂CH₃ | H | OCO₃ | OCH₃ | CH | |
| H | SO₂OCH₂CF₃ | H | OCH₃ | OCH₃ | CH | |
| H | SO₂OCH₂CF₃ | H | OCH₃ | CH₃ | CH | |
| H | SO₂OCH₂CF₃ | H | Cl | OCH₃ | CH | |
| H | SO₂OCH₂CF₃ | H | CH₃ | CH₃ | CH | |

TABLE II-continued

General Formula 2

| R₁ | R₃ | R | X | Y | Z | m.p. (°C.) |
|---|---|---|---|---|---|---|
| H | SO₂OCH₂CF₃ | H | OCH₃ | OCH₃ | N | |
| H | SO₂OCH₂CF₃ | H | OCH₃ | CH₃ | N | |
| H | SO₂OCH₂CF₃ | H | OCH₂CH₃ | NHCH₃ | N | |
| H | SO₂OCH₂CF₃ | CH₃ | OCH₃ | CH₃ | N | |
| 4-CH₃ | SO₂OCH₂CF₃ | H | OCH₃ | OCH₃ | CH | |
| 4-Cl | SO₂OCH₂CF₃ | H | OCH₃ | OCH₃ | CH | |
| 6-CH₃ | SO₂OCH₂CF₃ | H | OCH₃ | OCH₃ | CH | |
| 6-OCH₃ | SO₂OCH₂CF₃ | H | OCH₃ | OCH₃ | CH | |
| 6-F | SO₂OCH₂CF₃ | H | OCH₃ | OCH₃ | CH | |
| 6-Cl | SO₂OCH₂CF₃ | H | OCH₃ | OCH₃ | CH | |
| H | P(O)(OCH₃)₂ | H | OCH₃ | OCH₃ | CH | |
| H | P(O)(OCH₃)₂ | H | OCH₃ | CH₃ | CH | |
| H | P(O)(OCH₃)₂ | H | Cl | OCH₃ | CH | |
| H | P(O)(OCH₃)₂ | H | CH₃ | CH₃ | CH | |
| H | P(O)(OCH₃)₂ | H | OCH₃ | OCH₃ | N | |
| H | P(O)(OCH₃)₂ | H | OCH₃ | CH₃ | N | |
| H | P(O)(OCH₃)₂ | H | OCH₂CH₃ | NHCH₃ | N | |
| H | P(O)(OCH₃)₂ | CH₃ | OCH₃ | CH₃ | N | |
| 4-CH₃ | P(O)(OCH₃)₂ | H | OCH₃ | OCH₃ | CH | |
| 4-Cl | P(O)(OCH₃)₂ | H | OCH₃ | OCH₃ | CH | |
| 6-CH₃ | P(O)(OCH₃)₂ | H | OCH₃ | OCH₃ | CH | |
| 6-OCH₃ | P(O)(OCH₃)₂ | H | OCH₃ | OCH₃ | CH | |
| 6-F | P(O)(OCH₃)₂ | H | OCH₃ | OCH₃ | CH | |
| 6-Cl | P(O)(OCH₃)₂ | H | OCO₃ | OCH₃ | CH | |
| H | CN | H | OCH₃ | OCH₃ | CH | |
| H | CN | H | OCH₃ | CH₃ | CH | |
| H | CN | H | Cl | OCH₃ | CH | |
| H | CN | H | CH₃ | CH₃ | CH | |
| H | CN | H | OCH₃ | OCH₃ | N | |
| H | CN | H | OCH₃ | CH₃ | N | |
| H | CN | H | OCH₂CH₃ | NHCH₃ | N | |
| H | CN | CH₃ | OCH₃ | CH₃ | N | |
| 4-CH₃ | CN | H | OCH₃ | OCH₃ | CH | |
| 4-Cl | CN | H | OCH₃ | OCH₃ | CH | |
| 6-CH₃ | CN | H | OCH₃ | OCH₃ | CH | |
| 6-OCH₃ | CN | H | OCH₃ | OCH₃ | CH | |
| 6-F | CN | H | OCH₃ | OCH₃ | CH | |
| 6-Cl | CN | H | OCH₃ | OCH₃ | CH | |
| H | CH₂F | H | OCH₃ | OCH₃ | CH | |
| H | CH₂F | H | OCH₃ | CH₃ | CH | |
| H | CH₂F | H | Cl | OCH₃ | CH | |
| H | CH₂F | H | CH₃ | CH₃ | CH | |
| H | CH₂F | H | OCH₃ | OCH₃ | N | |
| H | CH₂F | H | OCH₃ | CH₃ | N | |
| H | CH₂F | H | OCH₂CH₃ | NHCH₃ | N | |
| H | CH₂F | CH₃ | OCH₃ | CH₃ | N | |
| 4-CH₃ | CH₂F | H | OCH₃ | OCH₃ | CH | |
| 4-Cl | CH₂F | H | OCH₃ | OCH₃ | CH | |
| 6-CH₃ | CH₂F | H | OCH₃ | OCH₃ | CH | |
| 6-OCH₃ | CH₂F | H | OCH₃ | OCH₃ | CH | |
| 6-F | CH₂F | H | OCH₃ | OCH₃ | CH | |
| 6-Cl | CH₂F | H | OCO₃ | OCH₃ | CH | |
| H | CF₂H | H | OCH₃ | OCH₃ | CH | |
| H | CH₂H | H | OCH₃ | CH₃ | CH | |
| H | CF₂H | H | Cl | OCH₃ | CH | |
| H | CF₂H | H | CH₃ | CH₃ | CH | |
| H | CF₂H | H | OCH₃ | OCH₃ | N | |
| H | CF₂H | H | OCH₃ | CH₃ | N | |
| H | CF₂H | H | OCH₂CH₃ | NHCH₃ | N | |
| H | CF₂H | CH₃ | OCH₃ | CH₃ | N | |
| 4-CH₃ | CF₂H | H | OCH₃ | OCH₃ | CH | |
| 4-Cl | CF₂H | H | OCH₃ | OCH₃ | CH | |
| 6-CH₃ | CF₂H | H | OCH₃ | OCH₃ | CH | |
| 6-OCH₃ | CF₂H | H | OCH₃ | OCH₃ | CH | |
| 6-F | CF₂H | H | OCH₃ | OCH₃ | CH | |
| 6-Cl | CF₂H | H | OCH₃ | OCH₃ | CH | |

TABLE III

General Formula 3

| R₁ | R₄ | R | X | Y | Z | m.p. (°C.) |
|---|---|---|---|---|---|---|
| H | SOCH₃ | H | OCH₃ | OCH₃ | CH | |
| H | SOCH₃ | H | OCH₃ | CH₃ | CH | |
| H | SOCH₃ | H | Cl | OCH₃ | CH | |
| H | SOCH₃ | H | CH₃ | CH₃ | CH | |
| H | SOCH₃ | H | OCH₃ | OCH₃ | N | |
| H | SOCH₃ | H | OCH₃ | CH₃ | N | |
| H | SOCH₃ | H | OCH₃ | CH₃ | N | |

TABLE III-continued

General Formula 3

| R₁ | R₄ | R | X | Y | Z | m.p. (°C.) |
|---|---|---|---|---|---|---|
| 2-Cl | SOCH₃ | H | OCH₃ | OCH₃ | CH | |
| 2-F | SOCH₃ | H | OCH₃ | OCH₃ | CH | |
| 6-CH₃ | SOCH₃ | H | OCH₃ | OCH₃ | CH | |
| 6-OCH₃ | SOCH₃ | H | OCH₃ | OCH₃ | CH | |
| 6-F | SOCH₃ | H | OCH₃ | OCH₃ | CH | |
| 6-Cl | SOCH₃ | H | OCH₃ | OCH₃ | CH | |
| H | SOCH₂CH₃ | H | OCH₃ | OCH₃ | CH | |
| H | SOCH₂CH₃ | H | OCH₃ | CH₃ | CH | |
| H | SOCH₂CH₃ | H | Cl | OCH₃ | CH | |
| H | SOCH₂CH₃ | H | CH₃ | CH₃ | CH | |
| H | SOCH₂CH₃ | H | OCH₃ | OCH₃ | N | |
| H | SOCH₂CH₃ | H | OCH₃ | CH₃ | N | |
| H | SOCH₂CH₃ | CH₃ | OCH₃ | CH₃ | N | |
| 2-Cl | SOCH₂CH₃ | H | OCH₃ | OCH₃ | CH | |
| 2-F | SOCH₂CH₃ | H | OCH₃ | OCH₃ | CH | |
| 6-CH₃ | SOCH₂CH₃ | H | OCH₃ | OCH₃ | CH | |
| 6-OCH₃ | SOCH₂CH₃ | H | OCH₃ | OCH₃ | CH | |
| 6-F | SOCH₂CH₃ | H | OCH₃ | OCH₃ | CH | |
| 6-Cl | SOCH₂CH₃ | H | OCH₃ | OCH₃ | CH | |
| H | SOCH₂CH₂CH₃ | H | OCH₃ | OCH₃ | CH | |
| H | SOCH₂CH₂CH₃ | H | OCH₃ | CH₃ | CH | |
| H | SOCH₂CH₂CH₃ | H | Cl | OCH₃ | CH | |
| H | SOCH₂CH₂CH₃ | H | CH₃ | CH₃ | CH | |
| H | SOCH₂CH₂CH₃ | H | OCH₃ | OCH₃ | N | |
| H | SOCH₂CH₂CH₃ | H | OCH₃ | CH₃ | N | |
| H | SOCH₂CH₂CH₃ | CH₃ | OCH₃ | CH₃ | N | |
| 2-Cl | SOCH₂CH₂CH₃ | H | OCH₃ | OCH₃ | CH | |
| 2-F | SOCH₂CH₂CH₃ | H | OCH₃ | OCH₃ | CH | |
| 6-CH₃ | SOCH₂CH₂CH₃ | H | OCH₃ | OCH₃ | CH | |
| 6-OCH₃ | SOCH₂CH₂CH₃ | H | OCH₃ | OCH₃ | CH | |
| 6-F | SOCH₂CH₂CH₃ | H | OCH₃ | OCH₃ | CH | |
| 6-Cl | SOCH₂CH₂CH₃ | H | OCH₃ | OCH₃ | CH | |
| H | SOCH₂CH₂CH₂CH₃ | H | OCH₃ | OCH₃ | CH | |
| H | SOCH₂CH₂CH₂CH₃ | H | OCH₃ | CH₃ | CH | |
| H | SOCH₂CH₂CH₂CH₃ | H | Cl | OCH₃ | CH | |
| H | SOCH₂CH₂CH₂CH₃ | H | CH₃ | CH₃ | CH | |
| H | SOCH₂CH₂CH₂CH₃ | H | OCH₃ | OCH₃ | N | |
| H | SOCH₂CH₂CH₂CH₃ | H | OCH₃ | CH₃ | N | |
| H | SOCH₂CH₂CH₂CH₃ | CH₃ | OCH₃ | CH₃ | N | |
| 2-Cl | SOCH₂CH₂CH₂CH₃ | H | OCH₃ | OCH₃ | CH | |
| 2-F | SOCH₂CH₂CH₂CH₃ | H | OCH₃ | OCH₃ | CH | |
| 6-CH₃ | SOCH₂CH₂CH₂CH₃ | H | OCH₃ | OCH₃ | CH | |
| 6-OCH₃ | SOCH₂CH₂CH₂CH₃ | H | OCH₃ | OCH₃ | CH | |
| 6-F | SOCH₂CH₂CH₂CH₃ | H | OCH₃ | OCH₃ | CH | |
| 6-Cl | SOCH₂CH₂CH₂CH₃ | H | OCH₃ | OCH₃ | CH | |
| H | SOCH(CH₃)₂ | H | OCH₃ | OCH₃ | CH | |
| H | SOCH(CH₃)₂ | H | OCH₃ | CH₃ | CH | |
| H | SOCH(CH₃)₂ | H | Cl | OCH₃ | CH | |
| H | SOCH(CH₃)₂ | H | CH₃ | CH₃ | CH | |
| H | SOCH(CH₃)₂ | H | OCH₃ | OCH₃ | N | |
| H | SOCH(CH₃)₂ | H | OCH₃ | CH₃ | N | |
| H | SOCH(CH₃)₂ | CH₃ | OCH₃ | CH₃ | N | |
| 2-Cl | SOCH(CH₃)₂ | H | OCH₃ | OCH₃ | CH | |
| 2-F | SOCH(CH₃)₂ | H | OCH₃ | OCH₃ | CH | |
| 6-CH₃ | SOCH(CH₃)₂ | H | OCH₃ | OCH₃ | CH | |
| 6-OCH₃ | SOCH(CH₃)₂ | H | OCH₃ | OCH₃ | CH | |
| 6-F | SOCH(CH₃)₂ | H | OCH₃ | OCH₃ | CH | |
| 6-Cl | SOCH(CH₃)₂ | H | OCH₃ | OCH₃ | CH | |
| H | S—cyclopropyl | H | OCH₃ | OCH₃ | CH | |
| H | S—cyclopropyl | H | OCH₃ | CH₃ | CH | |
| H | S—cyclopropyl | H | Cl | OCH₃ | CH | |
| H | S—cyclopropyl | H | CH₃ | CH₃ | CH | |
| H | S—cyclopropyl | H | OCH₃ | OCH₃ | N | |
| H | S—cyclopropyl | H | OCH₃ | CH₃ | N | |
| H | S—cyclopropyl | H | OCH₂CH₃ | NHCH₃ | N | |
| H | S—cyclopropyl | CH₃ | OCH₃ | CH₃ | N | |
| 2-Cl | S—cyclopropyl | H | OCH₃ | OCH₃ | CH | |
| 2-F | S—cyclopropyl | H | OCH₃ | OCH₃ | CH | |
| 6-CH₃ | S—cyclopropyl | H | OCH₃ | OCH₃ | CH | |
| 6-OCH₃ | S—cyclopropyl | H | OCH₃ | OCH₃ | CH | |
| 6-F | S—cyclopropyl | H | OCH₃ | OCH₃ | CH | |
| 6-Cl | S—cyclopropyl | H | OCH₃ | OCH₃ | CH | |
| H | SO—cyclopropyl | H | OCH₃ | OCH₃ | CH | |
| H | SO—cyclopropyl | H | OCH₃ | CH₃ | CH | |
| H | SO—cyclopropyl | H | Cl | OCH₃ | CH | |
| H | SO—cyclopropyl | H | CH₃ | CH₃ | CH | |
| H | SO—cyclopropyl | H | OCH₃ | OCH₃ | N | |
| H | SO—cyclopropyl | H | OCH₃ | CH₃ | N | |
| H | SO—cyclopropyl | H | OCH₂CH₃ | NHCH₃ | N | |
| H | SO—cyclopropyl | CH₃ | OCH₃ | CH₃ | N | |

TABLE III-continued

General Formula 3

| R₁ | R₄ | R | X | Y | Z | m.p. (°C.) |
|---|---|---|---|---|---|---|
| 2-Cl | SO—cyclopropyl | H | OCH₃ | OCH₃ | CH | |
| 2-F | SO—cyclopropyl | H | OCH₃ | OCH₃ | CH | |
| 6-CH₃ | SO—cyclopropyl | H | OCH₃ | OCH₃ | CH | |
| 6-OCH₃ | SO—cyclopropyl | H | OCH₃ | OCH₃ | CH | |
| 6-F | SO—cyclopropyl | H | OCH₃ | OCH₃ | CH | |
| 6-Cl | SO—cyclopropyl | H | OCH₃ | OCH₃ | CH | |
| H | SO₂—cyclopropyl | H | OCH₃ | OCH₃ | CH | |
| H | SO₂—cyclopropyl | H | OCH₃ | CH₃ | CH | |
| H | SO₂—cyclopropyl | H | Cl | OCH₃ | CH | |
| H | SO₂—cyclopropyl | H | CH₃ | CH₃ | CH | |
| H | SO₂—cyclopropyl | H | OCH₃ | OCH₃ | N | |
| H | SO₂—cyclopropyl | H | OCH₃ | CH₃ | N | |
| H | SO₂—cyclopropyl | H | OCH₂CH₃ | NHCH₃ | N | |
| H | SO₂—cyclopropyl | CH₃ | OCH₃ | CH₃ | N | |
| 2-Cl | SO₂—cyclopropyl | H | OCH₃ | OCH₃ | CH | |
| 2-F | SO₂—cyclopropyl | H | OCH₃ | OCH₃ | CH | |
| 6-CH₃ | SO₂—cyclopropyl | H | OCH₃ | OCH₃ | CH | |
| 6-OCH₃ | SO₂—cyclopropyl | H | OCH₃ | OCH₃ | CH | |
| 6-F | SO₂—cyclopropyl | H | OCH₃ | OCH₃ | CH | |
| 6-Cl | SO₂—cyclopropyl | H | OCH₃ | OCH₃ | CH | |
| H | OSO₂CH₃ | H | OCH₃ | OCH₃ | CH | |
| H | OSO₂CH₃ | H | OCH₃ | CH₃ | CH | |
| H | OSO₂CH₃ | H | Cl | OCH₃ | CH | |
| H | OSO₂CH₃ | H | CH₃ | CH₃ | CH | |
| H | OSO₂CH₃ | H | OCH₃ | OCH₃ | N | |
| H | OSO₂CH₃ | H | OCH₃ | CH₃ | N | |
| H | OSO₂CH₃ | H | OCH₂CH₃ | NHCH₃ | N | |
| H | OSO₂CH₃ | CH₃ | OCH₃ | CH₃ | N | |
| 2-Cl | OSO₂CH₃ | H | OCH₃ | OCH₃ | CH | |
| 2-F | OSO₂CH₃ | H | OCH₃ | OCH₃ | CH | |
| 6-CH₃ | OSO₂CH₃ | H | OCH₃ | OCH₃ | CH | |
| 6-OCH₃ | OSO₂CH₃ | H | OCH₃ | OCH₃ | CH | |
| 6-F | OSO₂CH₃ | H | OCH₃ | OCH₃ | CH | |
| 6-Cl | OSO₂CH₃ | H | OCH₃ | OCH₃ | CH | |
| H | OSO₂CH₂CH₃ | H | OCH₃ | OCH₃ | CH | |
| H | OSO₂CH₂CH₃ | H | OCH₃ | CH₃ | CH | |
| H | OSO₂CH₂CH₃ | H | Cl | OCH₃ | CH | |
| H | OSO₂CH₂CH₃ | H | CH₃ | CH₃ | CH | |
| H | OSO₂CH₂CH₃ | H | OCH₃ | OCH₃ | N | |
| H | OSO₂CH₂CH₃ | H | OCH₃ | CH₃ | N | |
| H | OSO₂CH₂CH₃ | H | OCH₂CH₃ | NHCH₃ | N | |
| H | OSO₂CH₂CH₃ | CH₃ | OCH₃ | CH₃ | N | |
| 2-Cl | OSO₂CH₂CH₃ | H | OCH₃ | OCH₃ | CH | |
| 2-F | OSO₂CH₂CH₃ | H | OCH₃ | OCH₃ | CH | |
| 6-CH₃ | OSO₂CH₂CH₃ | H | OCH₃ | OCH₃ | CH | |
| 6-OCH₃ | OSO₂CH₂CH₃ | H | OCH₃ | OCH₃ | CH | |
| 6-F | OSO₂CH₂CH₃ | H | OCH₃ | OCH₃ | CH | |
| 6-Cl | OSO₂CH₂CH₃ | H | OCH₃ | OCH₃ | CH | |
| H | OSO₂CH₂CH₂CH₃ | H | OCH₃ | OCH₃ | CH | |
| H | OSO₂CH₂CH₂CH₃ | H | OCH₃ | CH₃ | CH | |
| H | OSO₂CH₂CH₂CH₃ | H | Cl | OCH₃ | CH | |
| H | OSO₂CH₂CH₂CH₃ | H | CH₃ | CH₃ | CH | |
| H | OSO₂CH₂CH₂CH₃ | H | OCH₃ | OCH₃ | N | |
| H | OSO₂CH₂CH₂CH₃ | H | OCH₃ | CH₃ | N | |
| H | OSO₂CH₂CH₂CH₃ | H | OCH₂CH₃ | NHCH₃ | N | |
| H | OSO₂CH₂CH₂CH₃ | CH₃ | OCH₃ | CH₃ | N | |
| 2-Cl | OSO₂CH₂CH₂CH₃ | H | OCH₃ | OCH₃ | CH | |
| 2-F | OSO₂CH₂CH₂CH₃ | H | OCH₃ | OCH₃ | CH | |
| 6-CH₃ | OSO₂CH₂CH₂CH₃ | H | OCH₃ | OCH₃ | CH | |
| 6-OCH₃ | OSO₂CH₂CH₂CH₃ | H | OCH₃ | OCH₃ | CH | |
| 6-F | OSO₂CH₂CH₂CH₃ | H | OCH₃ | OCH₃ | CH | |
| 6-Cl | OSO₂CH₂CH₂CH₃ | H | OCH₃ | OCH₃ | CH | |
| H | OSO₂CF₃ | H | OCH₃ | OCH₃ | CH | |
| H | OSO₂CF₃ | H | OCH₃ | CH₃ | CH | |
| H | OSO₂CF₃ | H | Cl | OCH₃ | CH | |
| H | OSO₂CF₃ | H | CH₃ | CH₃ | CH | |
| H | OSO₂CF₃ | H | OCH₃ | OCH₃ | N | |
| H | OSO₂CF₃ | H | OCH₃ | CH₃ | N | |
| H | OSO₂CF₃ | H | OCH₂CH₃ | NHCH₃ | N | |
| H | OSO₂CF₃ | CH₃ | OCH₃ | CH₃ | N | |
| 2-Cl | OSO₂CF₃ | H | OCH₃ | OCH₃ | CH | |
| 2-F | OSO₂CF₃ | H | OCH₃ | OCH₃ | CH | |
| 6-CH₃ | OSO₂CF₃ | H | OCH₃ | OCH₃ | CH | |
| 6-OCH₃ | OSO₂CF₃ | H | OCH₃ | OCH₃ | CH | |
| 6-F | OSO₂CF₃ | H | OCH₃ | OCH₃ | CH | |
| 6-Cl | OSO₂CF₃ | H | OCH₃ | OCH₃ | CH | |
| H | OSO₂CCl₃ | H | OCH₃ | OCH₃ | CH | |
| H | OSO₂CCl₃ | H | OCH₃ | CH₃ | CH | |
| H | OSO₂CCl₃ | H | Cl | OCH₃ | CH | |
| H | OSO₂CCl₃ | H | CH₃ | CH₃ | CH | |

TABLE III-continued

General Formula 3

| R₁ | R₄ | R | X | Y | Z | m.p. (°C.) |
|---|---|---|---|---|---|---|
| H | OSO₂CCl₃ | H | OCH₃ | OCH₃ | N | |
| H | OSO₂CCl₃ | H | OCH₃ | CH₃ | N | |
| H | OSO₂CCl₃ | H | OCH₂CH₃ | NHCH₃ | N | |
| H | OSO₂CCl₃ | CH₃ | OCH₃ | CH₃ | N | |
| 2-Cl | OSO₂CCl₃ | H | OCH₃ | OCH₃ | CH | |
| 2-F | OSO₂CCl₃ | H | OCH₃ | OCH₃ | CH | |
| 6-CH₃ | OSO₂CCl₃ | H | OCH₃ | OCH₃ | CH | |
| 6-OCH₃ | OSO₂CCl₃ | H | OCH₃ | OCH₃ | CH | |
| 6-F | OSO₂CCl₃ | H | OCH₃ | OCH₃ | CH | |
| 6-Cl | OSO₂CCl₃ | H | OCH₃ | OCH₃ | CH | |
| H | N₃ | H | OCH₃ | OCH₃ | CH | |
| H | N₃ | H | OCH₃ | CH₃ | CH | |
| H | N₃ | H | Cl | OCH₃ | CH | |
| H | N₃ | H | CH₃ | CH₃ | CH | |
| H | N₃ | H | OCH₃ | OCH₃ | N | |
| H | N₃ | H | OCH₃ | CH₃ | N | |
| H | N₃ | H | OCH₂CH₃ | NHCH₃ | N | |
| H | N₃ | CH₃ | OCH₃ | CH₃ | N | |
| 2-Cl | N₃ | H | OCH₃ | OCH₃ | CH | |
| 2-F | N₃ | H | OCH₃ | OCH₃ | CH | |
| 6-CH₃ | N₃ | H | OCH₃ | OCH₃ | CH | |
| 6-OCH₃ | N₃ | H | OCH₃ | OCH₃ | CH | |
| 6-F | N₃ | H | OCH₃ | OCH₃ | CH | |
| 6-Cl | N₃ | H | OCH₃ | OCH₃ | CH | |
| H | P(O)(OCH₃)₂ | H | OCH₃ | OCH₃ | CH | |
| H | P(O)(OCH₃)₂ | H | OCH₃ | CH₃ | CH | |
| H | P(O)(OCH₃)₂ | H | Cl | OCH₃ | CH | |
| H | P(O)(OCH₃)₂ | H | CH₃ | CH₃ | CH | |
| H | P(O)(OCH₃)₂ | H | OCH₃ | OCH₃ | N | |
| H | P(O)(OCH₃)₂ | H | OCH₃ | CH₃ | N | |
| H | P(O)(OCH₃)₂ | H | OCH₂CH₃ | NHCH₃ | N | |
| H | P(O)(OCH₃)₂ | CH₃ | OCH₃ | CH₃ | N | |
| 2-Cl | P(O)(OCH₃)₂ | H | OCH₃ | OCH₃ | CH | |
| 2-F | P(O)(OCH₃)₂ | H | OCH₃ | OCH₃ | CH | |
| 6-CH₃ | P(O)(OCH₃)₂ | H | OCH₃ | OCH₃ | CH | |
| 6-OCH₃ | P(O)(OCH₃)₂ | H | OCH₃ | OCH₃ | CH | |
| 6-F | P(O)(OCH₃)₂ | H | OCH₃ | OCH₃ | CH | |
| 6-Cl | P(O)(OCH₃)₂ | H | OCH₃ | OCH₃ | CH | |
| H | CN | H | OCH₃ | OCH₃ | CH | |
| H | CN | H | OCH₃ | CH₃ | CH | |
| H | CN | H | Cl | OCH₃ | CH | |
| H | CN | H | CH₃ | CH₃ | CH | |
| H | CN | H | OCH₃ | OCH₃ | CN | |
| H | CN | H | OCH₃ | CH₃ | CN | |
| H | CN | H | OCH₂CH₃ | CNHCH₃ | CN | |
| H | CN | CH₃ | OCH₃ | CH₃ | CN | |
| 2-Cl | CN | H | OCH₃ | OCH₃ | CH | |
| 2-F | CN | H | OCH₃ | OCH₃ | CH | |
| 6-CH₃ | CN | H | OCH₃ | OCH₃ | CH | |
| 6-OCH₃ | CN | H | OCH₃ | OCH₃ | CH | |
| 6-F | CN | H | OCH₃ | OCH₃ | CH | |
| 6-Cl | CN | H | OCH₃ | OCH₃ | CH | |
| H | CH₂F | H | OCH₃ | OCH₃ | CH | |
| H | CH₂F | H | OCH₃ | CH₃ | CH | |
| H | CH₂F | H | Cl | OCH₃ | CH | |
| H | CH₂F | H | CH₃ | CH₃ | CH | |
| H | CH₂F | H | OCH₃ | OCH₃ | N | |
| H | CH₂F | H | OCH₃ | CH₃ | N | |
| H | CH₂F | H | OCH₂CH₃ | NHCH₃ | N | |
| H | CH₂F | CH₃ | OCH₃ | CH₃ | N | |
| 2-Cl | CH₂F | H | OCH₃ | OCH₃ | CH | |
| 2-F | CH₂F | H | OCH₃ | OCH₃ | CH | |
| 6-CH₃ | CH₂F | H | OCH₃ | OCH₃ | CH | |
| 6-OCH₃ | CH₂F | H | OCH₃ | OCH₃ | CH | |
| 6-F | CH₂F | H | OCH₃ | OCH₃ | CH | |
| 6-Cl | CH₂F | H | OCH₃ | OCH₃ | CH | |
| H | CF₂H | H | OCH₃ | OCH₃ | CH | |
| H | CF₂H | H | OCH₃ | CH₃ | CH | |
| H | CF₂H | H | Cl | OCH₃ | CH | |
| H | CF₂H | H | CH₃ | CH₃ | CH | |
| H | CF₂H | H | OCH₃ | OCH₃ | N | |
| H | CF₂H | H | OCH₃ | CH₃ | N | |
| H | CF₂H | H | OCH₃ | OCH₃ | N | |
| H | CF₂H | CH₃ | OCH₃ | CH₃ | N | |
| 2-Cl | CF₂H | H | OCH₃ | OCH₃ | CH | |
| 2-F | CF₂H | H | OCH₃ | OCH₃ | CH | |
| 6-CH₃ | CF₂H | H | OCH₃ | OCH₃ | CH | |
| 6-OCH₃ | CF₂H | H | OCH₃ | OCH₃ | CH | |
| 6-F | CF₂H | H | OCH₃ | OCH₃ | CH | |

TABLE III-continued

General Formula 3

| R₁ | R₄ | R | X | Y | Z | m.p. (°C.) |
|---|---|---|---|---|---|---|
| 6-Cl | CF₂H | H | OCH₃ | OCH₃ | CH | |

TABLE IV

General Formula 4

| R₁ | R₅ | R | X | Y | Z | m.p. (°C.) |
|---|---|---|---|---|---|---|
| H | SOCH₃ | H | OCH₃ | OCH₃ | CH | |
| H | SOCH₃ | H | OCH₃ | CH₃ | CH | |
| H | SOCH₃ | H | Cl | OCH₃ | CH | |
| H | SOCH₃ | H | CH₃ | CH₃ | CH | |
| H | SOCH₃ | H | OCH₃ | OCH₃ | N | |
| H | SOCH₃ | H | OCH₃ | CH₃ | N | |
| H | SOCH₃ | H | OCH₂CH₃ | NHCH₃ | N | |
| H | SOCH₃ | CH₃ | OCH₃ | CH₃ | N | |
| 5-CH₃ | SOCH₃ | H | OCH₃ | OCH₃ | CH | |
| 5-OCH₃ | SOCH₃ | H | OCH₃ | OCH₃ | CH | |
| 6-CH₃ | SOCH₃ | H | OCH₃ | OCH₃ | CH | |
| 6-OCH₃ | SOCH₃ | H | OCH₃ | OCH₃ | CH | |
| 6-F | SOCH₃ | H | OCH₃ | OCH₃ | CH | |
| 6-Cl | SOCH₃ | H | OCH₃ | OCH₃ | CH | |
| H | SO₂CH₃ | H | OCH₃ | OCH₃ | CH | |
| H | SO₂CH₃ | H | OCH₃ | CH₃ | CH | |
| H | SO₂CH₃ | H | Cl | OCH₃ | CH | |
| H | SO₂CH₃ | H | CH₃ | CH₃ | CH | |
| H | SO₂CH₃ | H | OCH₃ | OCH₃ | N | |
| H | SO₂CH₃ | H | OCH₃ | CH₃ | N | |
| H | SO₂CH₃ | H | OCH₂CH₃ | NHCH₃ | N | |
| H | SO₂CH₃ | CH₃ | OCH₃ | CH₃ | N | |
| 5-CH₃ | SO₂CH₃ | H | OCH₃ | OCH₃ | CH | |
| 5-OCH₃ | SO₂CH₃ | H | OCH₃ | OCH₃ | CH | |
| 6-CH₃ | SO₂CH₃ | H | OCH₃ | OCH₃ | CH | |
| 6-OCH₃ | SO₂CH₃ | H | OCH₃ | OCH₃ | CH | |
| 6-F | SO₂CH₃ | H | OCH₃ | OCH₃ | CH | |
| 6-Cl | SO₂CH₃ | H | OCH₃ | OCH₃ | CH | |
| H | SOCH₂CH₃ | H | OCH₃ | OCH₃ | CH | |
| H | SOCH₂CH₃ | H | OCH₃ | CH₃ | CH | |
| H | SOCH₂CH₃ | H | Cl | OCH₃ | CH | |
| H | SOCH₂CH₃ | H | CH₃ | CH₃ | CH | |
| H | SOCH₂CH₃ | H | OCH₃ | OCH₃ | N | |
| H | SOCH₂CH₃ | H | OCH₃ | CH₃ | N | |
| H | SOCH₂CH₃ | H | OCH₂CH₃ | NHCH₃ | N | |
| H | SOCH₂CH₃ | CH₃ | OCH₃ | CH₃ | N | |
| 5-CH₃ | SOCH₂CH₃ | H | OCH₃ | OCH₃ | CH | |
| 5-OCH₃ | SOCH₂CH₃ | H | OCH₃ | OCH₃ | CH | |
| 6-CH₃ | SOCH₂CH₃ | H | OCH₃ | OCH₃ | CH | |
| 6-OCH₃ | SOCH₂CH₃ | H | OCH₃ | OCH₃ | CH | |
| 6-F | SOCH₂CH₃ | H | OCH₃ | OCH₃ | CH | |
| 6-Cl | SOCH₂CH₃ | H | OCH₃ | OCH₃ | CH | |
| H | SO₂CH₂CH₃ | H | OCH₃ | OCH₃ | CH | |
| H | SO₂CH₂CH₃ | H | OCH₃ | CH₃ | CH | |
| H | SO₂CH₂CH₃ | H | Cl | OCH₃ | CH | |
| H | SO₂CH₂CH₃ | H | CH₃ | CH₃ | CH | |
| H | SO₂CH₂CH₃ | H | OCH₃ | OCH₃ | N | |
| H | SO₂CH₂CH₃ | H | OCH₃ | CH₃ | N | |
| H | SO₂CH₂CH₃ | H | OCH₂CH₃ | NHCH₃ | N | |
| H | SO₂CH₂CH₃ | CH₃ | OCH₃ | CH₃ | N | |
| 5-CH₃ | SO₂CH₂CH₃ | H | OCH₃ | OCH₃ | CH | |
| 5-OCH₃ | SO₂CH₂CH₃ | H | OCH₃ | OCH₃ | CH | |
| 6-CH₃ | SO₂CH₂CH₃ | H | OCH₃ | OCH₃ | CH | |
| 6-OCH₃ | SO₂CH₂CH₃ | H | OCH₃ | OCH₃ | CH | |
| 6-F | SO₂CH₂CH₃ | H | OCH₃ | OCH₃ | CH | |
| 6-Cl | SO₂CH₂CH₃ | H | OCH₃ | OCH₃ | CH | |
| H | SOCH₂CH₂CH₃ | H | OCH₃ | OCH₃ | CH | |
| H | SOCH₂CH₂CH₃ | H | OCH₃ | CH₃ | CH | |
| H | SOCH₂CH₂CH₃ | H | Cl | OCH₃ | CH | |
| H | SOCH₂CH₂CH₃ | H | CH₃ | CH₃ | CH | |
| H | SOCH₂CH₂CH₃ | H | OCH₃ | OCH₃ | N | |
| H | SOCH₂CH₂CH₃ | H | OCH₃ | CH₃ | N | |
| H | SOCH₂CH₂CH₃ | H | OCH₂CH₃ | NHCH₃ | N | |
| H | SOCH₂CH₂CH₃ | CH₃ | OCH₃ | CH₃ | N | |
| 5-CH₃ | SOCH₂CH₂CH₃ | H | OCH₃ | OCH₃ | CH | |
| 5-OCH₃ | SOCH₂CH₂CH₃ | H | OCH₃ | OCH₃ | CH | |
| 6-CH₃ | SOCH₂CH₂CH₃ | H | OCH₃ | OCH₃ | CH | |
| 6-OCH₃ | SOCH₂CH₂CH₃ | H | OCH₃ | OCH₃ | CH | |
| 6-F | SOCH₂CH₂CH₃ | H | OCH₃ | OCH₃ | CH | |
| 6-Cl | SOCH₂CH₂CH₃ | H | OCH₃ | OCH₃ | CH | |
| H | SO₂CH₂CH₂CH₃ | H | OCH₃ | OCH₃ | CH | |
| H | SO₂CH₂CH₂CH₃ | H | OCH₃ | CH₃ | CH | |

TABLE IV-continued

General Formula 4

| R₁ | R₅ | R | X | Y | Z | m.p. (°C.) |
|---|---|---|---|---|---|---|
| H | SO₂CH₂CH₂CH₃ | H | Cl | OCH₃ | CH | |
| H | SO₂CH₂CH₂CH₃ | H | CH₃ | CH₃ | CH | |
| H | SO₂CH₂CH₂CH₃ | H | OCH₃ | OCH₃ | N | |
| H | SO₂CH₂CH₂CH₃ | H | OCH₃ | CH₃ | N | |
| H | SO₂CH₂CH₂CH₃ | H | OCH₂CH₃ | NHCH₃ | N | |
| H | SO₂CH₂CH₂CH₃ | CH₃ | OCH₃ | CH₃ | N | |
| 5-CH₃ | SO₂CH₂Ch₂CH₃ | H | OCH₃ | OCH₃ | CH | |
| 5-OCH₃ | SO₂CH₂CH₂CH₃ | H | OCH₃ | OCH₃ | CH | |
| 6-CH₃ | SO₂CH₂CH₂CH₃ | H | OCH₃ | OCH₃ | CH | |
| 6-OCH₃ | SO₂CH₂CH₂CH₃ | H | OCH₃ | OCH₃ | CH | |
| 6-F | SO₂CH₂CH₂CH₃ | H | OCH₃ | OCH₃ | CH | |
| 6-Cl | SO₂CH₂CH₂CH₃ | H | OCH₃ | OCH₃ | CH | |
| H | SOCH₂CH₂CH₂CH₃ | H | OCH₃ | OCH₃ | CH | |
| H | SOCH₂CH₂CH₂CH₃ | H | OCH₃ | CH₃ | CH | |
| H | SOCH₂CH₂CH₂CH₃ | H | Cl | OCH₃ | CH | |
| H | SOCH₂CH₂CH₂CH₃ | H | CH₃ | CH₃ | CH | |
| H | SOCH₂CH₂CH₂CH₃ | H | OCH₃ | OCH₃ | N | |
| H | SOCH₂CH₂CH₂CH₃ | H | OCH₃ | CH₃ | N | |
| H | SOCH₂CH₂CH₂CH₃ | H | OCH₂CH₃ | NHCH₃ | N | |
| H | SOCH₂CH₂CH₂CH₃ | CH₃ | OCH₃ | CH₃ | N | |
| 5-CH₃ | SOCH₂CH₂CH₂CH₃ | H | OCH₃ | OCH₃ | CH | |
| 5-OCH₃ | SOCH₂CH₂CH₂CH₃ | H | OCH₃ | OCH₃ | CH | |
| 6-CH₃ | SOCH₂CH₂CH₂CH₃ | H | OCH₃ | OCH₃ | CH | |
| 6-OCH₃ | SOCH₂CH₂CH₂CH₃ | H | OCH₃ | OCH₃ | CH | |
| 6-F | SOCH₂CH₂CH₂CH₃ | H | OCH₃ | OCH₃ | CH | |
| 6-Cl | SOCH₂CH₂CH₂CH₃ | H | OCH₃ | OCH₃ | CH | |
| H | SO₂CH₂CH₂CH₂CH₃ | H | OCH₃ | OCH₃ | CH | |
| H | SO₂CH₂CH₂CH₂CH₃ | H | OCH₃ | CH₃ | CH | |
| H | SO₂CH₂CH₂CH₂CH₃ | H | Cl | OCH₃ | CH | |
| H | SO₂CH₂CH₂CH₂CH₃ | H | CH₃ | CH₃ | CH | |
| H | SO₂CH₂CH₂CH₂CH₃ | H | OCH₃ | OCH₃ | N | |
| H | SO₂CH₂CH₂CH₂CH₃ | H | OCH₃ | CH₃ | N | |
| H | SO₂CH₂CH₂CH₂CH₃ | H | OCH₂CH₃ | NHCH₃ | N | |
| H | SO₂CH₂CH₂CH₂CH₃ | CH₃ | OCH₃ | CH₃ | N | |
| 5-CH₃ | SO₂CH₂CH₂CH₂CH₃ | H | OCH₃ | OCH₃ | CH | |
| 5-OCH₃ | SO₂CH₂CH₂CH₂CH₃ | H | OCH₃ | OCH₃ | CH | |
| 6-CH₃ | SO₂CH₂CH₂CH₂CH₃ | H | OCH₃ | OCH₃ | CH | |
| 6-OCH₃ | SO₂CH₂CH₂CH₂CH₃ | H | OCH₃ | OCH₃ | CH | |
| 6-F | SO₂CH₂CH₂CH₂CH₃ | H | OCH₃ | OCH₃ | CH | |
| 6-Cl | SO₂CH₂CH₂CH₂CH₃ | H | OCH₃ | OCH₃ | CH | |
| H | SOCH(CH₃)₂ | H | OCH₃ | OCH₃ | CH | |
| H | SOCH(CH₃)₂ | H | OCH₃ | CH₃ | CH | |
| H | SOCH(CH₃)₂ | H | Cl | OCH₃ | CH | |
| H | SOCH(CH₃)₂ | H | CH₃ | CH₃ | CH | |
| H | SOCH(CH₃)₂ | H | OCH₃ | OCH₃ | N | |
| H | SOCH(CH₃)₂ | H | OCH₃ | CH₃ | N | |
| H | SOCH(CH₃)₂ | H | OCH₂CH₃ | NHCH₃ | N | |
| H | SOCH(CH₃)₂ | CH₃ | OCH₃ | CH₃ | N | |
| 5-CH₃ | SOCH(CH₃)₂ | H | OCH₃ | OCH₃ | CH | |
| 5-OCH₃ | SOCH(CH₃)₂ | H | OCH₃ | OCH₃ | CH | |
| 6-CH₃ | SOCH(CH₃)₂ | H | OCH₃ | OCH₃ | CH | |
| 6-OCH₃ | SOCH(CH₃)₂ | H | OCH₃ | OCH₃ | CH | |
| 6-F | SOCH(CH₃)₂ | H | OCH₃ | OCH₃ | CH | |
| 6-Cl | SOCH(CH₃)₂ | H | OCH₃ | OCH₃ | CH | |
| H | SO₂CH(CH₃)₂ | H | OCH₃ | OCH₃ | CH | |
| H | SO₂CH(CH₃)₂ | H | OCH₃ | CH₃ | CH | |
| H | SO₂CH(CH₃)₂ | H | Cl | OCH₃ | CH | |
| H | SO₂CH(CH₃)₂ | H | CH₃ | CH₃ | CH | |
| H | SO₂CH(CH₃)₂ | H | OCH₃ | OCH₃ | N | |
| H | SO₂CH(CH₃)₂ | H | OCH₃ | CH₃ | N | |
| H | SO₂CH(CH₃)₂ | H | OCH₂CH₃ | NHCH₃ | N | |
| H | SO₂CH(CH₃)₂ | CH₃ | OCH₃ | CH₃ | N | |
| 5-CH₃ | SO₂CH(CH₃)₂ | H | OCH₃ | OCH₃ | CH | |
| 5-OCH₃ | SO₂CH(CH₃)₂ | H | OCH₃ | OCH₃ | CH | |
| 6-CH₃ | SO₂CH(CH₃)₂ | H | OCH₃ | OCH₃ | CH | |
| 6-OCH₃ | SO₂CH(CH₃)₂ | H | OCH₃ | OCH₃ | CH | |
| 6-F | SO₂CH(CH₃)₂ | H | OCH₃ | OCH₃ | CH | |
| 6-Cl | SO₂CH(CH₃)₂ | H | OCH₃ | OCH₃ | CH | |
| H | S—cyclopropyl | H | OCH₃ | OCH₃ | CH | |
| H | S—cyclopropyl | H | OCH₃ | CH₃ | CH | |
| H | S—cyclopropyl | H | Cl | OCH₃ | CH | |
| H | S—cyclopropyl | H | CH₃ | CH₃ | CH | |
| H | S—cyclopropyl | H | OCH₃ | OCH₃ | N | |
| H | S—cyclopropyl | H | OCH₃ | CH₃ | N | |
| H | S—cyclopropyl | H | OCH₂CH₃ | NHCH₃ | N | |
| H | S—cyclopropyl | CH₃ | OCH₃ | CH₃ | N | |
| 5-CH₃ | S—cyclopropyl | H | OCH₃ | OCH₃ | CH | |
| 5-OCH₃ | S—cyclopropyl | H | OCH₃ | OCH₃ | CH | |
| 6-CH₃ | S—cyclopropyl | H | OCH₃ | OCH₃ | CH | |
| 6-OCH₃ | S—cyclopropyl | H | OCH₃ | OCH₃ | CH | |

TABLE IV-continued

General Formula 4

| R₁ | R₅ | R | X | Y | Z | m.p. (°C.) |
|---|---|---|---|---|---|---|
| 6-F | S—cyclopropyl | H | OCH₃ | OCH₃ | CH | |
| 6-Cl | S—cyclopropyl | H | OCH₃ | OCH₃ | CH | |
| H | SO—cyclopropyl | H | OCH₃ | OCH₃ | CH | |
| H | SO—cyclopropyl | H | OCH₃ | CH₃ | CH | |
| H | SO—cyclopropyl | H | Cl | OCH₃ | CH | |
| H | SO—cyclopropyl | H | CH₃ | CH₃ | CH | |
| H | SO—cyclopropyl | H | OCH₃ | OCH₃ | N | |
| H | SO—cyclopropyl | H | OCH₃ | CH₃ | N | |
| H | SO—cyclopropyl | H | OCH₂CH₃ | NHCH₃ | N | |
| H | SO—cyclopropyl | CH₃ | OCH₃ | CH₃ | N | |
| 5-CH₃ | SO—cyclopropyl | H | OCH₃ | OCH₃ | CH | |
| 5-OCH₃ | SO—cyclopropyl | H | OCH₃ | OCH₃ | CH | |
| 6-CH₃ | SO—cyclopropyl | H | OCH₃ | OCH₃ | CH | |
| 6-OCH₃ | SO—cyclopropyl | H | OCH₃ | OCH₃ | CH | |
| 6-F | SO—cyclopropyl | H | OCH₃ | OCH₃ | CH | |
| 6-Cl | SO—cyclopropyl | H | OCH₃ | OCH₃ | CH | |
| H | SO₂—cyclopropyl | H | OCH₃ | OCH₃ | CH | |
| H | SO₂—cyclopropyl | H | OCH₃ | CH₃ | CH | |
| H | SO₂—cyclopropyl | H | Cl | OCH₃ | CH | |
| H | SO₂—cyclopropyl | H | CH₃ | CH₃ | CH | |
| H | SO₂—cyclopropyl | H | OCH₃ | OCH₃ | N | |
| H | SO₂—cyclopropyl | H | OCH₃ | CH₃ | N | |
| H | SO₂—cyclopropyl | H | OCH₂CH₃ | NHCH₃ | N | |
| H | SO₂—cyclopropyl | CH₃ | OCH₃ | CH₃ | N | |
| 5-CH₃ | SO₂—cyclopropyl | H | OCH₃ | OCH₃ | CH | |
| 5-OCH₃ | SO₂—cyclopropyl | H | OCH₃ | OCH₃ | CH | |
| 6-CH₃ | SO₂—cyclopropyl | H | OCH₃ | OCH₃ | CH | |
| 6-OCH₃ | SO₂—cyclopropyl | H | OCH₃ | OCH₃ | CH | |
| 6-F | SO₂—cyclopropyl | H | OCH₃ | OCH₃ | CH | |
| 6-Cl | SO₂—cyclopropyl | H | OCH₃ | OCH₃ | CH | |
| H | OSO₂CH₃ | H | OCH₃ | OCH₃ | CH | |
| H | OSO₂CH₃ | H | OCH₃ | CH₃ | CH | |
| H | OSO₂CH₃ | H | Cl | OCH₃ | CH | |
| H | OSO₂CH₃ | H | CH₃ | CH₃ | CH | |
| H | OSO₂CH₃ | H | OCH₃ | OCH₃ | N | |
| H | OSO₂CH₃ | H | OCH₃ | CH₃ | N | |
| H | OSO₂CH₃ | H | OCH₂CH₃ | NHCH₃ | N | |
| H | OSO₂CH₃ | CH₃ | OCH₃ | CH₃ | N | |
| 5-CH₃ | OSO₂CH₃ | H | OCH₃ | OCH₃ | CH | |
| 5-OCH₃ | OSO₂CH₃ | H | OCH₃ | OCH₃ | CH | |
| 6-CH₃ | OSO₂CH₃ | H | OCH₃ | OCH₃ | CH | |
| 6-OCH₃ | OSO₂CH₃ | H | OCH₃ | OCH₃ | CH | |
| 6-F | OSO₂CH₃ | H | OCH₃ | OCH₃ | CH | |
| 6-Cl | OSO₂CH₃ | H | OCH₃ | OCH₃ | CH | |
| H | OSO₂CF₃ | H | OCH₃ | OCH₃ | CH | |
| H | OSO₂CF₃ | H | OCH₃ | CH₃ | CH | |
| H | OSO₂CF₃ | H | Cl | OCH₃ | CH | |
| H | OSO₂CF₃ | H | CH₃ | CH₃ | CH | |
| H | OSO₂CF₃ | H | OCH₃ | OCH₃ | N | |
| H | OSO₂CF₃ | H | OCH₃ | CH₃ | N | |
| H | OSO₂CF₃ | H | OCH₂CH₃ | NHCH₃ | N | |
| H | OSO₂CF₃ | CH₃ | OCH₃ | CH₃ | N | |
| 5-CH₃ | OSO₂CF₃ | H | OCH₃ | OCH₃ | CH | |
| 5-OCH₃ | OSO₂CF₃ | H | OCH₃ | OCH₃ | CH | |
| 6-CH₃ | OSO₂CF₃ | H | OCH₃ | OCH₃ | CH | |
| 6-OCH₃ | OSO₂CF₃ | H | OCH₃ | OCH₃ | CH | |
| 6-F | OSO₂CF₃ | H | OCH₃ | OCH₃ | CH | |
| 6-Cl | OSO₂CF₃ | H | OCH₃ | OCH₃ | CH | |
| H | OSO₂CH₂CH₃ | H | OCH₃ | OCH₃ | CH | |
| H | OSO₂CH₂CH₃ | H | OCH₃ | CH₃ | CH | |
| H | OSO₂CH₂CH₃ | H | Cl | OCH₃ | CH | |
| H | OSO₂CH₂CH₃ | H | CH₃ | CH₃ | CH | |
| H | OSO₂CH₂CH₃ | H | OCH₃ | OCH₃ | N | |
| H | OSO₂CH₂CH₃ | H | OCH₃ | CH₃ | N | |
| H | OSO₂CH₂CH₃ | H | OCH₂CH₃ | NHCH₃ | N | |
| H | OSO₂CH₂CH₃ | CH₃ | OCH₃ | CH₃ | N | |
| 5-CH₃ | OSO₂CH₂CH₃ | H | OCH₃ | OCH₃ | CH | |
| 5-OCH₃ | OSO₂CH₂CH₃ | H | OCH₃ | OCH₃ | CH | |
| 6-CH₃ | OSO₂CH₂CH₃ | H | OCH₃ | OCH₃ | CH | |
| 6-OCH₃ | OSO₂CH₂CH₃ | H | OCH₃ | OCH₃ | CH | |
| 6-F | OSO₂CH₂CH₃ | H | OCH₃ | OCH₃ | CH | |
| 6-Cl | OSO₂CH₂CH₃ | H | OCH₃ | OCH₃ | CH | |
| H | N₃ | H | OCH₃ | OCH₃ | CH | |
| H | N₃ | H | OCH₃ | CH₃ | CH | |
| H | N₃ | H | Cl | OCH₃ | CH | |
| H | N₃ | H | CH₃ | CH₃ | CH | |
| H | N₃ | H | OCH₃ | OCH₃ | N | |
| H | N₃ | H | OCH₃ | CH₃ | N | |
| H | N₃ | H | OCH₂CH₃ | NHCH₃ | N | |
| H | N₃ | CH₃ | OCH₃ | CH₃ | N | |

TABLE IV-continued

General Formula 4

| R₁ | R₅ | R | X | Y | Z | m.p. (°C.) |
|---|---|---|---|---|---|---|
| 5-CH₃ | N₃ | H | OCH₃ | OCH₃ | CH | |
| 5-OCH₃ | N₃ | H | OCH₃ | OCH₃ | CH | |
| 6-CH₃ | N₃ | H | OCH₃ | OCH₃ | CH | |
| 6-OCH₃ | N₃ | H | OCH₃ | OCH₃ | CH | |
| 6-F | N₃ | H | OCH₃ | OCH₃ | CH | |
| 6-Cl | N₃ | H | OCH₃ | OCH₃ | CH | |
| H | CN | H | OCH₃ | OCH₃ | CH | |
| H | CN | H | OCH₃ | CH₃ | CH | |
| H | CN | H | Cl | OCH₃ | CH | |
| H | CN | H | CH₃ | CH₃ | CH | |
| H | CN | H | OCH₃ | OCH₃ | N | |
| H | CN | H | OCH₃ | CH₃ | N | |
| H | CN | H | OCH₂CH₃ | NHCH₃ | N | |
| H | CN | CH₃ | OCH₃ | CH₃ | N | |
| 5-CH₃ | CN | H | OCH₃ | OCH₃ | CH | |
| 5-OCH₃ | CN | H | OCH₃ | OCH₃ | CH | |
| 6-CH₃ | CN | H | OCH₃ | OCH₃ | CH | |
| 6-OCH₃ | CN | H | OCH₃ | OCH₃ | CH | |
| 6-F | CN | H | OCH₃ | OCH₃ | CH | |
| 6-Cl | CN | H | OCH₃ | OCH₃ | CH | |
| H | CH₂F | H | OCH₃ | OCH₃ | CH | |
| H | CH₂F | H | OCH₃ | CH₃ | CH | |
| H | CH₂F | H | Cl | OCH₃ | CH | |
| H | CH₂F | H | CH₃ | CH₃ | CH | |
| H | CH₂F | H | OCH₃ | OCH₃ | N | |
| H | CH₂F | H | OCH₃ | CH₃ | N | |
| H | CH₂F | H | OCH₂CH₃ | NHCH₃ | N | |
| H | CH₂F | CH₃ | OCH₃ | CH₃ | N | |
| 5-CH₃ | CH₂F | H | OCH₃ | OCH₃ | CH | |
| 5-OCH₃ | CH₂F | H | OCH₃ | OCH₃ | CH | |
| 6-CH₃ | CH₂F | H | OCH₃ | OCH₃ | CH | |
| 6-OCH₃ | CH₂F | H | OCH₃ | OCH₃ | CH | |
| 6-F | CH₂F | H | OCH₃ | OCH₃ | CH | |
| 6-Cl | CH₂F | H | OCH₃ | OCH₃ | CH | |
| H | CF₂H | H | OCH₃ | OCH₃ | CH | |
| H | CF₂H | H | OCH₃ | CH₃ | CH | |
| H | CF₂H | H | Cl | OCH₃ | CH | |
| H | CF₂H | H | CH₃ | CH₃ | CH | |
| H | CF₂H | H | OCH₃ | OCH₃ | N | |
| H | CF₂H | H | OCH₃ | CH₃ | N | |
| H | CF₂H | H | OCH₂CH₃ | NHCH₃ | N | |
| H | CF₂H | CH₃ | OCH₃ | CH₃ | N | |
| 5-CH₃ | CF₂H | H | OCH₃ | OCH₃ | CH | |
| 5-OCH₃ | CF₂H | H | OCH₃ | OCH₃ | CH | |
| 6-CH₃ | CF₂H | H | OCH₃ | OCH₃ | CH | |
| 6-OCH₃ | CF₂H | H | OCH₃ | OCH₃ | CH | |
| 6-F | CF₂H | H | OCH₃ | OCH₃ | CH | |
| 6-Cl | CF₂H | H | OCH₃ | OCH₃ | CH | |

TABLE V

General Formula 5

| R₁ | R₆ | R | X | Y | Z | m.p. (°C.) |
|---|---|---|---|---|---|---|
| H | SCH₃ | H | OCH₃ | OCH₃ | CH | |
| H | SCH₃ | H | OCH₃ | OCH₃ | CH | |
| H | SCH₃ | H | OCH₃ | CH₃ | CH | |
| H | SCH₃ | H | Cl | OCH₃ | CH | |
| H | SCH₃ | H | CH₃ | CH₃ | CH | |
| H | SCH₃ | H | OCH₃ | OCH₃ | N | |
| H | SCH₃ | H | OCH₃ | OCH₃ | N | |
| H | SCH₃ | H | OCH₃ | CH₃ | N | |
| H | SCH₃ | H | OCH₂CH₃ | NHCH₃ | N | |
| H | SCH₃ | CH₃ | OCH₃ | CH₃ | N | |
| 4-CH₃ | SCH₃ | H | OCH₃ | OCH₃ | CH | |
| 4-OCH₃ | SCH₃ | H | OCH₃ | OCH₃ | CH | |
| 6-CH₃ | SCH₃ | H | OCH₃ | OCH₃ | CH | |
| 6-OCH₃ | SCH₃ | H | OCH₃ | OCH₃ | CH | |
| 6-F | SCH₃ | H | OCH₃ | OCH₃ | CH | |
| 6-Cl | SCH₃ | H | OCH₃ | OCH₃ | CH | |
| H | SOCH₃ | H | OCH₃ | OCH₃ | CH | |
| H | SOCH₃ | H | OCH₃ | CH₃ | CH | |
| H | SOCH₃ | H | Cl | OCH₃ | CH | |
| H | SOCH₃ | H | CH₃ | CH₃ | CH | |
| H | SOCH₃ | H | OCH₃ | OCH₃ | N | |
| H | SOCH₃ | H | OCH₃ | CH₃ | N | |
| H | SOCH₃ | H | OCH₂CH₃ | NHCH₃ | N | |
| H | SOCH₃ | CH₃ | OCH₃ | CH₃ | N | |
| 4-CH₃ | SOCH₃ | H | OCH₃ | OCH₃ | CH | |

TABLE V-continued

General Formula 5

| R₁ | R₆ | R | X | Y | Z | m.p. (°C.) |
|---|---|---|---|---|---|---|
| 4-OCH₃ | SOCH₃ | H | OCH₃ | OCH₃ | CH | |
| 6-CH₃ | SOCH₃ | H | OCH₃ | OCH₃ | CH | |
| 6-OCH₃ | SOCH₃ | H | OCH₃ | OCH₃ | CH | |
| 6-F | SOCH₃ | H | OCH₃ | OCH₃ | CH | |
| 6-Cl | SOCH₃ | H | OCH₃ | OCH₃ | CH | |
| H | SO—cyclopropyl | H | OCH₃ | OCH₃ | CH | |
| H | SO—cyclopropyl | H | OCH₃ | CH₃ | CH | |
| H | SO—cyclopropyl | H | Cl | OCH₃ | CH | |
| H | SO—cyclopropyl | H | CH₃ | CH₃ | CH | |
| H | SO—cyclopropyl | H | OCH₃ | OCH₃ | N | |
| H | SO—cyclopropyl | H | OCH₃ | CH₃ | N | |
| H | SO—cyclopropyl | H | OCH₂CH₃ | NHCH₃ | N | |
| H | SO—cyclopropyl | CH₃ | OCH₃ | CH₃ | N | |
| 4-CH₃ | SO—cyclopropyl | H | OCH₃ | OCH₃ | CH | |
| 4-OCH₃ | SO—cyclopropyl | H | OCH₃ | OCH₃ | CH | |
| 6-CH₃ | SO—cyclopropyl | H | OCH₃ | OCH₃ | CH | |
| 6-OCH₃ | SO—cyclopropyl | H | OCH₃ | OCH₃ | CH | |
| 6-F | SO—cyclopropyl | H | OCH₃ | OCH₃ | CH | |
| 6-Cl | SO—cyclopropyl | H | OCH₃ | OCH₃ | CH | |
| H | SO₂—cyclopropyl | H | OCH₃ | OCH₃ | CH | |
| H | SO₂—cyclopropyl | H | OCH₃ | CH₃ | CH | |
| H | SO₂—cyclopropyl | H | Cl | OCH₃ | CH | |
| H | SO₂—cyclopropyl | H | CH₃ | CH₃ | CH | |
| H | SO₂—cyclopropyl | H | OCH₃ | OCH₃ | N | |
| H | SO₂—cyclopropyl | H | OCH₃ | CH₃ | N | |
| H | SO₂—cyclopropyl | H | OCH₂CH₂ | NHCH₃ | N | |
| H | SO₂—cyclopropyl | CH₃ | OCH₃ | CH₃ | N | |
| 4-CH₃ | SO₂—cyclopropyl | H | OCH₃ | OCH₃ | CH | |
| 4-OCH₃ | SO₂—cyclopropyl | H | OCH₃ | OCH₃ | CH | |
| 6-CH₃ | SO₂—cyclopropyl | H | OCH₃ | OCH₃ | CH | |
| 6-OCH₃ | SO₂—cyclopropyl | H | OCH₃ | OCH₃ | CH | |
| 6-F | SO₂—cyclopropyl | H | OCH₃ | OCH₃ | CH | |
| 6-Cl | SO₂—cyclopropyl | H | OCH₃ | OCH₃ | CH | |
| H | OSO₂CH₃ | H | OCH₃ | OCH₃ | CH | |
| H | OSO₂CH₃ | H | OCH₃ | CH₃ | CH | |
| H | OSO₂CH₃ | H | Cl | OCH₃ | CH | |
| H | OSO₂CH₃ | H | CH₃ | CH₃ | CH | |
| H | OSO₂CH₃ | H | OCH₃ | OCH₃ | N | |
| H | OSO₂CH₃ | H | OCH₃ | CH₃ | N | |
| H | OSO₂CH₃ | H | OCH₂CH₃ | NHCH₃ | N | |
| H | OSO₂CH₃ | CH₃ | OCH₃ | CH₃ | N | |
| 4-CH₃ | OSO₂CH₃ | H | OCH₃ | OCH₃ | CH | |
| 4-OCH₃ | OSO₂CH₃ | H | OCH₃ | OCH₃ | CH | |
| 6-CH₃ | OSO₂CH₃ | H | OCH₃ | OCH₃ | CH | |
| 6-OCH₃ | OSO₂CH₃ | H | OCH₃ | OCH₃ | CH | |
| 6-F | OSO₂CH₃ | H | OCH₃ | OCH₃ | CH | |
| 6-Cl | OSO₂CH₃ | H | OCH₃ | OCH₃ | CH | |
| H | CN | H | OCH₃ | OCH₃ | CH | |
| H | CN | H | OCH₃ | CH₃ | CH | |
| H | CN | H | Cl | OCH₃ | CH | |
| H | CN | H | CH₃ | CH₃ | CH | |
| H | CN | H | OCH₃ | OCH₃ | N | |
| H | CN | H | OCH₃ | CH₃ | N | |
| H | CN | H | OCH₂CH₃ | NHCH₃ | N | |
| H | CN | CH₃ | OCH₃ | CH₃ | N | |
| 4-CH₃ | CN | H | OCH₃ | OCH₃ | CH | |
| 4-OCH₃ | CN | H | OCH₃ | OCH₃ | CH | |
| 6-CH₃ | CN | H | OCH₃ | OCH₃ | CH | |
| 6-OCH₃ | CN | H | OCH₃ | OCH₃ | CH | |
| 6-F | CN | H | OCH₃ | OCH₃ | CH | |
| 6-Cl | CN | H | OCH₃ | OCH₃ | CH | |
| H | CH₂F | H | OCH₃ | OCH₃ | CH | |
| H | CH₂F | H | OCH₃ | CH₃ | CH | |
| H | CH₂F | H | Cl | OCH₃ | CH | |
| H | CH₂F | H | CH₃ | CH₃ | CH | |
| H | CH₂F | H | OCH₃ | OCH₃ | N | |
| H | CH₂F | H | OCH₃ | CH₃ | N | |
| H | CH₂F | H | OCH₂CH₃ | NHCH₃ | N | |
| H | CH₂F | CH₃ | OCH₃ | CH₃ | N | |
| 4-CH₃ | CH₂F | H | OCH₃ | OCH₃ | CH | |
| 4-OCH₃ | CH₂F | H | OCH₃ | OCH₃ | CH | |
| 6-CH₃ | CH₂F | H | OCH₃ | OCH₃ | CH | |
| 6-OCH₃ | CH₂F | H | OCH₃ | OCH₃ | CH | |
| 6-F | CH₂F | H | OCH₃ | OCH₃ | CH | |
| 6-Cl | CH₂F | H | OCH₃ | OCH₃ | CH | |

TABLE VI

General Formula 6

| R₁ | R₆ | R | X | Y | Z | m.p. (°C.) |
|---|---|---|---|---|---|---|
| H | SCH₃ | H | OCH₃ | OCH₃ | CH | |
| H | SCH₃ | H | OCH₃ | CH₃ | CH | |
| H | SCH₃ | H | Cl | OCH₃ | CH | |
| H | SCH₃ | H | CH₃ | CH₃ | CH | |
| H | SCH₃ | H | OCH₃ | OCH₃ | N | |
| H | SCH₃ | H | OCH₃ | CH₃ | N | |
| H | SCH₃ | H | OCH₂CH₃ | NHCH₃ | N | |
| H | SCH₃ | CH₃ | OCH₃ | CH₃ | N | |
| 4-CH₃ | SCH₃ | H | OCH₃ | OCH₃ | CH | |
| 4-Cl | SCH₃ | H | OCH₃ | OCH₃ | CH | |
| 6-CH₃ | SCH₃ | H | OCH₃ | OCH₃ | CH | |
| 6-OCH₃ | SCH₃ | H | OCH₃ | OCH₃ | CH | |
| 6-F | SCH₃ | H | OCH₃ | OCH₃ | CH | |
| 6-Cl | SCH₃ | H | OCH₃ | OCH₃ | CH | |
| H | SOCH₃ | H | OCH₃ | OCH₃ | CH | |
| H | SOCH₃ | H | OCH₃ | CH₃ | CH | |
| H | SOCH₃ | H | Cl | OCH₃ | CH | |
| H | SOCH₃ | H | CH₃ | CH₃ | CH | |
| H | SOCH₃ | H | OCH₃ | OCH₃ | N | |
| H | SOCH₃ | H | OCH₃ | CH₃ | N | |
| H | SOCH₃ | H | OCH₂CH₃ | NHCH₃ | N | |
| H | SOCH₃ | CH₃ | OCH₃ | CH₃ | N | |
| 4-CH₃ | SOCH₃ | H | OCH₃ | OCH₃ | CH | |
| 4-Cl | SOCH₃ | H | OCH₃ | OCH₃ | CH | |
| 6-CH₃ | SOCH₃ | H | OCH₃ | OCH₃ | CH | |
| 6-OCH₃ | SOCH₃ | H | OCH₃ | OCH₃ | CH | |
| 6-F | SOCH₃ | H | OCH₃ | OCH₃ | CH | |
| 6-Cl | SOCH₃ | H | OCH₃ | OCH₃ | CH | |
| H | SO—cyclopropyl | H | OCH₃ | OCH₃ | CH | |
| H | SO—cyclopropyl | H | OCH₃ | CH₃ | CH | |
| H | SO—cyclopropyl | H | Cl | OCH₃ | CH | |
| H | SO—cyclopropyl | H | CH₃ | CH₃ | CH | |
| H | SO—cyclopropyl | H | OCH₃ | OCH₃ | N | |
| H | SO—cyclopropyl | H | OCH₃ | CH₃ | N | |
| H | SO—cyclopropyl | H | OCH₂CH₃ | NHCH₃ | N | |
| H | SO—cyclopropyl | CH₃ | OCH₃ | CH₃ | N | |
| 4-CH₃ | SO—cyclopropyl | H | OCH₃ | OCH₃ | CH | |
| 4-Cl | SO—cyclopropyl | H | OCH₃ | OCH₃ | CH | |
| 6-CH₃ | SO—cyclopropyl | H | OCH₃ | OCH₃ | CH | |
| 6-OCH₃ | SO—cyclopropyl | H | OCH₃ | OCH₃ | CH | |
| 6-F | SO—cyclopropyl | H | OCH₃ | OCH₃ | CH | |
| 6-Cl | SO—cyclopropyl | H | OCH₃ | OCH₃ | CH | |
| H | SO₂—cyclopropyl | H | OCH₃ | OCH₃ | CH | |
| H | SO₂—cyclopropyl | H | OCH₃ | CH₃ | CH | |
| H | SO₂—cyclopropyl | H | Cl | OCH₃ | CH | |
| H | SO₂—cyclopropyl | H | CH₃ | CH₃ | CH | |
| H | SO₂—cyclopropyl | H | OCH₃ | OCH₃ | N | |
| H | SO₂—cyclopropyl | H | OCH₃ | CH₃ | N | |
| H | SO₂—cyclopropyl | H | OCH₂CH₃ | NHCH₃ | N | |
| H | SO₂—cyclopropyl | CH₃ | OCH₃ | CH₃ | N | |
| 4-CH₃ | SO₂—cyclopropyl | H | OCH₃ | OCH₃ | CH | |
| 4-Cl | SO₂—cyclopropyl | H | OCH₃ | OCH₃ | CH | |
| 6-CH₃ | SO₂—cyclopropyl | H | OCH₃ | OCH₃ | CH | |
| 6-OCH₃ | SO₂—cyclopropyl | H | OCH₃ | OCH₃ | CH | |
| 6-F | SO₂—cyclopropyl | H | OCH₃ | OCH₃ | CH | |
| 6-Cl | SO₂—cyclopropyl | H | OCH₃ | OCH₃ | CH | |
| H | OSO₂CH₃ | H | OCH₃ | OCH₃ | CH | |
| H | OSO₂CH₃ | H | OCH₃ | CH₃ | CH | |
| H | OSO₂CH₃ | H | Cl | OCH₃ | CH | |
| H | OSO₂CH₃ | H | CH₃ | CH₃ | CH | |
| H | OSO₂CH₃ | H | OCH₃ | OCH₃ | N | |
| H | OSO₂CH₃ | H | OCH₃ | CH₃ | N | |
| H | OSO₂CH₃ | H | OCH₂CH₃ | NHCH₃ | N | |
| H | OSO₂CH₃ | CH₃ | OCH₃ | CH₃ | N | |
| 4-CH₃ | OSO₂CH₃ | H | OCH₃ | OCH₃ | CH | |
| 4-Cl | OSO₂CH₃ | H | OCH₃ | OCH₃ | CH | |
| 6-CH₃ | OSO₂CH₃ | H | OCH₃ | OCH₃ | CH | |
| 6-OCH₃ | OSO₂CH₃ | H | OCH₃ | OCH₃ | CH | |
| 6-F | OSO₂CH₃ | H | OCH₃ | OCH₃ | CH | |
| 6-Cl | OSO₂CH₃ | H | OCH₃ | OCH₃ | CH | |
| H | CN | H | OCH₃ | OCH₃ | CH | |
| H | CN | H | OCH₃ | CH₃ | CH | |
| H | CN | H | Cl | OCH₃ | CH | |
| H | CN | H | CH₃ | CH₃ | CH | |
| H | CN | H | OCH₃ | OCH₃ | N | |
| H | CN | H | OCH₃ | CH₃ | N | |
| H | CN | H | OCH₂CH₃ | NHCH₃ | N | |
| H | CN | CH₃ | OCH₃ | CH₃ | N | |
| 4-CH₃ | CN | H | OCH₃ | OCH₃ | CH | |
| 4-Cl | CN | H | OCH₃ | OCH₃ | CH | |

TABLE VI-continued

General Formula 6

| $R_1$ | $R_6$ | R | X | Y | Z | m.p. (°C.) |
|---|---|---|---|---|---|---|
| 6-CH$_3$ | CN | H | OCH$_3$ | OCH$_3$ | CH | |
| 6-OCH$_3$ | CN | H | OCH$_3$ | OCH$_3$ | CH | |
| 6-F | CN | H | OCH$_3$ | OCH$_3$ | CH | |
| 6-Cl | CN | H | OCH$_3$ | OCH$_3$ | CH | |

TABLE VII

General Formula 7

| $R_1$ | $R_2$ | A | X | Y | m.p. (°C.) |
|---|---|---|---|---|---|
| H | SOCH$_3$ | A-2 | $X_1$=CH$_3$ | $Y_1$=CH$_2$ | |
| H | SOCH$_3$ | A-3 | $X_1$=CH$_3$ | | |
| H | SOCH$_3$ | A-3 | $X_1$=OCH$_3$ | | |
| H | SOCH$_3$ | A-4 | $X_3$=OCH$_3$ | | |
| H | SO$_2$CH$_3$ | A-2 | $X_1$=CH$_3$ | $Y_1$=CH$_2$ | |
| H | SO$_2$CH$_3$ | A-3 | $X_1$=CH$_3$ | | |
| H | SO$_2$CH$_3$ | A-3 | $X_1$=OCH$_3$ | | |
| H | SO$_2$CH$_3$ | A-4 | $X_3$=OCH$_3$ | | |
| H | SOCH$_2$CH$_3$ | A-2 | $X_1$=CH$_3$ | $Y_1$=CH$_2$ | |
| H | SOCH$_2$CH$_3$ | A-3 | $X_1$=CH$_3$ | | |
| H | SOCH$_2$CH$_3$ | A-3 | $X_1$=OCH$_3$ | | |
| H | SOCH$_2$CH$_3$ | A-4 | $X_3$=OCH$_3$ | | |
| H | SO$_2$CH$_2$CH$_3$ | A-2 | $X_1$=CH$_3$ | $Y_1$=CH$_2$ | |
| H | SO$_2$CH$_2$CH$_3$ | A-3 | $X_1$=CH$_3$ | | |
| H | SO$_2$CH$_2$CH$_3$ | A-3 | $X_1$=OCH$_3$ | | |
| H | SO$_2$CH$_2$CH$_3$ | A-4 | $X_3$=OCH$_3$ | | |
| H | SOCH$_2$CH$_2$CH$_3$ | A-2 | $X_1$=CH$_3$ | $Y_1$=CH$_2$ | |
| H | SOCH$_2$CH$_2$CH$_3$ | A-3 | $X_1$=CH$_3$ | | |
| H | SOCH$_2$CH$_2$CH$_3$ | A-3 | $X_1$=OCH$_3$ | | |
| H | SOCH$_2$CH$_2$CH$_3$ | A-4 | $X_3$=OCH$_3$ | | |
| H | SO$_2$CH$_2$CH$_2$CH$_3$ | A-2 | $X_1$=CH$_3$ | $Y_1$=CH$_2$ | |
| H | SO$_2$CH$_2$CH$_2$CH$_3$ | A-3 | $X_1$=CH$_3$ | | |
| H | SO$_2$CH$_2$CH$_2$CH$_3$ | A-3 | $X_1$=OCH$_3$ | | |
| H | SO$_2$CH$_2$CH$_2$CH$_3$ | A-4 | $X_3$=OCH$_3$ | | |
| H | SOCH(CH$_3$)$_2$ | A-2 | $X_1$=CH$_3$ | $Y_1$=CH$_2$ | |
| H | SOCH(CH$_3$)$_2$ | A-3 | $X_1$=CH$_3$ | | |
| H | SOCH(CH$_3$)$_2$ | A-3 | $X_1$=OCH$_3$ | | |
| H | SOCH(CH$_3$)$_2$ | A-4 | $X_3$=OCH$_3$ | | |
| H | SO$_2$CH(CH$_3$)$_2$ | A-2 | $X_1$=CH$_3$ | $Y_1$=CH$_2$ | |
| H | SO$_2$CH(CH$_3$)$_2$ | A-3 | $X_1$=CH$_3$ | | |
| H | SO$_2$CH(CH$_3$)$_2$ | A-3 | $X_1$=OCH$_3$ | | |
| H | SO$_2$CH(CH$_3$)$_2$ | A-4 | $X_3$=OCH$_3$ | | |
| H | SOCH$_2$CH$_2$CH$_2$CH$_3$ | A-2 | $X_1$=CH$_3$ | $Y_1$=CH$_2$ | |
| H | SOCH$_2$CH$_2$CH$_2$CH$_3$ | A-3 | $X_1$=CH$_3$ | | |
| H | SOCH$_2$CH$_2$CH$_2$CH$_3$ | A-3 | $X_1$=OCH$_3$ | | |
| H | SOCH$_2$CH$_2$CH$_2$CH$_3$ | A-4 | $X_3$=OCH$_3$ | | |
| H | SO$_2$CH$_2$CH$_2$CH$_2$CH$_3$ | A-2 | $X_1$=CH$_3$ | $Y_1$=CH$_2$ | |
| H | SO$_2$CH$_2$CH$_2$CH$_2$CH$_3$ | A-3 | $X_1$=CH$_3$ | | |
| H | SO$_2$CH$_2$CH$_2$CH$_2$CH$_3$ | A-3 | $X_1$=OCH$_3$ | | |
| H | SO$_2$CH$_2$CH$_2$CH$_2$CH$_3$ | A-4 | $X_3$=OCH$_3$ | | |
| H | S—cyclopropyl | A-2 | $X_1$=CH$_3$ | $Y_1$=CH$_2$ | |
| H | S—cyclopropyl | A-3 | $X_1$=CH$_3$ | | |
| H | S—cyclopropyl | A-3 | $X_1$=OCH$_3$ | | |
| H | S—cyclopropyl | A-4 | $X_3$=OCH$_3$ | | |
| H | SO$_2$—cyclopropyl | A-2 | $X_1$=CH$_3$ | $Y_1$=CH$_2$ | |
| H | SO$_2$—cyclopropyl | A-3 | $X_1$=CH$_3$ | | |
| H | SO$_2$—cyclopropyl | A-3 | $X_1$=OCH$_3$ | | |
| H | SO$_2$—cyclopropyl | A-4 | $X_3$=OCH$_3$ | | |
| H | OSO$_2$CH$_3$ | A-2 | $X_1$=CH$_3$ | $Y_1$=CH$_2$ | |
| H | OSO$_2$CH$_3$ | A-3 | $X_1$=CH$_3$ | | |
| H | OSO$_2$CH$_3$ | A-3 | $X_1$=OCH$_3$ | | |
| H | OSO$_2$CH$_3$ | A-4 | $X_3$=OCH$_3$ | | |
| H | OSO$_2$CH$_3$ | A-7 | $X_4$=OCH$_3$ | $Y_4$=OCH$_3$ | |
| H | OSO$_2$CH$_2$CH$_3$ | A-2 | $X_1$=CH$_3$ | $Y_1$=CH$_2$ | |
| H | OSO$_2$CH$_2$CH$_3$ | A-3 | $X_1$=CH$_3$ | | |
| H | OSO$_2$CH$_2$CH$_3$ | A-3 | $X_1$=OCH$_3$ | | |
| H | OSO$_2$CH$_2$CH$_3$ | A-4 | $X_3$=OCH$_3$ | | |
| H | OSO$_2$CF$_3$ | A-2 | $X_1$=CH$_3$ | $Y_1$=CH$_2$ | |
| H | OSO$_2$CF$_3$ | A-3 | $X_1$=CH$_3$ | | |
| H | OSO$_2$CF$_3$ | A-3 | $X_1$=OCH$_3$ | | |
| H | OSO$_2$CF$_3$ | A-4 | $X_3$=OCH$_3$ | | |
| H | OSO$_2$CCl$_3$ | A-2 | $X_1$=CH$_3$ | $Y_1$=CH$_2$ | |
| H | OSO$_2$CCl$_3$ | A-3 | $X_1$=CH$_3$ | | |
| H | OSO$_2$CCl$_3$ | A-3 | $X_1$=OCH$_3$ | | |
| H | OSO$_2$CCl$_3$ | A-4 | $X_3$=OCH$_3$ | | |
| H | CN | A-2 | $X_1$=CH$_3$ | $Y_1$=CH$_2$ | |
| H | CN | A-3 | $X_1$=CH$_3$ | | |
| H | CN | A-3 | $X_1$=OCH$_3$ | | |
| H | CN | A-4 | $X_3$=OCH$_3$ | | |
| H | CH$_2$F | A-2 | $X_1$=CH$_3$ | $Y_1$=CH$_2$ | |
| H | CH$_2$F | A-3 | $X_1$=CH$_3$ | | |
| H | CH$_2$F | A-3 | $X_1$=OCH$_3$ | | |
| H | CH$_2$F | A-4 | $X_3$=OCH$_3$ | | |
| H | CF$_2$H | A-2 | $X_1$=CH$_3$ | $Y_1$=CH$_2$ | |
| H | CF$_2$H | A-3 | $X_1$=CH$_3$ | | |
| H | CF$_2$H | A-3 | $X_1$=OCH$_3$ | | |
| H | CF$_2$H | A-4 | $X_3$=OCH$_3$ | | |

TABLE VIII

General Formula 8

| $R_1$ | $R_3$ | A | X | Y | m.p.(°C.) |
|---|---|---|---|---|---|
| H | SOCH$_3$ | A-2 | $X_1$=CH$_3$ | $Y_1$=CH$_2$ | |
| H | SOCH$_3$ | A-3 | $X_1$=CH$_3$ | | |
| H | SOCH$_3$ | A-3 | $X_1$=OCH$_3$ | | |
| H | SOCH$_3$ | A-4 | $X_3$=OCH$_3$ | | |
| H | SOCH$_2$CH$_3$ | A-2 | $X_1$=CH$_3$ | $Y_1$=CH$_2$ | |
| H | SOCH$_2$CH$_3$ | A-3 | $X_1$=CH$_3$ | | |
| H | SOCH$_2$CH$_3$ | A-3 | $X_1$=OCH$_3$ | | |
| H | SOCH$_2$CH$_3$ | A-4 | $X_3$=OCH$_3$ | | |
| H | SOCH$_2$CH$_2$CH$_3$ | A-2 | $X_1$=CH$_3$ | $Y_1$=CH$_2$ | |
| H | SOCH$_2$CH$_2$CH$_3$ | A-3 | $X_1$=CH$_3$ | | |
| H | SOCH$_2$CH$_2$CH$_3$ | A-3 | $X_1$=OCH$_3$ | | |
| H | SOCH$_2$CH$_2$CH$_3$ | A-4 | $X_3$=OCH$_3$ | | |
| H | S—cyclopropyl | A-2 | $X_1$=CH$_3$ | $Y_1$=CH$_2$ | |
| H | S—cyclopropyl | A-3 | $X_1$=CH$_3$ | | |
| H | S—cyclopropyl | A-3 | $X_1$=OCH$_3$ | | |
| H | S—cyclopropyl | A-4 | $X_3$=OCH$_3$ | | |
| H | SO$_2$—cyclopropyl | A-2 | $X_1$=CH$_3$ | $Y_1$=CH$_2$ | |
| H | SO$_2$—cyclopropyl | A-3 | $X_1$=CH$_3$ | | |
| H | SO$_2$—cyclopropyl | A-3 | $X_1$=OCH$_3$ | | |
| H | SO$_2$—cyclopropyl | A-4 | $X_3$=OCH$_3$ | | |
| H | OSO$_2$CH$_3$ | A-2 | $X_1$=CH$_3$ | $Y_1$=CH$_2$ | |
| H | OSO$_2$CH$_3$ | A-3 | $X_1$=CH$_3$ | | |
| H | OSO$_2$CH$_3$ | A-3 | $X_1$=OCH$_3$ | | |
| H | OSO$_2$CH$_3$ | A-4 | $X_3$=OCH$_3$ | | |
| H | OSO$_2$CH$_2$CH$_3$ | A-2 | $X_1$=CH$_3$ | $Y_1$=CH$_2$ | |
| H | OSO$_2$CH$_2$CH$_3$ | A-3 | $X_1$=CH$_3$ | | |
| H | OSO$_2$CH$_2$CH$_3$ | A-3 | $X_1$=OCH$_3$ | | |
| H | OSO$_2$CH$_2$CH$_3$ | A-4 | $X_3$=OCH$_3$ | | |
| H | OSO$_2$CF$_3$ | A-2 | $X_1$=CH$_3$ | $Y_1$=CH$_2$ | |
| H | OSO$_2$CF$_3$ | A-3 | $X_1$=CH$_3$ | | |
| H | OSO$_2$CF$_3$ | A-3 | $X_1$=OCH$_3$ | | |
| H | OSO$_2$CF$_3$ | A-4 | $X_3$=OCH$_3$ | | |
| H | OSO$_2$CCl$_3$ | A-2 | $X_1$=CH$_3$ | $Y_1$=CH$_2$ | |
| H | OSO$_2$CCl$_3$ | A-3 | $X_1$=CH$_3$ | | |
| H | OSO$_2$CCl$_3$ | A-3 | $X_1$=OCH$_3$ | | |
| H | OSO$_2$CCl$_3$ | A-4 | $X_3$=OCH$_3$ | | |
| H | CH$_2$F | A-2 | $X_1$=CH$_3$ | $Y_1$=CH$_2$ | |
| H | CH$_2$F | A-3 | $X_1$=CH$_3$ | | |
| H | CH$_2$F | A-3 | $X_1$=OCH$_3$ | | |
| H | CH$_2$F | A-4 | $X_3$=OCH$_3$ | | |

TABLE IX

General Formula 9

| $R_1$ | $R_4$ | A | X | Y | m.p.(°C.) |
|---|---|---|---|---|---|
| H | SOCH$_3$ | A-2 | $X_1$=CH$_3$ | $Y_1$=CH$_2$ | |
| H | SOCH$_3$ | A-3 | $X_1$=CH$_3$ | | |
| H | SOCH$_3$ | A-3 | $X_1$=OCH$_3$ | | |
| H | SOCH$_3$ | A-4 | $X_3$=OCH$_3$ | | |
| H | SOCH$_2$CH$_3$ | A-2 | $X_1$=CH$_3$ | $Y_1$=CH$_2$ | |

TABLE IX-continued

General Formula 9

| R₁ | R₄ | A | X | Y | m.p.(°C.) |
|---|---|---|---|---|---|
| H | SOCH₂CH₃ | A-3 | X₁=CH₃ | | |
| H | SOCH₂CH₃ | A-3 | X₁=OCH₃ | | |
| H | SOCH₂CH₃ | A-4 | X₃=OCH₃ | | |
| H | SOCH₂CH₂CH₃ | A-2 | X₁=CH₃ | Y₁=CH₂ | |
| H | SOCH₂CH₂CH₃ | A-3 | X₁=CH₃ | | |
| H | SOCH₂CH₂CH₃ | A-3 | X₁=OCH₃ | | |
| H | SOCH₂CH₂CH₃ | A-4 | X₃=OCH₃ | | |
| H | S—cyclopropyl | A-2 | X₁=CH₃ | Y₁=CH₂ | |
| H | S—cyclopropyl | A-3 | X₁=CH₃ | | |
| H | S—cyclopropyl | A-3 | X₁=OCH₃ | | |
| H | S—cyclopropyl | A-4 | X₃=OCH₃ | | |
| H | SO—cyclopropyl | A-2 | X₁=CH₃ | Y₁=CH₂ | |
| H | SO—cyclopropyl | A-3 | X₁=CH₃ | | |
| H | SO—cyclopropyl | A-3 | X₁=OCH₃ | | |
| H | SO—cyclopropyl | A-4 | X₃=OCH₃ | | |
| H | SO₂—cyclopropyl | A-2 | X₁=CH₃ | Y₁=CH₂ | |
| H | SO₂—cyclopropyl | A-3 | X₁=CH₃ | | |
| H | SO₂—cyclopropyl | A-3 | X₁=OCH₃ | | |
| H | SO₂—cyclopropyl | A-4 | X₃=OCH₃ | | |
| H | OSO₂CH₃ | A-2 | X₁=CH₃ | Y₁=CH₂ | |
| H | OSO₂CH₃ | A-3 | X₁=CH₃ | | |
| H | OSO₂CH₃ | A-3 | X₁=OCH₃ | | |
| H | OSO₂CH₃ | A-4 | X₃=OCH₃ | | |
| H | OSO₂CH₂CH₃ | A-2 | X₁=CH₃ | Y₁=CH₂ | |
| H | OSO₂CH₂CH₃ | A-3 | X₁=CH₃ | | |
| H | OSO₂CH₂CH₃ | A-3 | X₁=OCH₃ | | |
| H | OSO₂CH₂CH₃ | A-4 | X₃=OCH₃ | | |
| H | OSO₂CF₃ | A-2 | X₁=CH₃ | Y₁=CH₂ | |
| H | OSO₂CF₃ | A-3 | X₁=CH₃ | | |
| H | OSO₂CF₃ | A-3 | X₁=OCH₃ | | |
| H | OSO₂CF₃ | A-4 | X₃=OCH₃ | | |
| H | CH₂F | A-2 | X₁=CH₃ | Y₁=CH₂ | |
| H | CH₂F | A-3 | X₁=CH₃ | | |
| H | CH₂F | A-3 | X₁=OCH₃ | | |
| H | CH₂F | A-4 | X₃=OCH₃ | | |
| H | CN | A-2 | X₁=CH₃ | Y₁=CH₂ | |
| H | CN | A-3 | X₁=CH₃ | | |
| H | CN | A-3 | X₁=OCH₃ | | |
| H | CN | A-4 | X₃=OCH₃ | | |

TABLE X

General Formula 10

| R₁ | R₅ | A | X | Y | m.p.(°C.) |
|---|---|---|---|---|---|
| H | SOCH₃ | A-2 | X₁ = CH₃ | Y₁ = CH₂ | |
| H | SOCH₃ | A-3 | X₁ = CH₃ | | |
| H | SOCH₃ | A-3 | X₁ = OCH₃ | | |
| H | SOCH₃ | A-4 | X₃ = OCH₃ | | |
| H | SOCH₂CH₃ | A-2 | X₁ = CH₃ | Y₁ = CH₂ | |
| H | SOCH₂CH₃ | A-3 | X₁ = CH₃ | | |
| H | SOCH₂CH₃ | A-3 | X₁ = OCH₃ | | |
| H | SOCH₂CH₃ | A-4 | X₃ = OCH₃ | | |
| H | SOCH₂CH₂CH₃ | A-2 | X₁ = CH₃ | Y₁ = CH₂ | |
| H | SOCH₂CH₂CH₃ | A-3 | X₁ = CH₃ | | |
| H | SOCH₂CH₂CH₃ | A-3 | X₁ = OCH₃ | | |
| H | SOCH₂CH₂CH₃ | A-4 | X₃ = OCH₃ | | |
| H | SO₂CH₃ | A-2 | X₁ = CH₃ | Y₁ = CH₂ | |
| H | SO₂CH₃ | A-3 | X₁ = CH₃ | | |
| H | SO₂CH₃ | A-3 | X₁ = OCH₃ | | |
| H | SO₂CH₃ | A-4 | X₃ = OCH₃ | | |
| H | SO₂CH₂CH₃ | A-2 | X₁ = CH₃ | Y₁ = CH₂ | |
| H | SO₂CH₂CH₃ | A-3 | X₁ = CH₃ | | |
| H | SO₂CH₂CH₃ | A-3 | X₁ = OCH₃ | | |
| H | SO₂CH₂CH₃ | A-4 | X₃ = OCH₃ | | |
| H | SO₂CH₂CH₂CH₃ | A-2 | X₁ = CH₃ | Y₁ = CH₂ | |
| H | SO₂CH₂CH₂CH₃ | A-3 | X₁ = CH₃ | | |
| H | SO₂CH₂CH₂CH₃ | A-3 | X₁ = OCH₃ | | |
| H | SO₂CH₂CH₂CH₃ | A-4 | X₃ = OCH₃ | | |
| H | S—cyclopropyl | A-2 | X₁ = CH₃ | Y₁ = CH₂ | |
| H | S—cyclopropyl | A-3 | X₁ = CH₃ | | |
| H | S—cyclopropyl | A-3 | X₁ = OCH₃ | | |
| H | S—cyclopropyl | A-4 | X₃ = OCH₃ | | |
| H | SO—cyclopropyl | A-2 | X₁ = CH₃ | Y₁ = CH₂ | |
| H | SO—cyclopropyl | A-3 | X₁ = CH₃ | | |
| H | SO—cyclopropyl | A-3 | X₁ = OCH₃ | | |
| H | SO—cyclopropyl | A-4 | X₃ = OCH₃ | | |
| H | SO₂—cyclopropyl | A-2 | X₁ = CH₃ | Y₁ = CH₂ | |

TABLE X-continued

General Formula 10

| R₁ | R₅ | A | X | Y | m.p.(°C.) |
|---|---|---|---|---|---|
| H | SO₂—cyclopropyl | A-3 | X₁ = CH₃ | | |
| H | SO₂—cyclopropyl | A-3 | X₁ = OCH₃ | | |
| H | SO₂—cyclopropyl | A-4 | X₃ = OCH₃ | | |
| H | OSO₂CH₃ | A-2 | X₁ = CH₃ | Y₁ = CH₂ | |
| H | OSO₂CH₃ | A-3 | X₁ = CH₃ | | |
| H | OSO₂CH₃ | A-3 | X₁ = OCH₃ | | |
| H | OSO₂CH₃ | A-4 | X₃ = OCH₃ | | |
| H | CH₂F | A-2 | X₁ = CH₃ | Y₁ = CH₂ | |
| H | CH₂F | A-3 | X₁ = CH₃ | | |
| H | CH₂F | A-3 | X₁ = OCH₃ | | |
| H | CH₂F | A-4 | X₃ = OCH₃ | | |
| H | CN | A-2 | X₁ = CH₃ | Y₁ = CH₂ | |
| H | CN | A-3 | X₁ = CH₃ | | |
| H | CN | A-3 | X₁ = OCH₃ | | |
| H | CN | A-4 | X₃ = OCH₃ | | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1963, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 13

High Strength Concentrate

N-[(4,6-dimethoxypyrimidin-2-yl)aminocarbonyl]-3-(1-propylsulfonyl)-2-pyridinesulfonamide: 99%
trimethylnonyl polyethylene glycol ether: 1%.

The surfactant is sprayed upon the active ingredient in a blender and the mixture sifted through a U. S. S. no. 40 sieve (0.42 mm openings) prior to packaging. The concentrate may be formulated further for practical use.

EXAMPLE 14

Wettable Powder

N-[(4,6-dimethoxypyrimidin-2-yl)aminocarbonyl]-3-(ethylsulfonyl)-2-pyridinesulfonamide: 65%
dodecylphenol polyethylene glycol ether: 2%
sodium ligninsulfonate: 4%
sodium silicoaluminate: 6%
montmorillonite (calcined): 23%.

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 15

Aqueous Suspension

N-[(4,6-dimethoxypyrimidin-2-yl)aminocarbonyl]-3-(1-ethylsulfonyl)-2-pyridinesulfonamide: 50.0%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%.

The ingredients are blended and ground together in a sand mill to produce particles essentially all under 5 microns in size.

EXAMPLE 16

Oil Suspension

N-[(4,6-dimethoxypyrimidin-2-yl)aminocarbonyl]-3-(1-propylsulfonyl)-2-pyridinesulfonamide: 35%
blend of polyalcohol carboxylic esters and oil soluble petroleum sulfonates: 6%
xylene: 59%.

The ingredients are combined and ground together in a sand mill to produce particles essentially all below 3 microns. The product can be used directly, extended with oils, or emulsified in water.

EXAMPLE 17

Oil Suspension

N-[(4,6-dimethoxypyrimidin-2-yl)aminocarbonyl]-3-(1-propylsulfonyl)-2-pyridinesulfonamide: 25%
polyoxyethylene sorbitol hexaoleate: 5%
highly aliphatic hydrocarbon oil: 70%.

The ingredients are ground together in a sand mill until the solid particles have been reduced to under about 5 microns. The resulting thick suspension may be applied directly, but preferably after being extended with oils or emulsified in water.

EXAMPLE 18

Aqueous Suspension

N-[(4,6-dimethoxypyrimidin-2-yl)aminocarbonyl]-3-(1-propylsulfonyl)-2-pyridinesulfonamide: 25%
hydrated attapulgite: 3%
crude calcium ligninsulfonate: 10%
sodium dihydrogen phosphate: 0.5%
water: 61.5%.

The ingredients are ground together in a ball of roller mill until the solid particles have been reduced to diameters under 10 microns.

EXAMPLE 19

Wettable Powder

N-[(4,6-dimethoxypyrimidin-2-yl)aminocarbonyl]-3-(methylsulfonyloxy)-2-pyridinesulfonamide: 40%
dioctyl sodium sulfosuccinate: 1.5%
sodium ligninsulfonate: 3%
low viscosity methyl cellulose: 1.5%
attapulgite: 54%.

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 20

Granule wettable powder of Example 19: 15%
gypsum: 69%
potassium sulfate: 16%.

The ingredients are blended in a rotating mixer and water sprayed on to accomplish granulation. When most of the material has reached the desired range of 1.0 to 0.42 cm (U.S.S. #18 to 40 sieves), the granules are removed, dried, and screened. Oversized material is crushed to produce additional material in the desired range. These granules contain % active ingredient.

EXAMPLE 21

Wettable Powder

N-[(4,6-dimethoxypyrimidin-2-yl)aminocarbonyl]-3-(1-propylsulfonyl)-2-yridinesulfonamide: 50%
sodium alkylnaphthalenesulfonate: 2%
low viscosity methyl cellulose: 2%
diatomaceous earth: 46%.

The ingredients are blended, coarsely hammer-milled and the air milled to produce particles of active essentially all below 10 microns in diameter. The product is reblended before packaging.

EXAMPLE 22

Extruded Pellet

N-[(4,6-dimethoxypyrimidin-2-yl)aminocarbonyl]-3-(1-propylsulfonyl)-2-pyridinesulfonamide: 25%
anhydrous sodium sulfate: 10%
crude calcium ligninsulfonate: 5%
sodium alkylnaphthalenesulfonate: 1%
calcium/magnesium bentonite: 59%.

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 23

Wettable Powder

N-[(4,6-dimethoxypyrimidin-2-yl)aminocarbonyl]-3-(1-propylsulfonyl)-2-pyridinesulfonamide: 80%
sodium alkylnaphthalenesulfonate: 2%
sodium ligninsulfonate: 2%
synthetic amorphous silica: 3%
kaolinite: 13%.

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE 24

High Strength Concentrate

N-[(4,6-dimethoxypyrimidin-2-yl)aminocarbonyl]-3-(1-propylsulfonyl)-2-pyridinesulfonamide: 98.5%
silica aerogel: 0.5%
synthetic amorphous fine silica: 1.0%.

The ingredients are blended and ground in a hammer mill to produce a high strength concentrate essentially all passing a U.S.S. No. 50 sieve (0.3 mm openings). This material may then be formulated in a variety of ways.

Utility

Test results indicate that the compounds of the present invention are highly active preemergent or postemergent herbicides or plant growth regulants. Many of them have utility for broad-spectrum pre- and/or postemergence weed control in areas where complete control of all vegetation is desired, such as around fuel storage tanks, industrial storage areas, parking lots, drive-in theaters, around billboards, highway and railroad structures. Some of the compounds have utility for selective weed control in plantation crops, Solanaceae family crops such as tomatoes, potatoes and peppers, and crops such as wheat, barley, corn, cotton, soybeans and their fallow land. In particular, some of the compounds of this invention control weeds in corn (maize) both pre- and postemergence without significant crop damage. Some of the compounds of this invention also control weeds in potato (*Solanum tuberosum*) and tomato (*Lycopersicon esculentum*) without significant crop damage. They are particularly useful to control such problem weeds as the foxtail (Setaria spp.), fall panicum (*Panicum dichotomiflorum*), barnyardgrass (*Echinochloa crus-qalli*), seedling johnsongrass (*Sorghum halepense*) and shattercane (*Sorghum bicolor*). They can be used preemergence or postemergence and are most effective when applied postemergence to young weeds. They are also effective on certain broadleaf weeds such as lambsquarter (*Chenopodium album*), pigweed (Amaranthus spp.) and velvet leaf (*Abutilon theophrasti*).

Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.001 to 20 kg/ha, the lower rates being suggested for use on lighter soils and/or those having a low organic matter content, for plant growth modification or for situations where only short-term persistence is required.

The compounds of the invention may be used in combination with any other commerical herbicide, examples of which are those of the triazine, triazole, imidazolinone, uracil, urea, amide, diphenylether, imidazolinone, cineole, carbamate and bipyridylium types. They are particularly useful in combination with the following herbicides:

| Common Name | Chemical Name |
| --- | --- |
| alachlor | 2-chloro-2',6'-diethyl-N—(methoxymethyl)-acetanilide |
| atrazine | 2-chloro-4-(ethylamino)-6-isopropylamino)-s-triazine |
| butylate | S—ethyl-diisobutylthiocarbamate |
| cyanazine | 2-[[4-chloro-6-(ethylamino-s-triazin-2-yl]amino]-2-methylpropionitrile |
| dicamba | 3,6-dichloro-o-anisic acid |
| EPTC | S—ethyl dipropylthiocarbamate |
| linuron | 3-(3,4-dichlorophenyl)-1-methoxy-1-methylurea |

| Chemical Name | |
|---|---|
| metolachlor | 2-chloro-N—(2-ethyl-6-methyl-phenyl)-N—(2-methoxy-1-methylethyl)acetamide |
| metribuzin | 4-amino-6-tert-butyl-3-(methyl-thio)-as-triazine-5(4H)—one |
| tridiphane | 2-(3,5-dichlorophenyl)-2-(2,2,2-trichloroethyl)oxirane |
| 2,4-D | (2,4-dichlorophenoxy)acetic acid |
| bromoxynil | 3,5-dibromo-4-hydroxyphenylcyanide |
| paraquat | 1,1'-dimethyl-4,4-bipyridinium ion |
| glyphosate | N—(phosphonomethyl)glycine |
| DCPA | dimethyl tetrachloroterephthalate |
| dalapon | 2,2-dichloropropionic acid |
| dinoseb | 2-(1-methylpropyl)-4,6-dinitro-phenol |
| diphenamid | N,N—dimethyl-2,2-diphenylacetamide |
| pendimethalin | N—(1-ethylpropyl)-3,4 dimethyl-2,6 dinitrobenamine |
| oryzalin | 3,5-dinitro-N,N—dipropylsulfanil-amide |
| trifluralin | α,α,α-trifluro-2,6-dinitro-N—N—dipropyl-p-toluidine |
| chloramben | 3-amino-2,5-dichlorobenzoic acid |
| napropamide | 2-(α-naphthoxy)-N,—N—diethyl-propionamide |
| pebulate | S—propyl butylethylthiocarbamate |
| chlorpropham | isopropyl m-chlorocarbanilate |
| bensulide | S—(O,O—diisopropyl phosphoro-dithioate) ester of N—(2-mercaptoethyl)benzenesulfonamide |
| Trade Name | |
| Harmony ™ | 3-[[(4-methoxy-6-methyl-1,3,5-triazin-2-yl)aminocarbonyl]-aminosulfonyl]-2-thiophene-carboxylic acid, methyl ester |
| Cinch ® | 1-methyl-4-(1-methylethyl)-2-exo-[(2-methylphenyl)-methoxy]-7-oxabicyclo[2,2,1] heptane |
| — | 2-ethoxy-N—[[4-(2,2,2-trifluoro-ethoxy)-6-methoxy-1,3,5-triazin-2-yl]aminocarbonyl]benzene-sulfonamide |

The herbicidal properties of the subject compounds were discovered in a number of greenhouse tests. The test procedures and results follow.

Compounds

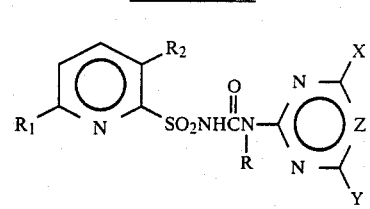

| Compound | $R_2$ | R | $R_1$ | X | Y | Z |
|---|---|---|---|---|---|---|
| 1 | $SO_2CH_2CH_2CH_3$ | H | H | $OCH_3$ | $OCH_3$ | CH |
| 2 | $SO_2CH_2CH_2CH_3$ | H | H | $CH_3$ | $OCH_3$ | CH |
| 3 | $SO_2CH_2CH_2CH_3$ | H | H | Cl | $OCH_3$ | CH |
| 4 | $SO_2CH_2CH_2CH_3$ | H | H | $CH_3$ | $CH_3$ | CH |
| 5 | $SO_2CH_2CH_2CH_3$ | H | H | $OCH_3$ | $OCH_3$ | N |
| 6 | $SO_2CH_2CH_2CH_3$ | H | H | $CH_3$ | $OCH_3$ | N |
| 7 | $SO_2CH_2CH_2CH_3$ | H | H | $OCH_2CH_3$ | $NHCH_3$ | N |
| 8 | $S(O)CH_2CH_2CH_3$ | H | H | $OCH_3$ | $OCH_3$ | CH |
| 9 | $S(O)CH_2CH_2CH_3$ | H | H | $CH_3$ | $OCH_3$ | CH |
| 10 | $S(O)CH_2CH_2CH_3$ | H | H | Cl | $OCH_3$ | CH |
| 11 | $S(O)CH_2CH_2CH_3$ | H | H | $CH_3$ | $CH_3$ | CH |
| 12 | $S(O)CH_2CH_2CH_3$ | H | H | $OCH_3$ | $OCH_3$ | N |
| 13 | $S(O)CH_2CH_2CH_3$ | H | H | $CH_3$ | $OCH_3$ | N |
| 14 | $S(O)CH_2CH_2CH_3$ | H | H | $OCH_2CH_3$ | $NHCH_3$ | N |
| 15 | $S(O)CH_2CH_3$ | H | H | $OCH_3$ | $OCH_3$ | CH |
| 16 | $S(O)CH_2CH_3$ | H | H | $OCH_3$ | $CH_3$ | CH |
| 17 | $S(O)CH_2CH_2CH_3$ | H | H | Cl | $OCH_3$ | CH |
| 18 | $S(O)CH_2CH_3$ | H | H | $CH_3$ | $CH_3$ | CH |
| 19 | $S(O)CH_2CH_3$ | H | H | $OCH_3$ | $OCH_3$ | N |
| 20 | $S(O)CH_2CH_3$ | H | H | $OCH_3$ | $CH_3$ | N |
| 21 | $SO_2CH_2CH_3$ | H | H | $OCH_3$ | $OCH_3$ | CH |
| 22 | $SO_2CH_2CH_3$ | H | H | $OCH_3$ | $CH_3$ | CH |
| 23 | $SO_2CH_2CH_3$ | H | H | Cl | $OCH_3$ | CH |
| 24 | $SO_2CH_2CH_3$ | H | H | $CH_3$ | $CH_3$ | CH |
| 25 | $SO_2CH_2CH_3$ | H | H | $OCH_3$ | $OCH_3$ | N |
| 26 | $SO_2CH_2CH_3$ | H | H | $OCH_3$ | $CH_3$ | N |
| 27 | $SO_2CH_2CH_3$ | $CH_3$ | H | $OCH_3$ | $CH_3$ | N |
| 28 | $S(O)CH_3$ | H | H | $OCH_3$ | $OCH_3$ | CH |
| 29 | $S(O)CH_3$ | H | H | $OCH_3$ | $CH_3$ | CH |
| 30 | $S(O)CH_3$ | H | H | Cl | $OCH_3$ | CH |
| 31 | $S(O)CH_3$ | H | H | $CH_3$ | $CH_3$ | CH |
| 32 | $S(O)CH_3$ | H | H | $OCH_3$ | $CH_3$ | N |
| 33 | $S(O)CH_3$ | $CH_3$ | H | $OCH_3$ | $CH_3$ | N |
| 34 | $SO_2CH_3$ | H | H | $OCH_3$ | $OCH_3$ | CH |
| 35 | $SO_2CH_3$ | H | H | $OCH_3$ | $CH_3$ | CH |
| 36 | $SO_2CH_3$ | H | H | Cl | $OCH_3$ | CH |
| 37 | $SO_2CH_3$ | H | H | $CH_3$ | $CH_3$ | CH |
| 38 | $SO_2CH_3$ | H | H | $OCH_3$ | $OCH_3$ | N |
| 39 | $SO_2CH_3$ | H | H | $OCH_3$ | $CH_3$ | N |
| 40 | $S(O)CH(CH_3)_2$ | H | H | $OCH_3$ | $OCH_3$ | CH |
| 41 | $S(O)CH(CH_3)_2$ | H | H | $OCH_3$ | $CH_3$ | CH |
| 42 | $S(O)CH(CH_3)_2$ | H | H | Cl | $OCH_3$ | CH |
| 43 | $S(O)CH(CH_3)_2$ | H | H | $CH_3$ | $CH_3$ | CH |
| 44 | $S(O)CH(CH_3)_2$ | H | H | $OCH_3$ | $OCH_3$ | N |
| 45 | $S(O)CH(CH_3)_2$ | H | H | $OCH_3$ | $CH_3$ | N |
| 46 | $SO_2CH(CH_3)_2$ | H | H | $OCH_3$ | $OCH_3$ | CH |
| 47 | $SO_2CH(CH_3)_2$ | H | H | $OCH_3$ | $CH_3$ | CH |
| 48 | $SO_2CH(CH_3)_2$ | H | H | Cl | $OCH_3$ | CH |
| 49 | $SO_2CH(CH_3)_2$ | H | H | $CH_3$ | $CH_3$ | CH |
| 50 | $SO_2CH(CH_3)_2$ | H | H | $OCH_3$ | $OCH_3$ | N |
| 51 | $SO_2CH(CH_3)_2$ | H | H | $OCH_3$ | $CH_3$ | N |
| 52 | $SO_2CH(CH_3)_2$ | $CH_3$ | H | $OCH_3$ | $CH_3$ | N |
| 53 | $SO_2(CH_2)_3CH_3$ | H | H | $OCH_3$ | $OCH_3$ | CH |
| 54 | $SO_2(CH_2)_3CH_3$ | H | H | $OCH_3$ | $CH_3$ | CH |
| 55 | $SO_2(CH_2)_3CH_3$ | H | H | Cl | $OCH_3$ | CH |
| 56 | $SO_2(CH_2)_3CH_3$ | H | H | $CH_3$ | $CH_3$ | CH |
| 57 | $SO_2(CH_2)_3CH_3$ | H | H | $OCH_3$ | $OCH_3$ | N |
| 58 | $SO_2(CH_2)_3CH_3$ | H | H | $OCH_3$ | $CH_3$ | N |
| 59 | $SO_2(CH_2)_3CH_3$ | $CH_3$ | H | $OCH_3$ | $CH_3$ | N |
| 60 | $SO_2CH_2CH_3$ | H | $CH_3$ | $OCH_3$ | $OCH_3$ | CH |
| 61 | $SO_2CH_2CH_3$ | H | $CH_3$ | $OCH_3$ | $CH_3$ | CH |
| 62 | $SO_2CH_2CH_3$ | H | $CH_3$ | $CH_3$ | $CH_3$ | CH |
| 63 | $SO_2CH_2CH_3$ | H | $CH_3$ | $OCH_3$ | $CH_3$ | N |
| 64 | $SO_2CH_2CH_3$ | H | $OCH_3$ | $OCH_3$ | $OCH_3$ | CH |
| 65 | $OSO_2CH_3$ | H | H | $OCH_3$ | $OCH_3$ | CH |
| 66 | $OSO_2CH_3$ | H | H | $OCH_3$ | $CH_3$ | CH |
| 67 | $OSO_2CH_3$ | H | H | Cl | $OCH_3$ | CH |
| 68 | $OSO_2CH_3$ | H | H | $CH_3$ | $CH_3$ | CH |
| 69 | $OSO_2CH_3$ | H | H | $OCH_3$ | $CH_3$ | N |
| 70 | $OSO_2C_2H_5$ | H | H | $OCH_3$ | $OCH_3$ | CH |
| 71 | $OSO_2C_2H_5$ | H | H | $OCH_3$ | $CH_3$ | CH |
| 72 | $OSO_2C_2H_5$ | H | H | Cl | $OCH_3$ | CH |
| 73 | $OSO_2C_2H_5$ | H | H | $CH_3$ | $CH_3$ | CH |
| 74 | $OSO_2C_2H_5$ | H | H | $OCH_3$ | $OCH_3$ | N |
| 75 | $OSO_2C_2H_5$ | H | H | $OCH_3$ | $CH_3$ | N |
| 76 | $SO_2C_2H_5$ | H | F | $OCH_3$ | $OCH_3$ | CH |
| 77 | $SO_2C_2H_5$ | H | F | $CH_3$ | $CH_3$ | CH |
| 78 | $SO_2C_2H_5$ | H | Cl | $OCH_3$ | $OCH_3$ | CH |
| 79 | $SO_2C_2H_5$ | H | Cl | Cl | $OCH_3$ | CH |
| 80 | $OSO_2C_2H_5$ | H | Cl | $CH_3$ | $CH_3$ | CH |
| 81 | $OSO_2CF_3$ | H | H | $OCH_3$ | $OCH_3$ | CH |
| 82 | $OSO_2CF_3$ | H | H | Cl | $OCH_3$ | CH |
| 83 | $OSO_2CF_3$ | H | H | $CH_3$ | $CH_3$ | CH |
| 84 | $OSO_2CF_3$ | H | H | $OCH_3$ | $OCH_3$ | N |

-continued

Compounds

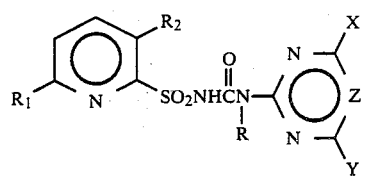

| Compound | R2 | R | R1 | X | Y | Z |
|---|---|---|---|---|---|---|
| 85 | OSO$_2$CF$_3$ | H | H | CH$_3$ | OCH$_3$ | N |
| 86 | CH$_2$Cl | H | H | OCH$_3$ | OCH$_3$ | CH |
| 87 | CH$_2$Cl | H | H | Cl | OCH$_3$ | CH |
| 88 | CH$_2$Cl | H | H | CH$_3$ | OCH$_3$ | N |
| 89 | P(O)(OCH$_2$CH$_3$)$_2$ | H | H | OCH$_3$ | OCH$_3$ | CH |
| 90 | P(O)(OCH$_2$CH$_3$)$_2$ | H | H | CH$_3$ | OCH$_3$ | CH |
| 91 | P(O)(OCH$_2$CH$_3$)$_2$ | H | H | CH$_3$ | CH$_3$ | CH |

TEST A

Seeds of crabgrass (Digitaria spp.), barnyardgrass (Echinochloa crus-galli), giant foxtail (Setaria faberi), wild oats (Avena fatua), cheatgrass (Bromus secalinus), velvetleaf (Abutilon theophrasti), morningglory (Ipomoea spp.), cocklebur (Xanthium pensylvanicum), sorghum, corn, soybean, sugarbeet, cotton, rice, wheat, barley and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

TABLE A

| RATE = KG/HA | CMPD 1 | | CMPD 2 | | CMPD 3 | | CMPD 4 | | CMPD 5 | | CMPD 6 | | CMPD 7 | | CMPD 8 | | CMPD 9 | | CMPD 10 | |
|---|---|---|---|---|---|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| | | | | | | | POSOL | | | | | | | | | | | | | |
| COTTON | 4C,9H | 9C | 0 | 0 | 0 | 2G | 0 | 0 | 0 | 0 | 0 | 0 | 0 | 0 | 2C,5G | 4C,9H | 9H | 3C,9G | 2C,3G | 3C,8H |
| MORNING GLORY | 10C | 10C | 1H | 1H | 4C,8G | 9C | 1H | 1H | 0 | 0 | 0 | 0 | 0 | 0 | 4C,9C | 10C | 5C,9G | 9C | 3C,5H | 4C,9H |
| COCKLEBUR | 9C | 10C | 1H | 1H | 3C,8G | 5C,9G | 2H,5G | 2G | 0 | 2G | 0 | 0 | 0 | 0 | 10C | 10C | 9C | 10C | 3C,7H | 4C,9H |
| NUTSEDGE | 4C,9G | 9C | 0 | 0 | 2C | 3C,8G | 0 | 0 | 0 | 0 | 0 | 0 | 0 | 0 | 2C,9G | 6C,9G | 2C,5G | 4C,8G | 0 | 2C,4G |
| CRABGRASS | 5G | 2C,8G | 0 | 9G | 0 | 0 | 0 | 0 | 0 | 2G | 0 | 0 | 0 | 0 | 0 | 2G | 0 | 3G | 5H | 0 |
| BARNYARD GRASS | 9C | 9C | 2H | 0 | 3C,7H | 3C,8H | 1H | 4C,8H | 9G | 9G | 0 | 0 | 0 | 0 | 4C,9H | 9H | 3C,7H | 3C,9H | 0 | 3C,6H |
| WILD OATS | 9G | 4C,9G | 0 | 2G | 0 | 3C,8G | 0 | 9G | 9G | 9G | 0 | 0 | 0 | 0 | 9G | 9G | 8G | 3C,9G | 0 | 2C,6G |
| WHEAT | 4C,9G | 9C | 0 | 0 | 0 | 6G | 0 | 2G | 0 | 0 | 0 | 0 | 0 | 0 | 9G | 2C,9G | 7G | 9C | 0 | 4G |
| CORN | 0 | 2H | 0 | 0 | 3C,7H | 0 | 0 | 0 | 0 | 3C,9G | 0 | 0 | 0 | 0 | 3C,7H | 4C,9G | 1H | 3C,8H | 5H | 1C,1H |
| SOYBEAN | 2C,4G | 4C,9H | 0 | 0 | 0 | 1C | 0 | 0 | 0 | 0 | 0 | 0 | 0 | 0 | 2C,7H | 4C,9G | 3H | 4C,8H | 0 | 9G |
| RICE | 9C | 6C,9G | 0 | 3G | 9C | 9C | 2G | 2G | 0 | 8G | 0 | 0 | 0 | 0 | 9C | 9C | 5C,9G | 9C | 5G | 4C,9G |
| SORGHUM | 9C | 9C | 3G | 2G | 9C | 5C,9G | 2C,2G | 2C,5G | 8G | 3C,8H | 0 | 0 | 0 | 0 | 4C,9G | 9C | 4C,9G | 5C,9G | 4C,9G | 8G |
| CHEATGRASS | 9C | 10C | 2G | 7G | 7G | 9C | 0 | 0 | 7G | 3C,8G | 0 | 0 | 0 | 0 | 9C | 9C | 3C,7G | 4C,9G | 3G | 3C,8H |
| SUGAR BEETS | 9C | 9C | 3C,7H | 3C,7H | 3C,7H | 9C | 0 | 0 | 0 | 3C,7G | 0 | 0 | 10E | 10E | 9C | 10C | 4C,8G | 9C | 6G | 3C,8H |
| VELVETLEAF | 4C,9H | 10C | 0 | 0 | 0 | 7G | 0 | 0 | 0 | 0 | 0 | 0 | 0 | 0 | 4C,9H | 10C | 4C,9H | 3C,5G | 0 | 2C,3G |
| GIANT FOXTAIL | 5C,9G | 9C | 0 | 2G | 0 | 2C,4G | 0 | 0 | 2C,5G | 2C,5G | 0 | 0 | 0 | 0 | 4C,8G | 4C,9G | 2G | 2C,8G | 0 | 1C |
| BARLEY | 6C,9G | 9C | 0 | 2G | 0 | 2C | 0 | 0 | 0 | 3C,7G | 0 | 0 | 0 | 0 | 7G | 9G | 4G | 0 | 0 | 0 |
| DOWNY BROME | 2C,8G | 5C,9G | 0 | 0 | 0 | 6G | 0 | 0 | 0 | 0 | 0 | 0 | 0 | 0 | 0 | 0 | 0 | 0 | 0 | 0 |
| | | | | | | | PRSOL | | | | | | | | | | | | | |
| COTTON | 5G | 8G | 0 | 0 | 0 | 2G | 2G | 2G | 0 | 0 | 0 | 0 | 0 | 0 | 3G | 4G | 0 | 1H | 0 | 0 |
| MORNING GLORY | 8H | 9G | 0 | 0 | 1H | 5H | 1C | 0 | 0 | 0 | 0 | 0 | 0 | 0 | 8H | 9G | 1C | 2C,8H | 0 | 3H |
| COCKLEBUR | 9H | 9H | 0 | 0 | 1C | 3G | 0 | 0 | 0 | 0 | - | - | - | - | 3C,9G | 9G | 0 | - | 0 | 0 |
| NUTSEDGE | 3C,7G | 10E | 0 | 9G | 8G | 9G | 8G | 2G | 0 | 2G | - | - | - | - | 3C,8H | 6G | 0 | 3G | 0 | 0 |
| CRABGRASS | - | 9G | 0 | 5G | 5G | 9G | 2G | 2G | 0 | 2G | - | - | - | - | 2C | 9H | 2C | 3C,8H | 0 | 3G |
| BARNYARD GRASS | 9H | 9H | 0 | 2G | 2G | 3C,7G | 4G | 0 | 2G | 2G | - | - | - | - | 6G | 3C,8H | 4G | 4C,9G | 0 | 2C,4G |
| WILD OATS | 1C | 4C,8G | 0 | 4G | 0 | 0 | 0 | 0 | 2G | 2G | - | - | - | - | 6G | 8H | 0 | 4C,8G | 0 | 0 |
| WHEAT | 8G | 10E | 0 | 2G | 0 | 0 | 2G | 0 | 0 | 0 | - | - | - | - | 3G | 3C,7H | 4G | 2G | 0 | 0 |
| CORN | 0 | 5G | 0 | 0 | 0 | 3G | 2G | 0 | 0 | 0 | - | - | - | - | 6G | 3G | 1H | 3G | 0 | 3G |
| SOYBEAN | 0 | 3G | 0 | 0 | 0 | 3C,8G | 5G | 0 | 0 | 0 | - | - | - | - | 5G | 5C,9H | 3C,8H | 4C,9H | 2G | 5G |
| RICE | 4C,9H | 10E | 0 | 6G | 3C,8G | 2C,9G | 2C,5G | 0 | 0 | 0 | - | - | 10E | - | 3C,9H | 9H | 5G | 5C,9H | 3C,7H | 3C,8H |
| SORGHUM | 10H | 10E | 3C,8G | 0 | 2G | 7G | 2C | 5G | 0 | 0 | - | - | - | - | 9G | 9H | 8H | 9G | 0 | 7G |
| CHEATGRASS | 8G | 9G | 2G | 9G | 3C,8G | 7G | 5G | 8G | 0 | 2G | - | - | - | - | 3C,8G | 4C,9G | 1C | 4C,9G | 0 | 3C,3H |
| SUGAR BEETS | 6G | 9G | 6G | 4H | 2G | 2G | 8G | 0 | 2G | 0 | - | - | - | - | 2C,2G | 8H | 0 | 2C,3H | 0 | 0 |
| VELVETLEAF | 3H | 9H | 0 | 0 | 0 | 2C | 0 | 2G | 0 | 2C,5G | - | - | - | - | 7G | 9H | 0 | 2C,9G | 0 | 0 |
| GIANT FOXTAIL | 3C,8G | 9H | 0 | 0 | 0 | 2C | 2G | 0 | 2G | 3C,7G | - | - | - | - | 6G | 9G | 0 | 4C,9G | 0 | 0 |
| BARLEY | 7G | 8G | 0 | 0 | 0 | 6G | 0 | 2G | 0 | 0 | - | - | - | - | - | - | - | - | - | - |
| DOWNY BROME | - | - | - | - | - | - | - | - | - | - | - | - | - | - | - | - | - | - | - | - |

| RATE = KG/HA | CMPD 11 | | CMPD 12 | | CMPD 13 | | CMPD 14 | | CMPD 15 | | CMPD 16 | | CMPD 17 | | CMPD 18 | | CMPD 19 | |
|---|---|---|---|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| | | | | | | | POSOL | | | | | | | | | | | |
| COTTON | 2G | 3C,8H | 0 | 0 | 0 | 0 | 0 | 0 | 3C,9H | 10C | 3C,8H | 3C,9H | 0 | 4C,8H | 2C | 3C,8H | 0 | 0 |
| MORNING GLORY | 2C,2H | 3C,7H | 2H | 4C,8H | 0 | 1C,3G | 0 | 2C,5G | 10C | 10C | 6C,9G | 6C,9G | 2C,7H | 5C,9H | 3G | 4C,8H | 0 | 0 |
| COCKLEBUR | 2C,3H | 3C,9H | 0 | 2H | 3H | 3C,9G | 0 | 0 | 10C | 10C | 9C | 9C | 1H | 4C,8H | 3C,5H | 3C,8H | 0 | 2H |
| NUTSEDGE | 0 | 0 | 0 | 2G | 0 | 0 | 2C,5G | 0 | 9G | 4C,9G | 9G | 9G | 0 | 3C,5G | 2G | 2G | 0 | 0 |
| CRABGRASS | 0 | 0 | 0 | 0 | 0 | 0 | 0 | 0 | 10C | 10C | 7G | 7G | 0 | 2G | 2G | 2G | 0 | 0 |
| BARNYARD GRASS | 3H | 5H | 0 | 2H | 0 | 5H | 7H | 0 | 3C,9G | 9G | 3C,9H | 5C,9H | 3C,7H | 5C,9H | 3C,6H | 3C,8H | 0 | 2G |
| WILD OATS | 5G | 2C,8G | 0 | 2G | 0 | 0 | 7G | 0 | 3C,9G | 3C,9G | 3C,8G | 9G | 4G | 9H | 9G | 2C,9G | 0 | 5G |
| WHEAT | 5G | 7G | 0 | 3G | 0 | 6G | 8G | 2G | 8G | 4C,9G | 9G | 9G | 3G | 7G | 8G | 9G | | |

TABLE A-continued

| | CMPD 20 | | CMPD 21 | | CMPD 22 | | CMPD 23 | | CMPD 24 | | CMPD 25 | | CMPD 26 | | CMPD 27 | | CMPD 28 | |
|---|---|---|---|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| CORN | 0 | 0 | 0 | 0 | 0 | 0 | 0 | 0 | 0 | 3C,8H | 2G | 3G | 0 | 0 | 0 | 3C,6H | 0 | 3C,9G |
| SOYBEAN | 0 | 0 | 0 | 0 | 0 | 3H | 0 | 0 | 0 | 9C | 4C,9G | 5C,9G | 0 | 3C,8H | 0 | 3C,3H | 0 | 2C,2H |
| RICE | 2C,5G | 3C,5G | 0 | 2G | 0 | 2G | 2C,6G | 10C | 0 | 10C | 3C,9G | 3C,9G | 0 | 5C,9G | 0 | 5C,9G | 0 | 0 |
| SORGHUM | 3C,7H | 9C | 0 | 2C,5G | 0 | 8G | 4C,9G | 10C | 0 | 10C | 9C | 10C | 0 | 5C,9G | 0 | 4C,9G | 0 | 0 |
| CHEATGRASS | 3G | 5G | 0 | 3G | 0 | 7G | 7H | 10C | 0 | 4G | 9C | 9C | 0 | 9C | 0 | 4C,9H | 0 | 0 |
| SUGAR BEETS | 3C,3H | 4C,8G | 0 | 2H | 0 | 3H | 7G | 7G | 0 | 2G | 4C,9H | 9C | 0 | 4C,8G | 0 | 2C,8G | 0 | 1C |
| VELVETLEAF | 2C,5G | 3C,7H | 0 | 0 | 0 | 0 | 5C,9H | 9C | 0 | 2C,5G | 4G | 9C | 0 | 9C | 0 | 9C | 0 | 3G |
| GIANT FOXTAIL | 0 | 0 | 0 | 0 | 1C,1H | 0 | 6G | 8G | 0 | 6G | 6G | 9C | 0 | 9C | 0 | 9C | 0 | 2G |
| BARLEY | 0 | 3G | 0 | 0 | 3G | 0 | 4G | 4G | 0 | 0 | 2G | 7G | 0 | 9C | 0 | 9C | 0 | 2G |
| DOWNY BROME | 0 | 0 | 0 | 2G | 0 | 0 | 3G | 3G | 0 | 4G | 0 | 3G | 0 | 4G | 0 | 6G | 0 | 2G |

PRSOL

| | | | | | | | | | | | | | | | | | | |
|---|---|---|---|---|---|---|---|---|---|---|---|---|---|---|---|---|---|---|
| COTTON | 0 | 2G | 0 | 5G | 0 | 2C,5G | 0 | 8G | 0 | 3C,9G | 0 | 5G | 0 | 0 | 0 | 0 | 0 | 0 |
| MORNING GLORY | 0 | 1H | 0 | 0 | 0 | 2C,7G | 0 | 2C,9H | 0 | 9C | 0 | 3C,7H | 0 | 2C | 0 | 2C,3H | 0 | 0 |
| COCKLEBUR | 0 | 4H | 0 | 1H | 0 | 5G | 0 | 2H | 0 | 8H | 0 | 1C,2G | 0 | 0 | 0 | 0 | 0 | — |
| NUTSEDGE | 0 | 0 | 0 | 0 | 0 | 0 | 0 | 9C | 0 | 10E | 0 | 3G | 0 | 8G | 0 | 8G | 0 | 8G |
| CRABGRASS | 0 | 2G | 0 | 0 | 0 | 3G | 0 | 2G | 0 | 9H | 0 | 2G | 0 | 3G | 0 | 0 | 0 | 0 |
| BARNYARD GRASS | 0 | 7G | 0 | 0 | 0 | 2C,5H | 0 | 4C,8H | 0 | 9H | 0 | 3G | 0 | 7G | 0 | 4G | 0 | 2C |
| WILD OATS | 0 | 2G | 0 | 0 | 0 | 0 | 0 | 6G | 0 | 3C,7G | 0 | 2C,6G | 0 | 4G | 0 | 0 | 0 | 7G |
| WHEAT | 0 | 0 | 0 | 0 | 0 | 0 | 0 | 6G | 0 | 3C,9H | 6G | 7G | 0 | 2G | 0 | 2G | 0 | 6G |
| CORN | 0 | 2G | 0 | 2G | 0 | 0 | 0 | 4G | 0 | 4G | 4G | 3G | 0 | 0 | 0 | 2G | 0 | 0 |
| SOYBEAN | 0 | 2G | 0 | 0 | 0 | 0 | 0 | 0 | 0 | 0 | 0 | 2C,6G | 2G | 2C,2H | 0 | 0 | 0 | 2G |
| RICE | 0 | 0 | 0 | 2G | 0 | 3C,4H | 0 | 3C,6H | 0 | 3C,5H | 0 | 3C,7H | 2C,4G | 9H | 2G | 9H | 0 | 8H |
| SORGHUM | 4G | 3C,5G | 0 | 9C | 0 | 3G | 0 | 10H | 0 | 10H | 4C,9H | 10H | 3C,8H | 9H | 2C,7G | 9H | 0 | 4C,9H |
| CHEATGRASS | 0 | 4G | 0 | 9C | 0 | 3C,8G | 0 | 3C,8H | 0 | 10H | 2C,7H | 9H | 5H | 3C,8H | 2G | 7G | 0 | 7G |
| SUGAR BEETS | 0 | 5H | 0 | 9C | 0 | 5G | 0 | 5C,9G | 0 | 9H | 2C,3G | 3C,8H | 5H | 8G | 2G | 0 | 0 | 5H |
| VELVETLEAF | 0 | 1H | 0 | 3H | 0 | 2C,5G | 0 | 5C,9G | 0 | 3C,9G | 0 | 2C,5G | 3G | 3C,9G | 0 | 0 | 0 | 3G |
| GIANT FOXTAIL | 0 | 0 | 0 | 0 | 0 | 2G | 0 | 3C,6H | 0 | 3C,8G | 2G | 2C | 2G | 3C,6H | 0 | 3G | 0 | 2G |
| BARLEY | 0 | 2G | 0 | 10C | 0 | 6G | 0 | 2C,8H | 0 | 5C,9H | 0 | 3G | 5G | 4G | 0 | 2C,8G | 0 | 2G |
| DOWNY BROME | 0 | 0 | 0 | 5C,9G | 0 | 0 | 0 | 7G | 0 | 3C,8G | 2G | 2C,7G | 0 | 5G | 1C | 0 | 0 | 0 |

RATE = KG/HA

| | CMPD 20 | | CMPD 21 | | CMPD 22 | | CMPD 23 | | CMPD 24 | | CMPD 25 | | CMPD 26 | | CMPD 27 | | CMPD 28 | |
|---|---|---|---|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| COTTON | 0 | 9C | 0 | 10C | 0 | 2C,5G | 2C,6G | 10C | 0 | 2G | 0 | 0 | 0 | 4C,8G | 5C,9G | 4C,9G | 3C,9G |
| MORNING GLORY | 0 | 10C | 0 | 10C | 0 | 2C,7G | 4C,9G | 10C | 0 | 2C,5H | 0 | 1H | 0 | 2C | 2C,7G | 5C,9H | 5C,9G | 10C |
| COCKLEBUR | 2H | 10C | 0 | 10C | 0 | 5G | 7H | 10C | 0 | 4G | 0 | 0 | 0 | 0 | 2C,8G | 4C,9H | 10C | 10C |
| NUTSEDGE | 0 | 9G | 0 | 10C | 0 | 0 | 7G | 7G | 0 | 2G | 0 | 0 | 0 | 0 | 0 | 0 | 0 | 2C,9G |
| CRABGRASS | 0 | 8G | 0 | 5C,9G | 0 | 3G | 5C,9H | 9C | 0 | 2C,5G | 0 | 3G | 0 | 4G | 4G | 3C,7G | 9C | 4C,9G |
| BARNYARD GRASS | 2G | 9C | 0 | 9C | 2G | 2C,5H | 6G | 9C | 0 | 2C,5G | 0 | 8G | 0 | 0 | 0 | 3C,6G | 9G | 9C |
| WILD OATS | 7G | 3C,9G | 0 | 3C,9G | 0 | 0 | 6G | 8G | 0 | 6G | 0 | 9C | 0 | 3C,8G | 0 | 4C,9G | 9G | 6C,9G |
| WHEAT | 0 | 10C | 0 | 5C,9G | 0 | 0 | 4G | 4G | 0 | 0 | 3G | 9C | 0 | 2G | 3C,8G | 2H | 9G | 6C,9G |
| CORN | 3G | 10C | 0 | 1C,4H | 1C,1H | 3C,4H | 3C,4H | 3C,8H | 0 | 3C,5H | 0 | 9C | 0 | 3C,8G | 2G | 4C,9G | 9G | 2U,9G |
| SOYBEAN | 0 | 2G | 0 | 9C | 0 | 3G | 5C,9G | 9C | 0 | 3G | 3G | 9C | 3G | 2G | 2G | 5G | 9C | 9C |
| RICE | 3C | 5C,9G | 0 | 9C | 0 | 3G | 9C | 9C | 0 | 3C,7H | 4G | 2G | 0 | 3C,8G | 3G | 4C,9G | 9C | 6C,9G |
| SORGHUM | 3C,3G | 9C | 0 | 9C | 3G | 3C,8G | 9C | 9C | 2G | 3G | 0 | 8G | 2G | 3G | 3G | 7G | 9C | 4C,9G |
| CHEATGRASS | 0 | 9C | 0 | 9C | 0 | 3G | 5C,9G | 9C | 2G | 7G | 2G | 2H | 2G | 3C,6G | 3C,6G | 6C,9G | 7G | 9C |
| SUGAR BEETS | 2H | 10C | 0 | 10C | 2G | 5G | 8G | 5C,9G | 3H | 3G | 8G | 2G | 3C,7G | 4C,9G | 6C,9G | 4C,8H | 9C |
| VELVETLEAF | 0 | 10C | 0 | 0 | 0 | 2C,5G | 4C,9G | 9C | 5G | 2C,7G | 0 | 2C | 5G | 5G | 2G | 4C,9G | 9C |
| GIANT FOXTAIL | 0 | 10C | 0 | 0 | 0 | 2G | 3G | 3C,9G | 0 | 3H | 0 | 3C,7G | 0 | 2G | 2G | 4C,9G | 9C |
| BARLEY | 0 | 0 | 0 | 5C,9G | 0 | 6G | 4C,9G | 3C,9G | 0 | 2C,7G | 7G | 3C,7G | 2G | 2G | 5G | 4C,9G | 5C,9G |
| DOWNY BROME | 0 | 4C,9G | 0 | 9C | 0 | 0 | 3G | 3C,9G | 0 | 0 | 0 | 7G | 0 | 1C | 0 | 2G | 9C |

PRSOL

TABLE A-continued

| | CMPD 29 | | CMPD 30 | | CMPD 31 | | CMPD 32 | | CMPD 33 | | CMPD 34 | | CMPD 35 | | CMPD 36 | | CMPD 37 | | CMPD 38 | |
|---|---|---|---|---|---|---|---|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| COTTON | 3G | 4C,8H | 0 | 0 | 0 | 0 | 0 | 3G | 0 | 0 | 4C,8G | 9C | 0 | 0 | 0 | 0 | 0 | 6G | 0 | 8G |
| MORNING GLORY | 3C,7H | 4C,9G | 8G | 9G | 0 | 2G | 0 | 2G | 0 | 0 | 4C,9G | 6C,9G | 0 | 3G | 2G | 6G | 0 | 7H | 0 | 7H |
| COCKLEBUR | 2C,6H | 4C,9H | 8G | 9H | 0 | 0 | 0 | 0 | 0 | 0 | 4C,9H | 10C | 0 | 2C,4G | 3C,7H | 5C,9H | — | — | — | 1H |
| NUTSEDGE | 5G | 2C,8G | 8G | 9H | 0 | 0 | 0 | 0 | 0 | 0 | 2C,9G | 3C,9G | 0 | 0 | 4C,6H | 4C,9H | 0 | 3G | 0 | 10E |
| CRABGRASS | 2C,5G | 3C,7G | 5G | 10E | — | 1H | 0 | 7G | 0 | 0 | 2C,9G | 5C,9G | 0 | 2C,8H | 5G | 3G | 0 | 8G | 0 | 2C,8G |
| BARNYARD GRASS | 4C,8H | 9C | 0 | 9H | 0 | 0 | 3C,8H | 6G | 2C,4H | 2C | 9G | 9H | 0 | 8G | 2C,8H | 2C,8G | 2H | 3C,6G | 0 | 9H |
| WILD OATS | 2C,9G | 4C,9G | 3C,6H | 3C,6H | 2H | 0 | 0 | 9H | 0 | 0 | 4C,9G | 2C,9G | 0 | 9G | 3G | 9G | 0 | 3C,8G | 0 | 3C,8G |
| WHEAT | 2C,9G | 4C,9G | 3G | 2C,4G | 4G | 2G | 0 | 4G | 0 | 0 | 9G | 4C,9G | 0 | 9G | 0 | 9G | 0 | 3C,7G | 0 | 3C,9G |
| CORN | 2C,5H | 2C,9G | 4G | 4C,9H | 4G | 3C,8G | 0 | 5G | 0 | 0 | 2C,9G | 4C,9G | 0 | 8G | 2C,4H | 9G | 0 | 3C,7H | 0 | 2C,8G |
| SOYBEAN | 4C,8H | 5C,9G | 1C | 9G | 1C,1H | 2C,9G | 2G | 2G | 0 | 2C,5H | 5C,9G | 9C | 1C,5H | 9G | 2C,6G | 0 | 2H | 5C,9H | 0 | 3C,7H |
| RICE | 5C,9G | 9C | 0 | 7G | 2C,2G | 8G | 0 | 10E | 2C,5H | 1C | 4C,9G | 5C,9G | 7G | 0 | 3C,9G | 4C,8G | 0 | 8G | 0 | 2C,8G |
| SORGHUM | 3C,7G | 4C,9G | 3C,3H | 3C,3H | 7G | 3C,8H | 0 | 10E | 1C | 0 | 6C,9G | 9C | 2G | 1C,5H | 9G | 4C,9G | 0 | 1C | 0 | 4C,9G |
| CHEATGRASS | 4C,9G | 5C,9G | 7G | 3C,9G | 0 | 4C,9G | 3G | 9H | 0 | 0 | 4C,9G | 9C | 8G | 2G | 4C,9G | 3C,9G | 2C | 8G | 0 | 9H |
| SUGAR BEETS | 2C,4G | 5C,9G | 2C | 3C,4H | 0 | 2C,5H | 0 | 8G | 2C | 0 | 2C,6H | 4C,9H | 5G | 5G | 2C,7G | 4C,8H | 3H | 1C | 0 | 7G |
| VELVETLEAF | 3C,6H | 4C,9H | 2C,5G | 5G | 3G | 2G | 0 | 2G | 1C | 0 | 10C | 10C | 2G | 8G | 3C,9G | 7G | 0 | 3G | 0 | 9H |
| GIANT FOXTAIL | 3C,7G | 4C,9G | 3G | 4C,9G | 0 | 4G | 0 | 9H | 0 | 0 | 9C | 9C | 5G | 9G | 2G | 4C,9G | 0 | 7G | 0 | 2C,7G |
| BARLEY | 3C,7G | 4C,9G | 2C,5G | 2C,5G | 3G | 2G | 0 | 7H | 0 | 0 | 10C | 4C,9G | 4G | 2C,4G | 3C,9G | 3C,8G | 0 | 8G | 0 | — |
| DOWNY BROME | | | 3G | 2C | | 3G | | 4C,9G | | 0 | 3C,8G | | | 3C,6H | | | | | | |

POSOL

| | CMPD 29 | | CMPD 30 | | CMPD 31 | | CMPD 32 | | CMPD 33 | | CMPD 34 | | CMPD 35 | | CMPD 36 | | CMPD 37 | | CMPD 38 | |
|---|---|---|---|---|---|---|---|---|---|---|---|---|---|---|---|---|---|---|---|---|
| COTTON | 3G | 5G | 0 | 0 | 2G | 2G | 0 | 4G | 0 | 0 | 8G | 8G | 0 | 4G | 4G | 8G | 0 | 0 | 0 | 0 |
| MORNING GLORY | 0 | 3G | 2G | 3C,7G | 2G | 2G | 0 | 2G | 0 | 0 | 8G | 9G | — | 0 | 0 | 7G | 0 | 0 | 0 | 0 |
| COCKLEBUR | 0 | 0 | 0 | 2C,3H | 0 | 7G | 0 | 0 | 0 | — | — | 8H | 2C | 0 | 0 | 2G | — | 0 | 0 | 0 |
| NUTSEDGE | — | 4G | — | — | 0 | — | 0 | 0 | 0 | 0 | 9G | 10E | 0 | 0 | 8G | 9G | 0 | 3G | 0 | 0 |
| CRABGRASS | 0 | 0 | 0 | 0 | 0 | 0 | 0 | 0 | 0 | 0 | 10E | 4C,9H | 0 | 8G | 8G | 10E | 0 | 8G | 0 | 0 |
| BARNYARD GRASS | 0 | 2G | 0 | 0 | 2H | 0 | 0 | 5G | 0 | 0 | 3C,8H | 9H | 0 | 2G | 2G | 9H | — | 0 | 0 | 0 |
| WILD OATS | 0 | 3G | — | 0 | 4G | 4G | 0 | 2G | 0 | 0 | 6G | 3C,8H | 4G | 8G | 4G | 0 | 0 | 0 | 0 | 0 |
| WHEAT | 0 | 0 | 0 | 0 | 4G | 3G | 0 | 0 | 0 | 0 | 8G | 4C,9H | 0 | 4G | 0 | 2G | 0 | 0 | 0 | 0 |
| CORN | 0 | 2C,4G | 0 | 2C | 1H | 2G | 0 | 2G | 0 | 0 | 2C,4G | 9G | 0 | 0 | 3G | 0 | 0 | 0 | 0 | 0 |
| SOYBEAN | 2G | 3C,3H | 2H | 2C,2H | 2C,2G | 4G | 0 | 0 | 0 | 0 | 3C,6G | 10H | 2C | 2C,5G | 0 | 2C,4G | 0 | 0 | 0 | 0 |
| RICE | 2C,3G | 3C,6G | 2G | 2G | 2G | 2G | 0 | 0 | 0 | 0 | 10H | 9G | 0 | 3G | 2C,5G | 10E | — | 0 | 0 | 0 |
| SORGHUM | 2G | 4C,5G | 0 | 2C | 3G | 3C,7G | 0 | 0 | 0 | 0 | 9G | 9G | 0 | 2G | 3C,6H | 10E | 0 | 0 | 0 | 0 |

TABLE A-continued

| | CMPD 39 | | CMPD 40 | | CMPD 41 | | CMPD 42 | | CMPD 43 | | CMPD 44 | | CMPD 45 | | CMPD 46 | | CMPD 47 | |
|---|---|---|---|---|---|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| CHEATGRASS | 2G | 3G | 0 | 0 | 0 | 0 | 0 | 2G | 0 | 6G | 9H | 0 | 0 | 2G | 0 | 7G | 0 | 0 |
| SUGAR BEETS | 5H | 7G | 2H | 7G | 2H | 2H | 2H | 2H | 7G | 9G | 0 | — | 0 | 4G | 0 | 7G | 0 | 0 |
| VELVETLEAF | 0 | 2G | 0 | 4G | 0 | 0 | 0 | 0 | 2C,8G | 0 | 3C,8G | 0 | 0 | 2C | 0 | 1C,3G | 0 | — |
| GIANT FOXTAIL | 0 | 8G | 5G | 5G | 2G | 2G | 0 | 3G | 9H | 9H | 0 | 0 | 0 | 4G | 0 | 9H | — | 0 |
| BARLEY | 0 | 2C,6G | 0 | 2C | 0 | 0 | 0 | 0 | 8G | 3C,8G | 0 | 0 | 0 | 0 | 0 | 2G | 0 | 0 |
| DOWNY BROME | | | | | | | | | | | | | | | | | | |

| | CMPD 39 | | CMPD 40 | | CMPD 41 | | CMPD 42 | | CMPD 43 | | CMPD 44 | | CMPD 45 | | CMPD 46 | | CMPD 47 | |
|---|---|---|---|---|---|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| | | | | | | | POSOL | | | | | | | | | | | |
| COTTON | 9H | 4C,9G | 3C,8H | 3C,9G | 0 | 3C,5H | 3C,3H | 0 | 2C,3G | 0 | 0 | 0 | 3C,7H | 3C,8G | 0 | 0 |
| MORNING GLORY | 4C,8H | 10C | 3C,8H | 9C | 0 | 3C,3H | 1H | 0 | 3C,6G | 0 | 2C,2H | 0 | 9C | 10C | 0 | 2G |
| COCKLEBUR | 4C,9G | 10C | 3C,9G | 9C | 2C,2H | 3C,6H | 1C,1H | 0 | 3C,6G | 1H | 0 | 2C,2H | 2C,8G | 3C,9H | 0 | 0 |
| NUTSEDGE | 8G | 9G | 0 | 0 | 0 | 0 | 1C,1H | 0 | 0 | 0 | 0 | 0 | 2C,9G | 9G | 0 | 0 |
| CRABGRASS | 0 | 3G | 9G | 3G | 0 | 3C,4G | 1H | 0 | 2G | 0 | 0 | 0 | 4G | 6G | 0 | 2G |
| BARNYARD GRASS | 3C,9H | 9C | 4C,8H | 9C | 0 | 5G | 2G | 0 | 3C,7G | 0 | 0 | 0 | 9C | 9C | 0 | 0 |
| WILD OATS | 8G | 3C,9G | 3C,8G | 3C,9G | 0 | 2G | 2G | 0 | 9G | 0 | 0 | 0 | 2G | 8G | 0 | 0 |
| WHEAT | 9G | 9G | 9G | 9G | 0 | 0 | 0 | 0 | 9G | 0 | 0 | 0 | 8G | 8G | 0 | 0 |
| CORN | 2G | 4C,9H | 0 | 4C,9H | 0 | 0 | 0 | 0 | 0 | 0 | 0 | 0 | 0 | 3G | 0 | 0 |
| SOYBEAN | 4C,9G | 4C,9G | 3C,3H | 4C,7G | 0 | 3G | 3G | 0 | 1C | 0 | 0 | 0 | 3C,7H | 4C,9G | 0 | 0 |
| RICE | 4C,9G | 5C,9G | 3C,7G | 5C,9G | 0 | 3C,9G | 3C,9G | 4G | 4C,8H | 0 | 0 | 0 | 4C,9G | 9C | 0 | 4G |
| SORGHUM | 6G | 9C | 4C,8G | 5C,9G | 0 | 3C,9G | 3C,9G | 8G | 3C,9G | 0 | 0 | 0 | 5G | 5C,8G | 0 | 4G |
| CHEATGRASS | 0 | 9C | 3C,7G | 4C,8G | 0 | 6G | 6G | 0 | 3C,6G | 0 | 0 | 0 | 3C,7G | 6C,8G | 0 | 4G |
| SUGAR BEETS | 9C | 9C | 3C,6H | 3C,7G | 0 | 3C,8G | 3C,8G | 0 | 3C,6G | 0 | 0 | 0 | 3C,7H | 4C,9H | 0 | 3H |
| VELVETLEAF | 4G | 4C,7H | 4C,9H | 4C,9G | 0 | 3C,6H | 3C,8G | 0 | 2C,2G | 0 | 0 | 0 | 2C,7H | 4C,9G | 0 | 0 |
| GIANT FOXTAIL | 0 | 3C,7G | 3C,7G | 4C,9G | 0 | 3G | 3C,7G | 4G | 3C,7G | 0 | 0 | 0 | 2C,8G | 4C,9G | 0 | 0 |
| BARLEY | 0 | 7G | 5G | 8G | 0 | 5G | 0 | 4G | 7G | 0 | 0 | 0 | 7G | 9C | 0 | 2G |
| DOWNY BROME | | | | | | | | | | | | | | | | |

| | CMPD 48 | | CMPD 49 | | CMPD 50 | | CMPD 51 | | CMPD 52 | | CMPD 53 | | CMPD 54 | | CMPD 55 | | CMPD 56 | | CMPD 57 | |
|---|---|---|---|---|---|---|---|---|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| | | | | | | | PRSOL | | | | | | | | | | | | | | |
| COTTON | 0 | 2G | 0 | 2C,5G | 0 | 2C,5H | 0 | 0 | 0 | 0 | 0 | 5G | 0 | 0 | 2C,4G | 3C,5H | 0 | 0 | 0 | 0 |
| MORNING GLORY | 0 | 7H | 0 | 9H | 2C,7H | 2C,7H | 0 | 0 | 0 | 0 | 0 | 0 | 0 | 0 | 1C | 9H | 0 | 0 | 0 | 0 |
| COCKLEBUR | 0 | 3H | 0 | 8H | 3G | 2C,4H | 0 | 0 | 0 | 0 | 0 | 0 | 0 | 0 | 0 | 9H | 0 | 0 | 0 | 0 |
| NUTSEDGE | 0 | 7G | 0 | 7G | — | 3G | 0 | 0 | 0 | 0 | 0 | 0 | 0 | 0 | 10E | 10E | 0 | 0 | 0 | 4G |
| CRABGRASS | — | 4G | 0 | 9G | 0 | 0 | 0 | 0 | 0 | 0 | 0 | 0 | 0 | 0 | 0 | 9H | 0 | 0 | 0 | 0 |
| BARNYARD GRASS | 0 | 4G | 0 | 5G | 0 | 3G | 0 | 0 | 0 | 0 | 0 | 0 | 0 | 0 | 3C,7H | 3C,7H | 0 | 0 | 0 | 0 |
| WILD OATS | 0 | 3G | 0 | 3C,7G | 7G | 0 | 0 | 0 | 0 | 0 | 0 | 0 | 0 | 0 | 4G | 4G | 0 | 0 | 0 | 2C,9H |
| WHEAT | 0 | 3G | 0 | 8G | 0 | 2C,6G | 0 | 0 | 0 | 0 | 0 | 0 | 0 | 0 | 7G | 7G | 0 | 0 | 0 | 2C,4G |
| CORN | 0 | 3G | 0 | 3C,3G | 0 | 2C,7G | 0 | 0 | 0 | 0 | 0 | 0 | 0 | 0 | 0 | 5G | 0 | 0 | 0 | 9H |
| SOYBEAN | 0 | 2H | 0 | 3C,3H | 0 | 0 | 0 | 0 | 0 | 0 | 0 | 0 | 0 | 0 | 1C,2H | 3C,9H | 0 | 0 | 0 | 0 |
| RICE | 0 | 5G | 0 | 9H | 2C,2G | 2C,2G | 2G | 0 | 0 | 0 | 0 | 0 | 0 | 0 | 4C,8H | 9H | 0 | 0 | 0 | 3C,9H |
| SORGHUM | 0 | 3C,7H | 0 | 5C,9G | 3C,5G | 3C,5G | 0 | 0 | 0 | 0 | 0 | 0 | 0 | 0 | 3C,9H | 9H | 0 | 0 | 0 | 9H |
| CHEATGRASS | 0 | 5G | 0 | 8G | 0 | 7G | 0 | 0 | 0 | 0 | 0 | 0 | 0 | 0 | 7G | 7G | 0 | 0 | 0 | 0 |
| SUGAR BEETS | — | 6H | 0 | 3C,8G | 3G | 3C,5G | 0 | 0 | 0 | 0 | 0 | 0 | 0 | 0 | 3H | 4C,8G | 0 | 0 | 0 | 4H |
| VELVETLEAF | 0 | 1C | 0 | 7H | 0 | 7G | 0 | 0 | 0 | 0 | 0 | 0 | 0 | 0 | 1C,4H | 3C,8G | 0 | 0 | 0 | 0 |
| GIANT FOXTAIL | 0 | 0 | 0 | 9H | 5G | 9H | 0 | 0 | 0 | 0 | 0 | 0 | 0 | 0 | 8G | 3C,9H | 0 | 0 | 0 | 0 |
| BARLEY | 0 | 7G | 0 | 2C,8G | 2G | 7G | 0 | 0 | 0 | 0 | 0 | 0 | 0 | 0 | 2C,9H | 2C,9H | 0 | 0 | 0 | 0 |
| DOWNY BROME | | | | | | | | | | | | | | | | | | | | |

| | CMPD 48 | | CMPD 49 | | CMPD 50 | | CMPD 51 | | CMPD 52 | | CMPD 53 | | CMPD 54 | | CMPD 55 | | CMPD 56 | | CMPD 57 | |
|---|---|---|---|---|---|---|---|---|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| | | | | | | | POSOL | | | | | | | | | | | | | | |
| COTTON | 0 | 0 | 0 | 0 | 0 | 0 | 0 | 2G | 3G | 3C,5H | 0 | 0 | 0 | 0 | 0 | 0 | 0 | 0 | 0 | 0 |

TABLE A-continued

| | CMPD 58 | | CMPD 59 | | CMPD 60 | | CMPD 61 | | CMPD 62 | | CMPD 63 | | | |
|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | | |
| MORNING GLORY | 3C,6H | 3C,8H | 0 | 0 | 2H | 0 | 0 | 0 | 2C,7H | 2C,2H | 2C,6H | 3C,5H | 3C,7G | |
| COCKLEBUR | 2C | 3C,8H | 0 | 0 | 0 | 0 | 0 | 0 | 2C,6H | 0 | 1C,4G | 3G | 3C,5G | |
| NUTSEDGE | 3G | 5G | 0 | — | — | 0 | — | 0 | 0 | 0 | 0 | 0 | 3C,8G | |
| CRABGRASS | 0 | 0 | 0 | 0 | 2G | 0 | 0 | 0 | 0 | 0 | 0 | 4H | 3C,8H | |
| BARNYARD GRASS | 4H | 7H | 0 | 0 | 2G | 2G | 0 | 0 | 2G | 2G | 4G | 0 | 2C,9G | |
| WILD OATS | 0 | 0 | 0 | 0 | 0 | 4G | 0 | 0 | 0 | 0 | 0 | 0 | 7G | |
| WHEAT | 0 | 0 | 0 | 0 | 0 | 7G | 0 | 0 | 0 | 0 | 0 | 0 | 0 | |
| CORN | 0 | 0 | 0 | 0 | 0 | 2C | 0 | 0 | 0 | 0 | 0 | 0 | 0 | |
| SOYBEAN | 2G | 2C,7G | 0 | 0 | 0 | 3G | 0 | 0 | 0 | 2C,2G | 5G | 9G | 9G | |
| RICE | 3C,7H | 3C,9G | 0 | 0 | 0 | 4G | 0 | 0 | 0 | 4H | 0 | 7G | 3C,9H | |
| SORGHUM | 3G | 5G | 0 | 0 | 0 | 4G | 0 | 0 | 0 | 2G | 0 | 4H | 9G | |
| CHEATGRASS | 1H | 2C,4G | 0 | 0 | 0 | 1H | 0 | 0 | 0 | 2C,5G | 2C,5G | 4H | 3C,7G | |
| SUGAR BEETS | 0 | — | 0 | — | 2C,7G | 0 | 0 | 0 | 0 | 5G | 6G | 3G | 2C,5G | |
| VELVETLEAF | 0 | 0 | 0 | 0 | 0 | 0 | 0 | 0 | 0 | 2G | 5G | 0 | 2C,5G | |
| GIANT FOXTAIL | 0 | 4G | 0 | 0 | 0 | 5G | 0 | 0 | 0 | 0 | 0 | 0 | 7G | |
| BARLEY | | | | | | | | | | | | | | |
| DOWNY BROME | | | | | | | | | | | | | | |
| COTTON | 0 | 1C | 0 | 0 | 0 | 0 | — | 0 | 0 | 2G | 0 | 0 | | |
| MORNING GLORY | — | 1H | 0 | 0 | 0 | 0 | 0 | 1H | 1H | 1H | 0 | 4H | | |
| COCKLEBUR | — | 0 | 0 | 0 | — | 0 | 0 | 2H | 0 | — | 0 | 2H | | |
| NUTSEDGE | 0 | 0 | 0 | 0 | 0 | 0 | 0 | 3G | 0 | 0 | 0 | 0 | | |
| CRABGRASS | 0 | 0 | 0 | 0 | 0 | 0 | 0 | 0 | 0 | 0 | 0 | 4G | | |
| BARNYARD GRASS | 0 | 0 | 0 | 0 | 0 | 0 | 0 | 0 | 0 | 2H | 0 | 6G | | |
| WILD OATS | 0 | 2G | 0 | 0 | 0 | 0 | 0 | 0 | 0 | 0 | 0 | 5G | | |
| CORN | 0 | 2G | 0 | 0 | 0 | 0 | 0 | 0 | 0 | 0 | 0 | 5G | | |
| SOYBEAN | 0 | 0 | 0 | 0 | 0 | 0 | 0 | 0 | 0 | 0 | 0 | 2G | | |
| RICE | 2C,3G | 3C,9H | 0 | 0 | 0 | 0 | 0 | 1C,4H | 0 | 0 | 0 | 6G | | |
| SORGHUM | 2C,4G | 2C,8H | 0 | 0 | 0 | 0 | 0 | 2C,8G | 0 | 2G | 0 | 2C,6G | | |
| CHEATGRASS | 0 | 2G | 0 | 0 | 0 | 0 | 0 | 4G | 0 | 1H | 2C,3H | 7G | | |
| SUGAR BEETS | 2H | 2C,4H | 0 | 0 | 0 | 0 | 0 | 2G | 0 | 1H | 0 | 6G | | |
| VELVETLEAF | 0 | 0 | 0 | 0 | 0 | 0 | 0 | 0 | 0 | 0 | 0 | 0 | | |
| GIANT FOXTAIL | 0 | 3G | 0 | 0 | 0 | 3G | 0 | 0 | 0 | 2G | 0 | 3G | | |
| BARLEY | 0 | 5G | 0 | 0 | 0 | 0 | 0 | 0 | 0 | 0 | 0 | 8G | | |
| DOWNY BROME | | | | | | | | | | | | | | |

PRSOL / POSOL

| | CMPD 61 | | CMPD 62 | | CMPD 63 | | CMPD 64 | | CMPD 65 | | CMPD 66 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| COTTON | 0 | 4G | 0 | 2G | 3C,6G | 3C,8H | 9C | 5C,9G | 9C | 9C | 4C,8G | 9C |
| MORNING GLORY | 0 | 1H | 0 | 0 | 3C,3H | 3C,7G | 10C | 10C | 10C | 10C | 10C | 10C |
| COCKLEBUR | 0 | 2H | 0 | 0 | 2C,2H | 3C,7G | 10C | 10C | 9C | 9C | 10C | 10C |
| NUTSEDGE | 0 | 3G | 0 | 0 | — | 2G | 5C,9G | 5C,9G | 5C,9G | 5C,9G | 3C,7G | 5C,9G |
| CRABGRASS | 1C,4H | 0 | 0 | 0 | 0 | 0 | 4G | 6G | 4C,9G | 6C,9G | 3C,8G | 9C |
| BARNYARD GRASS | 2C,8G | 0 | 0 | 0 | 0 | 3G | 3C,3H | 8G | 9C | 9C | 9C | 9C |
| WILD OATS | 4G | 0 | 0 | 0 | 0 | 0 | 2C,3G | 7G | 9C | 10C | 5C,9G | 9C |
| WHEAT | 2G | 0 | 0 | 0 | 0 | 0 | 5G | 3C,6G | 6C,9G | 6C,9G | 9G | 9C |
| CORN | 0 | 0 | 3H | 0 | 3C,7G | 3C,7G | 3G | 5C,9G | 7U,9C | 3U,9G | 9C | 6U,9G |
| SOYBEAN | 1C,4H | 0 | 2G | 0 | 6G | 6G | 9C | 3C,9G | 9C | 9C | 5C,9G | 9C |
| RICE | 2C,8G | 0 | 0 | 0 | 7G | 7G | 5C,9G | 3C,9G | 9C | 9C | 9C | 9C |
| SORGHUM | 4G | 0 | 0 | 0 | 0 | 0 | 4C,9G | 3C,8G | 9C | 9C | 4C,9G | 6C,9G |
| CHEATGRASS | 2G | 0 | 0 | 0 | 0 | 8G | 4C,9G | 0 | 9C | 9C | 9C | 9C |

TABLE A-continued

| | CMPD 67 | | CMPD 68 | | CMPD 69 | | CMPD 70 | | CMPD 71 | | CMPD 72 | | CMPD 73 | | CMPD 74 | | CMPD 75 | |
|---|---|---|---|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| SUGAR BEETS | 0 | 0 | 0 | 0 | 4C,8G | 10C | 3C,7G | 5C,9G | 0 | 3C,7H | 3C,8G | 3C,8H | 9C | 9C | 9C | 9C | 10C | 10C |
| VELVETLEAF | 0 | 0 | 0 | 0 | 10C | 10C | 3G | 3C,7G | 0 | 3G | 5C,9G | 3C,7G | 9C | 9C | 9C | 9C | 9C | 10C |
| GIANT FOXTAIL | 0 | 0 | 0 | 0 | 7G | 4C,9G | 0 | 0 | — | 0 | 3G | 0 | 7G | 10C | 8G | 9C | 9C | 9C |
| BARLEY | 0 | 0 | 0 | 0 | 6G | 5C,9G | 0 | 0 | 0 | 0 | 2C,6G | 0 | 3C,7G | 6C,9G | 4C,9G | 6C,9G | 4C,9G | 6C,9G |
| DOWNY BROME | | | | | | | | | | | | | | | | | | |
| | | | | | | | | | PRSOL | | | | | | | | | |
| COTTON | 0 | 0 | 0 | 0 | 3C,4G | 9C | 9C | 9C | 0 | 0 | 8G | 9G | 9G | 9G | 2G | 8G | 9G |
| MORNING GLORY | 0 | 0 | 0 | 0 | 3G | 10C | 4G | 1H | 0 | 0 | 9G | 9H | 9G | 9H | 9G | 9G | 9G |
| COCKLEBUR | 0 | 0 | — | 0 | 2G | 10C | 2H | 0 | — | 0 | 9H | 9H | 9H | 9H | 8G | 9H | 8G | 9H |
| NUTSEDGE | — | 0 | 0 | 4C,9G | 0 | 10E | 3C,6H | 0 | 0 | 4G | 5G | 10E | 10E | 9G | 10E | 4C,9G | 10E |
| CRABGRASS | 0 | 0 | 0 | 5C,9G | 4G | 3C,7G | 9C | 0 | 0 | 0 | 3G | 3C,8G | 3C,8G | 5C,9G | 3C,6G | 5C,9G | 6C,9H |
| BARNYARD GRASS | 0 | 0 | 0 | 6C,9G | 6G | 9H | 4G | 0 | 0 | 0 | 3C,6G | 9H | 9H | 9H | 9H | 9H | 9H |
| WILD OATS | 0 | 0 | 0 | 9C | 2C,2H | 2C,8G | 9C | 0 | — | 0 | 2C,4G | 3C,7G | 3C,7G | 4C,8G | 6G | 4C,8G | 3C,7G |
| WHEAT | 0 | 0 | 0 | 9C | 1C | 9H | 7G | 0 | 0 | 0 | 0 | 3C,7G | 3C,7G | 4C,9G | 2C,6G | 4C,9G | 3C,7G |
| CORN | 0 | 0 | 0 | 4C,9G | 8G | 2C,4G | 9C | 0 | 0 | 0 | 2C,4G | 3C,9H | 3C,9H | 4C,8G | 0 | 0 | 3C,9G |
| SOYBEAN | 0 | 0 | 0 | 2C,9G | 9G | 9H | 9C | 2C,2G | 0 | 0 | 3C,8H | 3C,9H | 3C,9H | 3C,9H | 3C,9H | 3C,9H | 3C,9G |
| RICE | 0 | 0 | 0 | 5C,9H | 8G | 10E | 9C | 2C,2H | 0 | 2G | 9H | 9H | 9H | 7G | 9H | 10E |
| SORGHUM | 0 | 0 | 0 | 9C | 2C,5G | 10E | 9C | 0 | 0 | 0 | 3C,8G | 3C,9H | 10E | 10E | 5G | 9H |
| CHEATGRASS | 0 | 0 | 0 | 9C | 5C,9G | 9H | 9C | 0 | 0 | 0 | 2G | 9H | 9H | 10H | 8G | 9H |
| SUGAR BEETS | 0 | 0 | 0 | 9C | 3C,3G | 10H | 5C,9G | 0 | 0 | 2H | 8G | 8G | 8G | 9G | 8G | 8G |
| VELVETLEAF | 0 | 0 | 0 | 9C | 5H | 6G | 10C | 4G | 0 | 4G | 9G | 9G | 9G | 9G | 7G | 7G |
| GIANT FOXTAIL | 0 | 0 | 0 | 4C,9H | 0 | 9G | 9C | 3H | 0 | 0 | 3C,6G | 4C,9G | 4C,9G | 3C,6H | 3C,6H | 10H |
| BARLEY | 0 | 0 | 0 | 5C,9G | 4C,8G | 3C,7G | 9C | 0 | 0 | 0 | 0 | 6G | 6G | 9C | 0 | 9C |
| DOWNY BROME | 0 | 0 | 0 | 6C,9G | 3G | 9H | 6G | 2G | 1H | 0 | 4G | 9G | 9G | 9C | 2G | 5C,9H |
| RATE = KG/HA | | | | | | | | | | | | | | | | | | |
| | | | | | | | | | POSOL | | | | | | | | | |
| COTTON | 9C | 10C | 4C,9G | 9C | 3C,5G | 3C,4G | 9C | 9C | 9C | 9C | 9C | 5C,9G | 5C,9G | 2C,5G | 2C,5G | 3C,5G |
| MORNING GLORY | 4C,9G | 10C | 4C,9H | 10C | 3C,6G | 3G | 10C | 10C | 9C | 10C | 10C | 10C | 10C | 3C,8H | 1C,1H | 3C,7H |
| COCKLEBUR | 9C | 10C | 8G | 10C | 3G | 2G | 10C | 10C | 10C | 10C | 10C | 4C,9G | 4C,9G | 3C,5H | 9C | 2C,6H |
| NUTSEDGE | 3C,9G | 5C,9G | 3C,9G | 5C,9G | 5G | 0 | 9G | 9G | 9G | 3C,9G | — | 5C,9G | 5C,9G | 5G | 0 | 3G |
| CRABGRASS | 8G | 5C,9G | 4C,8G | 6C,9G | 6G | 4G | 5G | 5G | 5G | 9C | 2C,7G | 5C,9G | 5C,9G | 7G | 3G | 3C,7G |
| BARNYARD GRASS | 9C | 9C | 9C | 9C | 9C | 9C | 9C | 9C | 9C | 9C | 9C | 10C | 10C | 9C | 9C | 9C |
| WILD OATS | 9G | 6C,9G | 5C,9G | 4C,9G | 5C,9G | 2C,2H | 7G | 5C,9G | 9C | 8G | 8G | 5C,9G | 5C,9G | 9G | 9C | 9C |
| WHEAT | 5G | 9G | 5C,9G | 2C,9G | 4U,9G | 1C | 9C | 9C | 4C,9G | 5G | 8G | 2C,9G | 2C,9G | 9G | 2C,9G | 2C,9G |
| CORN | 9H | 5U,9G | 3C,7G | 4C,9G | 4C,8H | 8G | 8G | 9C | 3C,9G | 2C,7G | 2C,7G | 3C,9H | 3C,9H | 4C,8H | 5C,9G | 5C,9G |
| SOYBEAN | 5C,9G | 5C,9G | 9C | 2C,9G | 9C | 9G | 9C | 9C | 9C | 3C,8H | 5G | 2C,5G | 2C,5G | 9C | 7H | 4C,9G |
| RICE | 9C | 5C,9G | 9C | 5C,9H | 3C,7G | 3C,3G | 7G | 3C,9G | 3C,9G | 8G | 9G | 3C,9H | 3C,9H | 9C | 9C | 9C |
| SORGHUM | 9C | 9C | 6C,9G | 9C | 5C,9G | 3C,5G | 5C,9G | 4C,9G | 4C,9G | 9C | 9C | 9C | 9C | 4C,9G | 4C,9G | 5C,9G |
| CHEATGRASS | 9C | 9C | 6C,9G | 9C | 5C,9G | 5H | 10C | 9C | 9C | 9C | 9G | 9C | 9C | 3C,6H | 3C,6H | 3C,9G |
| SUGAR BEETS | 9C | 10C | 4C,9H | 10C | 2H | 3G | 10C | 10C | 10E | 9C | 10C | 10C | 10C | 9C | 9C | 3C,6G |
| VELVETLEAF | 3C,9G | 6C,9G | 5C,9G | 10C | 4C,8G | 2G | 3C,9G | 9C | 9C | 8G | 4C,9G | 4C,9G | 4C,9G | 3C,6H | 7G | 0 |
| GIANT FOXTAIL | 8G | 3C,8G | 2C,9G | 6C,9G | 3C,7G | 3C,6G | 9G | 3C,8G | 4C,9G | 2C,7G | 2C,9G | 9C | 9C | 9C | 3C,7G | 9C |
| BARLEY | 5G | 9G | 9C | 9C | 9C | 0 | 6G | 7G | 4G | 4G | 9G | 3C,9G | 3C,9G | 9C | 9C | 9C |
| DOWNY BROME | | | | | | | | | | | | | | | | | | |
| | | | | | | | | | PRSOL | | | | | | | | | |
| COTTON | 9G | 8G | 5G | 9G | 2G | 7G | 8G | 9G | 2C,9G | 2C,7H | 2C,6G | 3C,7H | 3C,7H | 2G | 0 | 0 |
| MORNING GLORY | 9H | 9G | 7G | 9G | 4G | 6G | 7G | 9G | 9G | 9G | 9H | 9C | 9C | 0 | 0 | 0 |
| COCKLEBUR | 8G | 8G | 4G | 8H | 4G | 2H | 3C,6H | 9H | 8H | 3H | 3C,2H | 3C,8H | 3C,8H | 0 | 0 | 0 |
| NUTSEDGE | 4G | 10E | 9G | 10E | 0 | 0 | 9G | 10E | 10E | 10E | 3C,9G | 10E | 10E | 7G | 2G | 9H |
| CRABGRASS | 5C,9G | 5C,9H | 3C,8G | 9C | 0 | 0 | 4C,8G | 5G | 2C,8G | 2G | 3C,5G | 4C,9G | 4C,9G | 7G | 2G | |

TABLE A-continued

| | CMPD 76 | | CMPD 77 | | CMPD 78 | | CMPD 79 | | CMPD 80 | | CMPD 81 | | CMPD 82 | | CMPD 83 | | CMPD 84 | | CMPD 85 | |
|---|---|---|---|---|---|---|---|---|---|---|---|---|---|---|---|---|---|---|---|---|
| BARNYARD GRASS | 9H | 9H | | 5G | 9H | 0 | 6G | 5G | 2C,6G | 8H | 5G | 9H | 9H | 8H | 9H | 9H | 9H | 3G | 2G | 3C,5G | 3C,5G |
| WILD OATS | 3C,7G | 4C,8G | | 3C,6G | 4C,9G | 6G | 6G | 2C,6G | 3C,8G | 3C,7H | 3C,8G | 4C,9H | 3C,8G | 2C,9H | 3C,8H | 3C,8H | 6G | 2G | 7G |
| WHEAT | 3C,9H | 9H | | 3C,7G | 9H | 6G | 5G | 8G | 4G | 2G | 8H | 9H | 9H | 8G | 3C,7G | 3C,9H | 7G | 3G | 8G |
| CORN | 3C,9H | 9H | | 3C,8G | 3C,9G | 5G | 7G | 3C,8G | 9G | 2C,4G | 9H | 2C,4G | 3C,5G | 3C,5G | 3C,7G | 3C,9H | 3C,7G | 6G | 9G |
| SOYBEAN | 3C,8G | 9H | | 9H | 10E | 7G | 4G | 8G | 3C,7H | 2C,7G | 2C,5G | 2C,4G | 5G | 9G | 3C,5H | 3C,9H | 2G | 2G | 8G |
| RICE | 10E | 10E | | 9H | 10E | 4G | 3G | 6G | 8G | 2C,5G | 9H | 2C,7G | 10E | 5G | 10E | 10E | 7G | 7G | 9G |
| SORGHUM | 4C,9H | 10C | | 3C,9H | 10E | 3G | 3G | 8G | 2C,9H | 2C,7G | 9H | 2C,5G | 3C,9H | 9H | 9H | 9H | 3C,6G | 7G | 8G |
| CHEATGRASS | 8G | 10E | | 9H | 10E | 3G | 3G | 6G | 5G | 2C,9H | 9H | 3C,9H | 9H | 3C,9G | 3C,7H | 3C,9H | 7G | 3C,8H | 3C,9G |
| SUGAR BEETS | 9G | 9G | | 9H | 5C,9G | 4G | 4G | 3H | 9G | 2C,7G | 4C,9G | 1H | 4C,9H | 9H | 4C,9G | 4C,9G | 2H | 3G | 8G |
| VELVETLEAF | 5G | 4C,8G | | 7H | 9G | 0 | 0 | 2G | 5C,9G | 2G | 9H | 3C,3G | 3C,7H | 4C,9G | 3C,6G | 3C,8H | 0 | 2H | 4G |
| GIANT FOXTAIL | 6G | 9H | | 3C,8G | 10H | 3G | 3G | 9H | 5C,9G | 2C,7G | 3C,6G | 5C,9H | 3C,7H | 3C,8H | 0 | 9H | 7G | 3G | 3C,8H |
| BARLEY | 3C,9G | 3C,9H | | 4C,9G | 5C,9G | 2G | 0 | 3C,9H | 3C,7G | 2C,4G | 9H | 2C,5G | 3C,8H | 9H | 3C,7G | 3C,9H | 3C,7G | 2G | 9G |
| DOWNY BROME | | | | | | | | | | | | | | | | | | | | | |
| RATE = KG/HA | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |

POSOL

| | CMPD 76 | | CMPD 77 | | CMPD 78 | | CMPD 79 | | CMPD 80 | | CMPD 81 | | CMPD 82 | | CMPD 83 | | CMPD 84 | | CMPD 85 | |
|---|---|---|---|---|---|---|---|---|---|---|---|---|---|---|---|---|---|---|---|---|
| COTTON | 0 | 0 | 0 | 0 | 0 | 0 | 0 | 0 | 0 | 0 | 0 | 4C,9G | 0 | 2G | 0 | 0 | 0 | 0 | 0 | 0 |
| MORNING GLORY | 0 | 2H | 0 | 0 | 0 | 0 | 0 | 0 | 0 | 5G | 3C,6G | 4C,9G | 0 | 2G | 2C,2G | 0 | 0 | 3C,7G | 0 | 3C,4H |
| COCKLEBUR | 0 | 0 | 0 | 0 | 0 | 0 | 0 | 0 | 0 | 10C | 10C | 10C | 4C,9G | 5C,9G | 5C,9G | 2H | 4C,9H | 2H | 4C,9H |
| NUTSEDGE | 0 | 0 | 0 | 0 | 0 | 0 | — | 0 | 0 | 3C,9H | — | — | 0 | 10C | — | 0 | 0 | 0 | — |
| CRABGRASS | 0 | 0 | 0 | 0 | 0 | 0 | 1C,3G | 0 | 0 | 5C,9G | — | 3C,8G | 0 | 5G | 3G | 0 | 3C,7G | 3C,8G | — | 5G |
| BARNYARD GRASS | 0 | 0 | 0 | 0 | 0 | 0 | 0 | 0 | 0 | 3C,9H | 3C,9H | 10C | 0 | 3C,8H | 0 | 3C,6G | 0 | 4C,9G | 3C,8G | 9C |
| WILD OATS | 0 | 0 | 0 | 0 | 0 | 0 | 0 | 0 | 0 | 0 | 0 | 2C,5G | 0 | 2G | 2C,6G | 0 | 4C,9G | 0 | 0 |
| WHEAT | 0 | 0 | 0 | 0 | 0 | 0 | 0 | 0 | 0 | 0 | 0 | 2G | 3G | 3C,5G | 0 | 0 | 3C,3H | 9G | 5G |
| CORN | 4C,9H | 10C | 0 | 0 | 0 | 0 | 0 | 0 | 0 | 0 | 0 | 9C | 0 | 3C,7H | 3C,7H | 4C,8G | 3C,8G | 9G | 5C,9G |
| SOYBEAN | 0 | 0 | 0 | 0 | 0 | 0 | 0 | 0 | 0 | 9G | 4G | 3C,8G | 0 | 0 | 0 | 8G | 9G | 3C,3H | 3G |
| RICE | 0 | 0 | 0 | 0 | 0 | 0 | 0 | 0 | 0 | 4G | 5C,9G | 9C | 8G | 9C | 8G | 3C,8G | 3C,8G | 3C,8G | 9C |
| SORGHUM | 0 | 0 | 0 | 0 | 0 | 0 | 0 | 0 | 0 | 5C,9G | 4C,9G | 3C,8G | 5C,9H | 2C,8G | 4C,9G | 3C,8G | 3C,9G | 5C,9G |
| CHEATGRASS | 0 | 0 | 0 | 0 | 0 | 0 | 0 | 0 | 0 | 4C,9G | 0 | 2C,5G | 2C,5G | 4G | 5C,9G | 0 | 5C,9G |
| SUGAR BEETS | 0 | 0 | 0 | 0 | 0 | 0 | 2C,6G | 0 | 3G | 2G | 0 | 9C | 2C,4H | 9C | 3C,5H | 2H | 0 | 3C,6G |
| VELVETLEAF | 0 | 0 | 0 | 0 | 0 | 0 | 0 | 0 | 0 | 0 | 2C,4H | 5G | 0 | — | 3C,8G | 3C,7G |
| GIANT FOXTAIL | 0 | 0 | 0 | 0 | 0 | 0 | 3G | 0 | 0 | 9C | 4C,8G | 0 | 0 | 2C,5G | 4C,9G | 3C,7G | 5C,9G |
| BARLEY | 0 | 0 | 0 | 0 | 0 | 0 | 0 | 3G | 0 | 9C | 0 | 4G | 0 | 2C,5G | 0 | 0 | 0 | 3G |
| DOWNY BROME | 0 | 0 | 0 | 0 | 0 | 0 | 0 | 0 | 0 | 7G | 8G | 2C,9G | 4G | 0 | | | | |

PRSOL

| | CMPD 76 | | CMPD 77 | | CMPD 78 | | CMPD 79 | | CMPD 80 | | CMPD 81 | | CMPD 82 | | CMPD 83 | | CMPD 84 | | CMPD 85 | |
|---|---|---|---|---|---|---|---|---|---|---|---|---|---|---|---|---|---|---|---|---|
| COTTON | 0 | 0 | 0 | 0 | 0 | 0 | 0 | 0 | 0 | 0 | 8G | 2G | 2G | 0 | 0 | 0 | 0 | 0 | 0 |
| MORNING GLORY | 0 | 0 | 0 | 0 | 0 | 0 | 0 | 0 | 0 | 5G | 9G | 5G | 2G | 0 | 0 | 0 | 0 | 0 |
| COCKLEBUR | 0 | 0 | 0 | 0 | 0 | 0 | 0 | 0 | 0 | 3C,9H | 9H | 3C,3G | 3C,8H | 3C,8H | 1C | 0 | 9H | 9H |
| NUTSEDGE | 0 | 0 | 0 | 0 | 0 | 0 | — | 0 | 0 | 0 | 10E | 10E | 0 | 0 | — | 0 | 0 |
| CRABGRASS | 0 | 0 | 0 | 0 | 0 | 0 | 0 | 0 | 0 | 2G | 5G | 3G | 5G | 3G | — | 4G | 6G |
| BARNYARD GRASS | 0 | 0 | 0 | 0 | 0 | 0 | 0 | 0 | 0 | 8H | 9H | 7G | 5G | 2C,6G | 0 | 5G | 2H |
| WILD OATS | 0 | 0 | 0 | 0 | 0 | 0 | 2C,6G | 0 | 0 | 2G | 2G | 7G | 5G | 3C,7G | 0 | 9C | 0 |
| WHEAT | 0 | 0 | 0 | 0 | 0 | 0 | 0 | 0 | 0 | 0 | 2G | 0 | 3C,8G | 2C,6G | — | 3C,8G | 5G |
| CORN | 0 | 0 | 0 | 0 | 0 | 0 | 3G | 0 | 0 | 7G | 5C,9H | 6G | 3C,7H | 0 | 3C,9G | 4C,9G | 5C,9G |
| SOYBEAN | 0 | 0 | 0 | 0 | 0 | 0 | 0 | 0 | 0 | 2C,2H | 5G | 2C,3G | 0 | 0 | 2G | 3G | 9G | 3G |
| RICE | 0 | 0 | 0 | 0 | 0 | 0 | 0 | 0 | 0 | 9H | 10E | 6G | 1H | 0 | 1C | 2G | 9H | 0 |
| SORGHUM | 0 | 0 | 0 | 0 | 0 | 0 | 0 | 0 | 0 | 3C,9H | 5C,9H | 10H | 10H | 0 | — | 9H | 4G |
| CHEATGRASS | 0 | 0 | 0 | 0 | 0 | 0 | 0 | 0 | 0 | 9H | 5G | 9H | 10H | 4G | 10H | 2C,9G | 5G |
| SUGAR BEETS | 0 | 0 | 0 | 0 | 0 | 0 | 0 | 0 | 0 | 3C,9H | 5G | 3G | 0 | 6G | 2C,9G | 6G | 5G |
| VELVETLEAF | 0 | 0 | 0 | 0 | 0 | 0 | 0 | 0 | 0 | 0 | 9G | 7G | 2G | 1H | 3G | 2H | 9H |
| GIANT FOXTAIL | 0 | 0 | 0 | 0 | 0 | 0 | 0 | 0 | 3C,5G | 8G | 5H | 5G | 10H | 0 | 0 | 0 | 9H |
| BARLEY | 0 | 0 | 0 | 0 | 0 | 0 | 0 | 0 | 7G | 8G | 3G | 2G | 3G | 3G | 2G | 7G |
| | 0 | 0 | 0 | 0 | 0 | 0 | 0 | 0 | 3C,8G | 2C,9G | 3G | 7G | 2C,7G | 2C,5G | 3G | 0 | 2G |

TABLE A-continued

| RATE = KG/HA | CMPD 86 0.01 | CMPD 86 0.05 | CMPD 87 0.01 | CMPD 87 0.05 | CMPD 88 0.01 | CMPD 88 0.05 | CMPD 89 0.01 | CMPD 89 0.05 | CMPD 90 0.01 | CMPD 90 0.05 | CMPD 91 0.01 | CMPD 91 0.05 |
|---|---|---|---|---|---|---|---|---|---|---|---|---|
| | | | | POSOL | | | | | | | | |
| COTTON | 4G | 9C | 0 | 0 | 0 | 0 | 0 | 1H | 0 | 0 | 0 | 0 |
| MORNING GLORY | 3C,3G | 4C,8G | 0 | 0 | 0 | 0 | 0 | 3C,4G | 0 | 0 | 0 | 0 |
| COCKLEBUR | 1C | 5C,9G | 0 | — | 0 | 0 | 2G | 3C,6G | 0 | 0 | 0 | 0 |
| NUTSEDGE | 10C | 10C | 0 | 0 | 0 | 0 | 0 | 0 | 0 | 0 | 0 | 0 |
| CRABGRASS | 3C,6G | 9C | 0 | 0 | 0 | 0 | 0 | 0 | 0 | 0 | 0 | 0 |
| BARNYARD GRASS | 3C,8H | 9C | 0 | 0 | 0 | 0 | 2G | 4C,9H | 0 | 0 | 0 | 0 |
| WILD OATS | 0 | 3C,5G | 0 | 0 | 0 | 0 | 0 | 2C,5G | 0 | 0 | 0 | 0 |
| WHEAT | 2G | 3C,5G | 0 | 0 | 0 | 0 | 0 | 3C,5G | 0 | 0 | 0 | 0 |
| CORN | 3C,7G | 4C,9G | 2G | 0 | 0 | 0 | 0 | 3C,8H | 0 | 0 | 0 | 0 |
| SOYBEAN | 4C,9G | 9C | 0 | 0 | 0 | 0 | 1H | 3C,7G | 0 | 3H | 0 | 0 |
| RICE | 3C,8G | 9C | 0 | 0 | 0 | 0 | 0 | 6G | 0 | 0 | 0 | 0 |
| SORGHUM | 3C,7G | 3C,9G | 2C,6G | 0 | 0 | 0 | 2C,4G | 3C,9H | 0 | 0 | 0 | 0 |
| SUGAR BEETS | 10C | 10C | 3G | 0 | 0 | 0 | 4G | 10C | 0 | 3G | 0 | 0 |
| VELVETLEAF | 10C | 9C | 0 | 0 | 0 | 0 | 0 | 3C,6G | 0 | 0 | 0 | 0 |
| GIANT FOXTAIL | 2G | 9C | 0 | 0 | 0 | 0 | 0 | 2C,5G | 0 | 0 | 0 | 0 |
| BARLEY | 0 | 2C,5G | 0 | 0 | 0 | 0 | 0 | 3C,8G | 0 | 0 | 0 | 0 |
| DOWNY BROME | 5C,9G | 5C,9G | 0 | 0 | 0 | 0 | 0 | 4C,7G | 0 | 0 | 0 | 0 |
| | | | | PRSOL | | | | | | | | |
| COTTON | 0 | 0 | 0 | 0 | 0 | 0 | 0 | 0 | 0 | 0 | 0 | 0 |
| MORNING GLORY | 0 | 2C,6G | 0 | 0 | 0 | 0 | 0 | 0 | 0 | 0 | 0 | 0 |
| COCKLEBUR | 2G | 3G | 0 | 0 | 0 | 0 | 0 | 1H | 0 | 0 | 0 | 0 |
| NUTSEDGE | 0 | 5G | 0 | 0 | 0 | 0 | 0 | 0 | 0 | 0 | 0 | 0 |
| CRABGRASS | 0 | 3C,7G | 0 | 0 | 0 | 0 | 0 | 0 | 0 | 0 | 0 | 0 |
| BARNYARD GRASS | 0 | 9H | 0 | 0 | 0 | 0 | 0 | 0 | 0 | 0 | 0 | 0 |
| WILD OATS | 0 | 0 | 0 | 0 | 0 | 0 | 0 | 0 | 0 | 0 | 0 | 0 |
| WHEAT | 0 | 2G | 0 | 0 | 0 | 0 | 0 | 0 | 0 | 0 | 0 | 0 |
| CORN | 0 | 3C,6G | 0 | 0 | 0 | 0 | 0 | 0 | 0 | 0 | 0 | 0 |
| SOYBEAN | 0 | 3C,5H | 0 | 0 | 0 | 0 | 0 | 0 | 0 | 0 | 0 | 0 |
| RICE | 0 | 8G | 0 | 0 | 0 | 0 | 0 | 0 | 0 | 0 | 0 | 0 |
| SORGHUM | 2C | 9C | 0 | 0 | 0 | 0 | 0 | 0 | 0 | 0 | 0 | 0 |
| SUGAR BEETS | 5G | 9G | 0 | 0 | 0 | 0 | 0 | 0 | 0 | 0 | 0 | 0 |
| VELVETLEAF | 5G | 7G | 0 | 0 | 0 | 0 | 0 | 0 | 0 | 0 | 0 | 0 |
| GIANT FOXTAIL | 0 | 5G | 0 | 0 | 0 | 0 | 0 | 0 | 0 | 0 | 0 | 0 |
| BARLEY | 0 | 0 | 0 | 0 | 0 | 0 | 0 | 0 | 0 | 0 | 0 | 0 |
| DOWNY BROME | 0 | 7G | 0 | 0 | 0 | 0 | 0 | 0 | 0 | 0 | 0 | 0 |

It is noted that a few compounds such as Compounds 16, 37–39, 45 and 54–59 show little or no herbicidal activity at the rate tested. It is thought that they would show more herbicidal activity at higher rates.

TEST B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*) and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crus-galli*), corn (*Zea mays*), soybean (*Glycine max*) and giant foxtail (*Setaria faberi*). The third pot was planted with wheat (*Triticum aestivum*), barley (*Hordeum vulgare*), wild buckwheat (*Polgonum convolvulus* L.), cheatgrass (*Bromus secalinus* L.), sugarbeet (*Beta vulgaris*), wild oats (*Avena fatua*), viola (*Viola arvensis*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheatgrass, sugarbeet, wild oat, viola, blackgrass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 where 0=no effect and 100=complete control. A dash (-) response means no test.

Response ratings are contained in Table B.

TABLE B

POST

| RATE = G/HA | CMPD 1 | | | | | CMPD 21 | | | | CMPD 46 | | | | CMPD 60 | | | | CMPD 64 | | | | CMPD 65 | | |
|---|---|---|---|---|---|---|---|---|---|---|---|---|---|---|---|---|---|---|---|---|---|---|---|---|
| | 0001 | 0004 | 0016 | 0062 | 0250 | 0.25 | 0001 | 0004 | 0016 | 0062 | 0001 | 0004 | 0016 | 0062 | 0001 | 0004 | 0016 | 0062 | 0001 | 0004 | 0016 | 0062 | 0.25 | 0001 | 0004 | 0016 | 0062 |
| GIANT FOXTAIL | 0 | 20 | 50 | 70 | 85 | 40 | 30 | 70 | 100 | 100 | 30 | 50 | 80 | 90 | 20 | 20 | 80 | 90 | — | 30 | 50 | 80 | — | 100 | 100 | 100 | 100 |
| VELVETLEAF | 0 | 20 | 40 | 60 | 70 | 0 | 30 | 0 | 50 | 90 | 30 | 60 | 80 | 100 | 70 | 80 | 100 | 100 | 70 | 80 | 100 | 100 | 60 | 100 | 100 | 100 | 100 |
| USH11 SUGARBEET | 10 | 60 | 30 | 80 | 100 | 0 | 30 | 20 | 40 | 70 | 0 | 0 | 30 | 50 | 0 | 60 | 80 | 90 | — | 70 | 90 | 100 | 30 | 100 | 100 | 100 | 100 |
| LARGE CRABGRASS | 30 | 0 | 20 | 50 | 60 | 0 | 30 | 0 | 0 | 70 | 0 | 0 | 30 | 50 | 20 | 30 | 40 | 60 | 50 | 60 | 70 | 80 | 0 | 60 | 60 | 90 | 90 |
| PRICKLY SIDA | 0 | 20 | 20 | 60 | 70 | 0 | 30 | 0 | 20 | — | 0 | 20 | 40 | 60 | 20 | 30 | 60 | 90 | 0 | 30 | 60 | 80 | 30 | 20 | 20 | 60 | 80 |
| JIMSONWEED | 20 | 0 | 30 | 80 | 30 | 0 | 30 | 0 | 90 | 50 | 20 | 30 | 50 | 60 | 30 | 60 | 80 | 90 | 30 | 50 | 80 | 90 | 0 | 80 | 80 | 90 | 90 |
| RICE DRY SEEDED | 0 | 40 | 10 | 50 | 100 | 0 | 60 | 40 | 20 | 100 | 0 | 40 | 30 | 80 | 20 | 30 | 100 | 100 | 70 | 80 | 90 | 90 | 30 | 20 | 20 | 60 | 90 |
| COCKLEBUR | 20 | 20 | 70 | 80 | 90 | 0 | 0 | 0 | 90 | 80 | 30 | 30 | 60 | 60 | 30 | 60 | 100 | 100 | 30 | 60 | 70 | 90 | 0 | 80 | 100 | 100 | 100 |
| COKER COTTON | 0 | 20 | 80 | 80 | 100 | 0 | 30 | 30 | 60 | 80 | 0 | 40 | 50 | 60 | 20 | 30 | 80 | 90 | — | 50 | 60 | 90 | — | 20 | 30 | 80 | 100 |
| WILLMS SOYBEANS | 30 | 60 | 10 | 80 | 85 | 40 | 0 | 50 | 80 | 80 | 50 | 50 | 50 | 50 | 50 | 50 | 100 | 100 | 30 | 50 | 80 | 90 | — | 100 | 100 | 100 | 100 |
| BARNYARDGRASS | 0 | 0 | 100 | 100 | 70 | 0 | 30 | 20 | 90 | 100 | 0 | 30 | 60 | 60 | 20 | 30 | 80 | 100 | — | 60 | 70 | 60 | 60 | 90 | 90 | 100 | 90 |
| WILD OATS | 0 | 0 | 20 | 60 | 100 | 0 | 20 | 30 | 60 | 80 | 0 | 60 | 30 | 70 | 0 | 60 | 90 | 80 | 30 | 50 | 100 | 100 | — | 100 | 100 | 100 | 100 |
| IVY MORNINGLORY | 10 | 30 | 50 | 85 | 90 | 50 | 0 | 20 | 95 | 80 | 30 | 30 | 70 | 80 | 0 | 30 | 30 | 100 | 50 | 30 | 30 | 60 | 40 | 90 | 90 | 90 | 90 |
| ERA WHEAT | 10 | 10 | 60 | 70 | 10 | 0 | — | 50 | 60 | 95 | — | 50 | 80 | 0 | 70 | 50 | 50 | 70 | — | 50 | 50 | 70 | — | 90 | 90 | 90 | 100 |
| SICKLEPOD | 0 | 50 | 80 | 100 | 100 | 70 | 0 | 80 | 90 | 100 | — | 60 | 80 | 80 | 30 | 60 | 100 | 90 | 50 | 70 | 100 | 90 | 50 | 100 | 100 | 100 | 100 |
| JOHNSONGRASS | 60 | 80 | 100 | 100 | 100 | 0 | 0 | 80 | 100 | 100 | 30 | 20 | 60 | 90 | 20 | 30 | 80 | 100 | 30 | 50 | 70 | 90 | 60 | 80 | 80 | 100 | 100 |
| PURPLE NUTSEDGE | 0 | 30 | 70 | 75 | 80 | 0 | 30 | 30 | 40 | 70 | 0 | 0 | 30 | 60 | 20 | 60 | 100 | 60 | 70 | 100 | 100 | 100 | 30 | 60 | 80 | 100 | 100 |
| G4646 CORN | 0 | 0 | 0 | 0 | 10 | 0 | — | 0 | 30 | 0 | 0 | 0 | 0 | 0 | 0 | 20 | 20 | 70 | — | 20 | 30 | 60 | — | 80 | 80 | 100 | 100 |
| WILD BUCKWHEAT | 0 | 30 | 40 | 70 | — | 20 | 20 | 50 | 50 | — | — | 50 | 50 | 90 | 70 | 70 | 60 | 80 | 60 | 60 | 50 | 90 | — | 100 | 100 | 100 | 100 |
| BLACKGRASS | 50 | 50 | 70 | 85 | 90 | 0 | 50 | 80 | 100 | 100 | — | 50 | 50 | 100 | 60 | 100 | 100 | 100 | — | 50 | 70 | 90 | — | 80 | 80 | 100 | 90 |
| ALTEX RAPE | 20 | 60 | 90 | 100 | 100 | 50 | 60 | 100 | 100 | — | — | 50 | 60 | 100 | 80 | 100 | 100 | 100 | — | 100 | 100 | 100 | — | 60 | 80 | 100 | 100 |
| KLAGES BARLEY | 0 | 20 | 30 | 80 | 90 | 20 | 30 | 60 | 100 | 70 | — | 60 | 50 | 60 | 30 | 40 | 70 | 70 | 0 | 30 | 50 | 70 | — | 100 | 100 | 100 | 100 |
| GREEN FOXTAIL | 0 | 20 | 30 | 75 | 85 | 60 | 20 | 100 | 100 | 100 | — | 30 | 30 | 80 | 40 | 80 | 90 | 100 | — | 30 | 30 | 70 | — | 70 | 80 | 100 | 100 |
| CHEAT GRASS | 20 | 30 | 65 | 85 | 95 | 20 | 30 | 30 | 50 | 90 | 30 | 60 | 30 | 70 | 50 | 60 | 60 | 70 | 0 | 30 | 50 | 70 | 70 | 90 | 90 | 90 | 90 |
| FIELD VIOLET | — | 0 | 0 | 20 | — | 0 | — | 40 | 0 | — | — | 0 | 0 | 0 | 0 | 0 | 0 | 0 | — | — | — | — | — | 100 | 100 | 100 | 100 |
| LAMBSQUARTER | 0 | 0 | 0 | 20 | 50 | 0 | — | 0 | 100 | — | 0 | 50 | 30 | 50 | 30 | 50 | 80 | 90 | 60 | 70 | 80 | 90 | 80 | 100 | 100 | 100 | 100 |
| CHICKWEED SPP. | — | 0 | 20 | 20 | — | — | — | — | — | — | — | 50 | 70 | 90 | — | 60 | 70 | 70 | — | 50 | 70 | 90 | — | — | 90 | 100 | 100 |

PRE

| RATE = G/HA | CMPD 1 | | | | CMPD 21 | | | | CMPD 46 | | | | CMPD 60 | | | | CMPD 64 | | | | CMPD 65 | | | |
|---|---|---|---|---|---|---|---|---|---|---|---|---|---|---|---|---|---|---|---|---|---|---|---|---|
| | 0001 | 0004 | 0016 | 0062 | 0001 | 0004 | 0016 | 0062 | 0001 | 0004 | 0016 | 0062 | 0250 | 0004 | 0016 | 0062 | 0250 | 0001 | 0004 | 0016 | 0062 | 0250 | 0001 | 0004 | 0016 | 0062 |
| GIANT FOXTAIL | 20 | 20 | 80 | | 70 | 90 | 100 | | 50 | 80 | 90 | 100 | | 30 | 40 | 80 | | 0 | 0 | 50 | 70 | 90 | 0 | 20 | 100 | 100 |
| VELVETLEAF | 0 | 20 | 30 | | 50 | 70 | 90 | | 30 | 60 | 60 | 100 | 100 | — | 90 | 90 | 100 | 50 | 70 | 70 | 90 | 100 | 0 | 20 | 80 | 90 |
| USH11 SUGARBEET | 20 | 60 | 70 | | 60 | 50 | 70 | | 70 | 90 | 100 | — | — | 60 | 60 | 70 | 80 | 30 | 80 | 90 | 100 | 70 | 70 | 90 | 100 | 100 |
| LARGE CRABGRASS | 0 | 0 | 0 | | 50 | 40 | 70 | | 30 | 30 | 50 | 70 | 80 | 0 | 50 | 50 | 70 | 20 | 0 | 30 | 50 | 70 | 20 | 60 | 60 | 90 |
| PRICKLY SIDA | — | — | 0 | | 60 | 70 | 80 | | 20 | 30 | 30 | 60 | 80 | 0 | 60 | 70 | 80 | 0 | 30 | 30 | 70 | 80 | 0 | 30 | 50 | 90 |
| JIMSONWEED | — | 0 | — | | 70 | 70 | 80 | | 30 | 40 | 50 | 60 | 80 | 0 | 50 | 70 | 90 | 0 | 20 | 50 | 70 | 90 | 0 | 20 | 70 | 70 |
| RICE DRY SEEDED | 20 | 85 | 90 | | 70 | 100 | 100 | | 20 | 100 | 70 | 100 | 60 | 20 | 60 | 60 | 100 | 30 | 50 | 70 | 70 | 70 | 0 | 30 | 70 | 100 |
| COCKLEBUR | 0 | 10 | 30 | | 30 | 50 | 50 | | 30 | 30 | 40 | 60 | — | 30 | 60 | 80 | 100 | 30 | 30 | 70 | 80 | 80 | 0 | 20 | 20 | 70 |
| COKER COTTON | 0 | 0 | 0 | | 0 | 30 | 30 | | 30 | 30 | 50 | 80 | 100 | 0 | 50 | 70 | 80 | 30 | 30 | 60 | 80 | 80 | 0 | 20 | 50 | 100 |
| WILLMS SOYBEANS | 20 | 20 | 50 | | 60 | 50 | 50 | | 0 | 30 | 40 | 60 | — | 20 | 50 | 60 | 90 | 30 | 30 | 50 | 50 | 70 | 20 | 20 | 20 | 50 |
| BARNYARDGRASS | 0 | 0 | 80 | | 30 | 30 | 90 | | 30 | 30 | 70 | 90 | 100 | 30 | 50 | 90 | 100 | 30 | 50 | 70 | 80 | 70 | 0 | 30 | 40 | 100 |
| WILD OATS | 0 | 20 | 80 | | 60 | 60 | 90 | | 50 | 50 | 40 | 80 | 90 | 0 | 60 | 70 | 70 | 30 | 50 | 60 | 50 | 70 | 30 | 40 | 80 | 100 |
| IVY MORNINGLORY | 10 | 20 | 80 | | 30 | 60 | 100 | | 30 | 50 | 70 | 70 | 90 | 30 | 80 | 80 | 100 | 50 | 50 | 50 | 70 | 90 | 40 | 80 | 80 | 100 |
| ERA WHEAT | 0 | 0 | 80 | | 60 | 60 | 90 | | 50 | 50 | 50 | 50 | 80 | 20 | 30 | 60 | 60 | 30 | 30 | 30 | 70 | 70 | 30 | 60 | 90 | 100 |
| SICKLEPOD | — | — | — | | 70 | 80 | 90 | | 30 | 70 | 80 | 100 | 100 | — | 30 | 50 | 100 | 20 | 0 | 50 | 100 | 100 | 30 | 50 | 80 | 100 |
| JOHNSONGRASS | 60 | 85 | 100 | | 30 | 60 | 100 | | 70 | 60 | 70 | 100 | — | 30 | 80 | 90 | 100 | — | 30 | 50 | 100 | 100 | — | 30 | 90 | 90 |
| PURPLE NUTSEDGE | 20 | 30 | 90 | | 30 | 60 | 90 | | 30 | 60 | 70 | 80 | 100 | 0 | 20 | 80 | 100 | 20 | 80 | 90 | 100 | 90 | 0 | 0 | 90 | 90 |
| G4646 CORN | 0 | 0 | 0 | | 0 | 0 | 0 | | 0 | 0 | 0 | 30 | — | 0 | 0 | 20 | 40 | 0 | 0 | 30 | 60 | 90 | 0 | 0 | 90 | 90 |

TABLE B-continued

| | | | | | | | | | | | | | | |
|---|---|---|---|---|---|---|---|---|---|---|---|---|---|---|
| WILD BUCKWHEAT | 0 | 50 | 70 | 80 | 90 | 90 | 80 | 70 | 90 | 50 | 70 | 80 | 100 | 100 |
| BLACKGRASS | 0 | 20 | 80 | 85 | 90 | 100 | 70 | 60 | 90 | — | 80 | 90 | 100 | 90 |
| ALTEX RAPE | 0 | 50 | 80 | 90 | 95 | 100 | 70 | 70 | 100 | 20 | 90 | 100 | 100 | 100 |
| KLAGES BARLEY | 20 | 30 | 80 | 80 | 90 | 90 | 30 | 30 | 90 | 0 | 30 | 60 | 100 | 80 |
| GREEN FOXTAIL | 20 | 90 | 95 | 100 | 99 | 100 | 30 | 50 | 100 | 20 | 70 | 70 | 80 | 100 |
| CHEAT GRASS | 30 | 70 | 90 | 100 | 100 | 80 | 30 | 30 | 70 | 0 | 70 | 80 | 100 | 100 |
| FIELD VIOLET | | | | | | | 50 | 60 | 90 | 30 | 70 | 20 | 100 | 100 |
| LAMBSQUARTER | 0 | 0 | 50 | 70 | 80 | 90 | 50 | 50 | 100 | — | 90 | 100 | 100 | 100 |
| CHICKWEED SPP. | | | | | | | 60 | 50 | 90 | — | 90 | 100 | 100 | 100 |

POST

| | CMPD 66 | | | | CMPD 67 | | | | CMPD 68 | | | |
|---|---|---|---|---|---|---|---|---|---|---|---|---|
| RATE = G/HA | 0001 | 0004 | 0016 | 0062 | 0001 | 0004 | 0016 | 0062 | 0001 | 0004 | 0016 | 0062 |
| GIANT FOXTAIL | — | 50 | 100 | 100 | 0 | 30 | 100 | 100 | — | 90 | 100 | 100 |
| VELVETLEAF | 20 | 70 | 90 | 100 | 50 | 80 | 90 | 100 | 40 | 90 | 100 | 100 |
| USH11 SUGARBEET | 0 | 50 | 100 | 100 | — | 100 | 100 | 100 | — | 90 | 100 | 100 |
| LARGE CRABGRASS | 0 | 40 | 60 | 90 | 30 | 40 | 80 | 100 | 30 | 70 | 100 | 90 |
| PRICKLY SIDA | 0 | 30 | 70 | 100 | 30 | 70 | 90 | 100 | 20 | 80 | 100 | 100 |
| JIMSONWEED | 20 | 60 | 90 | 100 | 70 | 100 | 100 | 100 | 70 | 100 | 100 | 100 |
| RICE DRY SEEDED | 0 | 30 | 90 | 40 | 40 | 80 | 100 | 100 | 50 | 80 | 100 | 90 |
| COCKLEBUR | 0 | 0 | 30 | 100 | 0 | 60 | 80 | 100 | 40 | 30 | 80 | 100 |
| COKER COTTON | — | 80 | 100 | 40 | 90 | 90 | 100 | 100 | 0 | 100 | 100 | 100 |
| WILLMS SOYBEANS | 80 | 80 | 100 | 100 | 100 | 100 | 100 | — | 30 | 100 | 100 | 100 |
| BARNYARDGRASS | 30 | 80 | 90 | 100 | 90 | 100 | 100 | 100 | 60 | 100 | 100 | 100 |
| WILD OATS | — | 40 | 80 | 100 | — | 30 | 80 | 100 | — | 90 | 100 | 100 |
| ERA WHEAT | 20 | 80 | 90 | 100 | 60 | 90 | 100 | 100 | 30 | 80 | 100 | 100 |
| SICKLEPOD | 0 | 30 | 60 | 100 | — | 30 | 40 | 70 | 30 | 70 | 100 | 100 |
| JOHNSONGRASS | 40 | 50 | 90 | 100 | 60 | 100 | 100 | 100 | 70 | 80 | 100 | 100 |
| PURPLE NUTSEDGE | 0 | 20 | 40 | 80 | — | 80 | 80 | 100 | 30 | 80 | 100 | 100 |
| G4646 CORN | — | 50 | 80 | 90 | — | 80 | 80 | 70 | 70 | 70 | 100 | 100 |
| WILD BUCKWHEAT | — | 40 | 40 | 100 | 20 | 40 | 90 | 100 | 20 | 20 | 90 | 80 |
| BLACKGRASS | — | 30 | 50 | 100 | — | 80 | 80 | 100 | — | 80 | 100 | 100 |
| ALTEX RAPE | — | 90 | 100 | 100 | — | 100 | 100 | 100 | — | 100 | 100 | 100 |
| KLAGES BARLEY | 0 | 40 | 80 | 80 | 60 | 40 | 80 | 100 | 30 | 80 | 100 | 100 |
| GREEN FOXTAIL | — | 50 | 90 | 100 | — | 70 | 70 | 90 | — | 90 | 100 | 100 |
| CHEAT GRASS | 0 | 60 | 90 | 90 | 20 | 40 | 90 | 100 | 40 | 80 | 100 | 100 |
| FIELD VIOLET | — | — | 100 | 100 | — | 80 | 100 | 100 | — | 90 | 100 | 100 |
| LAMBSQUARTER | 50 | 90 | 90 | 100 | 80 | 100 | 100 | 100 | 70 | 100 | 100 | 100 |
| CHICKWEED SPP. | — | 50 | 90 | 100 | — | 60 | 90 | 100 | — | 70 | 90 | 100 |

PRE

| | CMPD 66 | | | | CMPD 67 | | | | CMPD 68 | | | |
|---|---|---|---|---|---|---|---|---|---|---|---|---|
| RATE = G/HA | 0001 | 0004 | 0016 | 0062 | 0001 | 0004 | 0016 | 0062 | 0001 | 0004 | 0016 | 0062 |
| GIANT FOXTAIL | 20 | 40 | 70 | 90 | 20 | 40 | 100 | 100 | 20 | 40 | 90 | 100 |
| VELVETLEAF | 0 | 0 | 40 | 60 | 0 | 30 | 70 | 100 | 30 | 30 | 80 | 90 |
| USH11 SUGARBEET | 40 | 60 | 100 | 100 | 60 | 70 | 100 | 100 | 40 | 40 | 100 | 100 |
| LARGE CRABGRASS | 20 | 70 | 100 | 100 | 30 | 70 | 100 | 100 | 40 | 70 | 100 | 80 |
| PRICKLY SIDA | 30 | 30 | 80 | 100 | 0 | 40 | 90 | 100 | 30 | 80 | 100 | 90 |
| JIMSONWEED | 20 | 20 | 40 | 80 | 20 | 50 | 100 | 100 | 30 | 70 | 100 | 80 |
| RICE DRY SEEDED | 20 | 0 | 60 | 100 | 0 | 20 | 70 | 100 | 20 | 30 | 100 | 100 |
| COCKLEBUR | 0 | 0 | 20 | 0 | 0 | 20 | 30 | 80 | 20 | 20 | 30 | 40 |

TABLE B-continued

| | | | | | | | | | | | | | |
|---|---|---|---|---|---|---|---|---|---|---|---|---|---|
| COKER COTTON | 0 | 0 | 0 | 0 | 0 | 0 | — | 0 | 20 | 0 | 0 | 0 | 40 |
| WILLMS SOYBEANS | 0 | 0 | 30 | 30 | 80 | 0 | 0 | 40 | 80 | 0 | 0 | 20 | 70 |
| BARNYARDGRASS | 20 | 30 | 20 | 40 | 30 | 0 | 20 | 100 | 80 | 20 | 30 | 30 | 80 |
| WILD OATS | 0 | 20 | 40 | 90 | 100 | 0 | 20 | 30 | 100 | 0 | 50 | 60 | 100 |
| IVY MORNINGLORY | 0 | 30 | 90 | 90 | 90 | 0 | 20 | 30 | 90 | 0 | 30 | 50 | 80 |
| ERA WHEAT | 20 | 40 | 80 | 30 | 100 | 0 | 20 | 50 | 100 | 0 | 30 | 60 | 100 |
| SICKLEPOD | 20 | 0 | 30 | 40 | 70 | 20 | 30 | 30 | 40 | 20 | 30 | 80 | 90 |
| JOHNSONGRASS | 0 | 20 | 40 | 80 | 80 | 60 | 60 | 100 | 100 | 0 | 30 | 90 | 100 |
| PURPLE NUTSEDGE | 0 | 0 | 50 | 70 | 70 | 60 | 100 | 100 | 100 | 40 | 30 | 100 | 40 |
| G4646 CORN | 0 | 40 | 100 | 100 | 100 | 30 | 80 | 100 | 100 | 30 | 0 | 90 | 90 |
| WILD BUCKWHEAT | 30 | 50 | 90 | 90 | 100 | 0 | 50 | 80 | 90 | 0 | 70 | 80 | 100 |
| BLACKGRASS | 40 | 60 | 90 | 90 | 100 | 30 | 70 | 100 | 100 | 30 | 50 | 100 | 90 |
| ALTEX RAPE | 0 | 30 | 60 | 90 | 90 | 0 | 20 | 70 | 100 | 0 | 70 | 80 | 100 |
| KLAGES BARLEY | 0 | 20 | 30 | 60 | 100 | 0 | 20 | 90 | 100 | 30 | 40 | 90 | 90 |
| GREEN FOXTAIL | 60 | 70 | 90 | 100 | 100 | 30 | 70 | 80 | 100 | 0 | 30 | 90 | 100 |
| CHEAT GRASS | 0 | 0 | 20 | 80 | 80 | 0 | 30 | 90 | 100 | 0 | 40 | 100 | 90 |
| FIELD VIOLET | 0 | 0 | 0 | 20 | 100 | 0 | 30 | 90 | 100 | 30 | 30 | 70 | 90 |
| LAMBSQUARTER | 0 | 70 | 80 | 90 | 100 | 30 | 70 | 80 | 90 | 40 | 60 | 70 | 80 |
| CHICKWEED SPP. | | | | | | | | | | | | | |

TEST C

Postemergence

Six round pots (17 cm diameter by 15 cm deep) were used to grow plants to the treatment stage. Four were planted with seeds or tubers of four species each and another with soybeans using sassafras sandy loam as the growing media. The sixth pot was planted to corn using a toma silt loam. During spraying, the soil of this pot was temporarily covered with perlite which was later removed so any effects noted would be from foliar uptake only. A separate pot of corn (25.5 cm diameter by 19.5 cm deep) grown in sassafras sandy loam was also included to determine foliar/soil treatment effects on plant growth. Plants were grown 10 to 20 days and were in the 2 to 5 leaf stage when sprayed postemergence with compounds of the invention. Species included were as follows:

| | |
|---|---|
| Corn (maize) | *Zea mays* |
| Soybeans | *Glycine max* |
| Green foxtail | *Setaria viridis* |
| Giant foxtail | *Setaria faberii* |
| Fall Panicum | *Panicum dichotomiflorum* |
| Crabgrass | *Digitaria sanquinalis* |
| Barnyardgrass | *Echinochloa crus-galli* |
| Johnsongrass | *Sorghum halepense* |
| Sorghum | *Sorghum vulgare* |
| Nutsedge | *Cyperus rotundus* |
| Velvetleaf | *Abutilon theophrasti* |
| Cocklebur | *Xanthium pensylvanicum* |
| Smartweed | *Polygonum persicaria* |
| Lambsquarter | *Chenopodium album* |
| Pigweed | *Amaranthus retroflexus* |
| Morningglory | *Ipomoea hederacea* |
| Jimsonweed | *Datura stramonium* |
| Ragweed | *Ambrosia artemisiifolia* |

Preemergence

Plants were grown as above except all in toma silt loam. Compounds were sprayed preemergence the day after planting then all pots were watered to simulate rainfall.

After treatment, all plants were maintained in a greenhouse about 20 days, then visually rated for plant response. Ratings are based on a scale of 0 to 100 (%) where 0=no effect and 100 (%)=complete control. Response ratings are shown in Table C.

TABLE C

| | CMPD 1 | | | | | | CMPD 21 | | | | | | | CMPD 46 | | | |
|---|---|---|---|---|---|---|---|---|---|---|---|---|---|---|---|---|---|
| RATE GM/HA | 0004 | 0008 | 0016 | 0032 | 0064 | 0125 | 0002 | 0004 | 0008 | 0016 | 0032 | 0064 | 0125 | 0002 | 0004 | 0008 | 0016 |
| | | | | | | POST | | | | | | | | | | | |
| SOIL TYPE | SAS | SAS | SAS | SAS | SAS | SAS | SAS | SAS | SAS | SAS | SAS | SAS | SAS | SAS | SAS | SAS | SAS |
| G4646 CORN | 0 | 0 | 0 | 0 | 25 | 40 | 0 | 0 | 0 | 0 | 10 | 20 | 70 | 0 | 0 | 0 | 0 |
| WILLMS SOYBEANS | 0 | 20 | 35 | 50 | 65 | 85 | 95 | 98 | 100 | 100 | 100 | 100 | 100 | 25 | 45 | 75 | 90 |
| GREEN FOXTAIL | 50 | 65 | 80 | 90 | 95 | 100 | 80 | 90 | 90 | 100 | 100 | 100 | 100 | 0 | 30 | 60 | 75 |
| GIANT FOXTAIL | 40 | 65 | 70 | 90 | 95 | 100 | 70 | 90 | 90 | 95 | 100 | 100 | 100 | 0 | 30 | 60 | 75 |
| FALL PANICUM | 70 | 90 | 95 | 100 | 100 | 100 | 80 | 95 | 98 | 100 | 100 | 100 | 100 | 0 | 35 | 70 | 90 |
| LARGE CRABGRASS | 0 | 0 | 0 | 30 | 70 | 80 | 0 | 0 | 0 | 30 | 40 | 60 | 70 | 0 | 0 | 0 | 0 |
| BARNYARDGRASS | 90 | 100 | 100 | 100 | 100 | 100 | 100 | 100 | 100 | 100 | 100 | 100 | 100 | 45 | 90 | 100 | 100 |
| JOHNSONGRASS | 100 | 100 | 100 | 100 | 100 | 100 | 100 | 100 | 100 | 100 | 100 | 100 | 100 | 60 | 80 | 95 | 100 |
| G522 SORGHUM | 100 | 100 | 100 | 100 | 100 | 100 | 100 | 100 | 100 | 100 | 100 | 100 | 100 | 75 | 90 | 100 | 100 |
| PURPLE NUTSEDGE | 30 | 50 | 75 | 90 | 100 | 100 | | | | | | | | 0 | 35 | 45 | 60 |
| VELVETLEAF | 20 | 45 | 75 | 85 | 95 | 100 | 40 | 60 | 60 | 60 | 90 | 100 | 100 | 0 | 0 | 35 | 70 |
| COCKLEBUR | 50 | 85 | 100 | 100 | 100 | 100 | 40 | 40 | 40 | 90 | 100 | 100 | 100 | 0 | 30 | 40 | 60 |
| LADY SMARTWEED | 0 | 0 | 0 | 25 | 50 | 70 | 0 | 0 | 0 | 30 | 50 | 80 | 80 | 0 | 30 | 75 | 85 |
| LAMBSQUARTER | 0 | 0 | 0 | 0 | 35 | 50 | 30 | 30 | 30 | 60 | 40 | 50 | 70 | 0 | 0 | 0 | 30 |
| REDROOT PIGWEED | 70 | 85 | 100 | 100 | 100 | 100 | 90 | 100 | 100 | 100 | 100 | 100 | 100 | 35 | 70 | 100 | 100 |
| IVY MORNINGLORY | 50 | 85 | 100 | 100 | 100 | 100 | 0 | 0 | 0 | 20 | 30 | 40 | 70 | 0 | 0 | 20 | 40 |
| JIMSONWEED | 0 | 0 | 0 | 0 | 0 | 35 | 0 | 20 | 20 | 30 | 40 | 40 | 50 | 0 | 0 | 0 | 0 |
| PERLITE CORN | 0 | 0 | 0 | 0 | 20 | 30 | 0 | 0 | 0 | 10 | 10 | 20 | 60 | 0 | 0 | 0 | 0 |

| | CMPD 46 | | | CMPD 60 | | | | | | | | | |
|---|---|---|---|---|---|---|---|---|---|---|---|---|---|
| RATE GM/HA | 0032 | 0064 | 0125 | 0002 | 0004 | 0008 | 0016 | 0032 | 0064 | 0125 | 0016 | 0032 | 0064 | 0125 |
| | | | | | | POST | | | | | | | | |
| SOIL TYPE | SAS | SAS | SAS | SAS | SAS | SAS | SAS | SAS | SAS | SAS | TAM | TAM | TAM | TAM |
| G4646 CORN | 0 | 0 | 30 | 0 | 0 | 0 | 0 | 30 | 60 | 85 | 0 | 0 | 0 | 0 |
| WILLMS SOYBEANS | 100 | 100 | 100 | 100 | 100 | 100 | 100 | 100 | 100 | 100 | 30 | 40 | 60 | 85 |
| GREEN FOXTAIL | 85 | 90 | 100 | 20 | 35 | 45 | 65 | 75 | 85 | 95 | 20 | 25 | 35 | 60 |
| GIANT FOXTAIL | 85 | 90 | 100 | 0 | 25 | 40 | 60 | 75 | 90 | 100 | 20 | 20 | 30 | 40 |
| FALL PANICUM | 100 | 100 | 100 | 60 | 75 | 90 | 95 | 100 | 100 | 100 | 70 | 80 | 95 | 100 |
| LARGE CRABGRASS | 25 | 35 | 45 | 0 | 0 | 0 | 30 | 40 | 60 | 80 | 0 | 0 | 20 | — |
| BARNYARDGRASS | 100 | 100 | 100 | 80 | 95 | 100 | 100 | 100 | 100 | 100 | 65 | 70 | 90 | 100 |
| JOHNSONGRASS | 100 | 100 | 100 | 95 | 100 | 100 | 100 | 100 | 100 | 100 | 70 | 90 | 100 | 100 |
| G522 SORGHUM | 100 | 100 | 100 | 100 | 100 | 100 | 100 | 100 | 100 | 100 | 75 | 100 | 100 | 100 |
| PURPLE NUTSEDGE | 80 | 95 | 100 | 30 | 50 | 65 | 75 | 100 | 100 | 100 | 35 | 60 | 80 | — |
| VELVETLEAF | 70 | 85 | 95 | 20 | 35 | 55 | 85 | 100 | 100 | 100 | 0 | 0 | 0 | — |
| COCKLEBUR | 75 | 95 | 95 | 35 | 40 | 60 | 70 | 85 | 100 | 100 | 0 | 0 | 0 | — |
| LADY SMARTWEED | 95 | 100 | 100 | 20 | 30 | 40 | 60 | 80 | 100 | 100 | 50 | 65 | 95 | — |
| LAMBSQUARTER | 40 | 55 | 65 | 0 | 0 | 0 | 35 | 60 | 90 | 95 | 25 | 40 | 60 | — |
| REDROOT PIGWEED | 100 | 100 | 100 | 60 | 75 | 100 | 100 | 100 | 100 | 100 | 50 | 60 | 90 | — |
| IVY MORNINGLORY | 60 | 70 | 80 | 0 | 0 | 20 | 40 | 65 | 80 | 95 | 0 | 0 | 0 | — |
| JIMSONWEED | 25 | 40 | 60 | 0 | 0 | 0 | 20 | 40 | 65 | 85 | 0 | 0 | 0 | — |
| PERLITE CORN | 0 | 0 | 25 | 0 | 0 | 0 | 0 | 25 | 50 | 70 | | | | |

TEST D

POTATO TOLERANCE TEST

Potatoes (*Solanum tuberosum*, cult. 'Green Mountain') were grown in Metro 350 medium in 20 cm plastic pots. Potatoes were 17 days old at time of spraying. Barnyardgrass (*Echinochloa crus-galli*), johnsongrass (*Sorghum halepense*), giant foxtail (*Setaria faberii*), crabgrass (*Digitaria sanguinalis*), purple nutsedge (*Cyperus rotundus*), jimsonweed (*Datura stramonium*), velvetleaf (*Abutilon theophrasti*), cocklebur (*Xanthium pensylvanicum*), and morningglory (*Ipomoea hederacea*) were grown in Sassafras sandy loam (pH 6.5, 1% organic matter) in plastic-lined 25 cm pots. These plants were 9 days old at the time of spraying.

Compounds were sprayed at 62, 16, 4, and 1 g/ha. Each rate was sprayed on one pot containing potato plants and at the same time on one pot containing the remaining species. Compounds were dissolved in a non-phytotoxic solvent, 4.0% and were sprayed at 374 l/ha. Plants were maintained in a greenhouse and were evaluated 11 days after spraying.

All sprayed plants were evaluated for injury as compared to control plants. Injury was measured visually using a 0 to 100% scale whre 0=no effect and 100=complete control. Results are shown in Table D.

TABLE D

| | Compound 21 | | | |
|---|---|---|---|---|
| | Rate (g/ha) | | | |
| SPECIES | 62 | 16 | 4 | 1 |
| potato | 0 | 0 | 0 | 0 |
| barnyardgrass | 100 | 100 | 70 | 30 |
| johnsongrass | 100 | 100 | 100 | 60 |
| giant foxtail | 100 | 100 | 90 | 60 |
| crabgrass | 90 | 85 | 60 | 50 |
| purple nutsedge | 90 | 90 | 80 | 30 |
| jimsonweed | 80 | 60 | 40 | 20 |
| velvetleaf | 100 | 95 | 50 | 20 |
| cocklebur | 90 | 50 | 30 | 0 |
| morningglory | 90 | 70 | 40 | 20 |

TEST E

TOMATO AND PEPPER TOLERANCE TEST

Tomatoes (*Lycopersicon esculentum* cult. 'Rutgers') and peppers (*Capsicum frutescens* cult. 'Yolo') were grown in Metro 350 medium in 10 cm plastic pots. Tomatoes and peppers were 19 days old at time of spraying. Purple nutsedge (*Cyperus rotundus*), crabgrass (*Digitaria sanguinalis*), sicklepod (*Cassia tora*), prickley sida (*Sida spinosa*), jimsonweed (*Datura stramonium*), velvetleaf (*Abutilon theophrasti*), lambsquarter (*Chenopodium album*), green foxtail (*Setaria viridis*), cocklebur (*Xanthium pensylvanicum*), morningglory (*Ipomoea hederacea*), johnsongrass (*Sorghum halepense*), barnyardgrass (*Echinochloa crus-galli*), giant foxtail (*Setaria faberii*), wild buckwheat (*Polygonum convolvulus*), downy brome (*Bromus tectorum*), wild oat (*Avena fatua*), chickweed (Stellaria spp.), and blackgrass (*Alopecurus myosuroides*), were grown in sassafras sandy loam (pH 6.5, 1% organic matter) in plastic-lined 25 cm pots. These plants were 7 to 11 days old at the time of spraying.

Compounds were sprayed at 62, 16, 4, and 1 g/ha. Each rate was sprayed on one pot containing tomatoes, one pot containing peppers, and on three pots containing the remaining species. Compounds were dissolved in a non-phytotoxic solvent, and was sprayed at 374 l/ha. Plants were maintained in a greenhouse and were evaluated 16 days after spraying.

All sprayed plants were evaluated for injury as compared to control plants. Injury was measured visually using a 0 to 100% scale where 0=no effect and 100=complete control Results are shown in Table E.

TABLE E

| | Compound 21 | | | |
|---|---|---|---|---|
| | Rate (g/ha) | | | |
| SPECIES | 62 | 16 | 4 | 1 |
| tomatoes | 10 | 0 | 0 | 0 |
| peppers | 80 | 70 | 50 | 30 |
| nutsedge | 100 | 100 | 30 | 0 |
| crabgrass | 90 | 80 | 50 | 30 |
| sicklepod | 100 | 100 | 90 | 40 |
| prickley sida | 100 | 100 | 50 | 20 |
| jimsonweed | 100 | 50 | 10 | 0 |
| velvetleaf | 100 | 100 | 70 | 50 |
| lambsquarter | 60 | 50 | 40 | 0 |
| green foxtail | 100 | 100 | 100 | 50 |
| cocklebur | 100 | 80 | 50 | 20 |
| morningglory | 90 | 85 | 50 | 20 |
| johnsongrass | 100 | 100 | 100 | 50 |
| barnyardgrass | 100 | 100 | 100 | 40 |
| giant foxtail | 100 | 100 | 90 | 40 |
| wild buckwheat | 100 | 90 | 90 | 40 |
| downy brome | 100 | 100 | 80 | 20 |
| wild oats | 100 | 70 | 30 | 20 |
| chickweed | 100 | 100 | 90 | 90 |
| blackgrass | 100 | 100 | 100 | 70 |

What is claimed is:
1. A 3-ethylsulfonyl pyridine represented by the formula

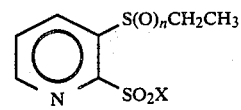

wherein
X is (NHC(CH$_3$)$_3$ or NH$_2$; and
n is 1 or 2.
2. The compound of claim 1 which is 3-ethylsulfonyl-2-pyridinesulfonamide.

* * * * *

UNITED STATES PATENT AND TRADEMARK OFFICE
CERTIFICATE OF CORRECTION

PATENT NO. : 4,774,337
DATED : September 27, 1988
INVENTOR(S) : Paul Hsiao-Tseng Liang It is certified that error appears in the above-identified patent and that said Letters Patent is hereby corrected as shown below:

Column 100, line 50 replace "X is $(NHC(CH_3)_3$ or $NH_2$; and" with --X is $NHC(CH_3)_3$ or $NH_2$; and--.

Signed and Sealed this

Twenty-ninth Day of August, 1989

Attest:

DONALD J. QUIGG

*Attesting Officer*  *Commissioner of Patents and Trademarks*